US007928217B2

(12) United States Patent
Vornlocher et al.

(10) Patent No.: US 7,928,217 B2
(45) Date of Patent: Apr. 19, 2011

(54) NUCLEASE RESISTANT DOUBLE-STRANDED RIBONUCLEIC ACID

(75) Inventors: Hans-Peter Vornlocher, Bayreuth (DE); Ingo Roehl, Memmelsdorf (DE); Philipp Hadwiger, Altenkunstadt (DE); Tracy Stage Zimmermann, Somerville, MA (US); Muthiah Manoharan, Weston, MA (US); Kallanthottathil G. Rajeev, Cambridge, MA (US); Akin Akinc, Newton, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 931 days.

(21) Appl. No.: 11/139,089

(22) Filed: May 27, 2005

(65) Prior Publication Data

US 2006/0094678 A1    May 4, 2006

Related U.S. Application Data

(60) Provisional application No. 60/574,744, filed on May 27, 2004, provisional application No. 60/607,850, filed on Sep. 7, 2004, provisional application No. 60/607,790, filed on Sep. 8, 2004, provisional application No. 60/634,860, filed on Dec. 9, 2004.

(51) Int. Cl.
C07H 21/02 (2006.01)
C07H 21/04 (2006.01)
C12N 15/11 (2006.01)
(52) U.S. Cl. ............... 536/24.5; 536/24.1; 536/24.31; 514/44
(58) Field of Classification Search .................. None
See application file for complete search history.

(56) References Cited

U.S. PATENT DOCUMENTS

| 7,345,027 | B2 * | 3/2008 | Tolentino et al. | ........ 514/44 |
| 2003/0143732 | A1 | 7/2003 | Fosnaugh et al. | |
| 2005/0186591 | A1 * | 8/2005 | Bumcrot et al. | ........ 435/6 |

FOREIGN PATENT DOCUMENTS

| WO | WO 9401550 A1 * | 1/1994 |
| WO | WO 03/070918 | 8/2003 |
| WO | WO 03/099298 A1 | 12/2003 |
| WO | WO 2004/011647 A1 | 2/2004 |
| WO | WO 2004/029212 A2 | 4/2004 |
| WO | WO 2004/044138 A2 | 5/2004 |
| WO | WO 2004080406 A2 * | 9/2004 |
| WO | WO 2005014782 A2 * | 2/2005 |
| WO | WO 2005014811 A2 * | 2/2005 |
| WO | 2005097817 | 10/2005 |

OTHER PUBLICATIONS

Elbashir et al. EMBO Journal, 2001, vol. 20, pp. 6877-6888.*
Parrish et al. Molecular Cell Biology, 2000, vol. 6., pp. 1077-1087.*
Kierzek, Ryszard. Nucleic Acids Research, vol. 20, No. 19, 1992, pp. 5073-5077.*
Basbaum et al., "Focalized proteolysis: spatial and temporal regulation of extracellular matrix degradation at the cell surface" *Curr. Opin. Cell Biol.* 8:731-738 (1996).
Benezra et al., "The Id proteins and angiogenesis" *Oncogene* 20:8334-8341 (2001).
Birkedal-Hansen et al. "Matrix Metalloproteinases: A Review" *Crit. Rev. Oral Biol. Med.* 4:197-250 (1993).
Boyd et al., "Invasion and metastasis" *Cancer Metastasis Rev.* 15:77-89 (1996).
Braasch et al., "Locked Nucleic Acid (LNA) fine-tuning the recognition of DNA and RNA" *Chem. Biol.* 8:1-7 (2001).
Braasch et al., "RNA Interference in Mammalian Cells by Chemically-Modified RNA" *Biochemistry* 42:7967-7975 (2003).
Brinckerhoff et al., "Matrix metalloproteinases: a tail of a frog that became a prince" *Nature Reviews* 3:207-214 (2002).
Chao et al., "BCL-2 Family: Regulators of Cell Death" *Annu. Rev. Immunol.* 16:395-419 (1998).
Childs et al., "The MDR Superfamily of Genes and Its Biological Implications," in *Important Advances in Oncology*, ed. DeVita et al., 21-36. Philadelphia: J.B. Lippencott Co., (1994).
Chiu et al., "siRNA function in RNAi: A chemical modification analysis" *RNA* 9:1034-1048 (2003).
Chothia et al., "The Molecular Structure of Cell Adhesion Molecules" *Annu. TRev. Biochem* 66:823-62 (1997).
Czauderna et al., "Structural variations and stabilizing modifications of synthetic siRNAs in mammalian cells" *Nucleic Acids Research* 31:2705-2716 (2003).
D'Ari, "Cycle-regulated genes and cell cycle regulation" *Bioassays* 23:563-5 (2001).
Elbashir et al., "RNA interference is mediated by 21- and 22-nucleotide RNAs" *EMBO J.* 20:6877-6888 (2001).
Fotedar et al., "Apoptosis and the cell cycle" *Prog. Cell Cycle Res.* 2:147-63 (1996).
Gould et al., "Angiogeneses: An Expanding Universe" *Human Pathol.* 33:1061-1063 (2002).
Hammond et al., "An RNA-Directed Nuclease Mediates Post-Transcriptional Gene Silencing in *Drosophila* Cells," *Nature* 404:293-296 (2000).
Hanahan et al., "The Hallmarks of Cancer" *Cell* 100:57-70 (2000).
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" *Tetrahedron* 54:3607-3630 (1998).
Krepela, "Cysteine proteinases in tumor cell growth and apoptosis" *Neoplasma* 48:332-349 (2001).
Matrisian, "Cancer Biology: Extracellular proteinases in malignancy" *Curr. Biol.* 9:R776-R778 (1999).
Mendelsohn et al., "The EGF receptor family as targets for cancer therapy" *Oncogene* 19:6550-6565 (2001).

(Continued)

Primary Examiner — Janet L. Epps-Smith
(74) Attorney, Agent, or Firm — Jeffrey N. Townes; LeClairRyan

(57) ABSTRACT

This invention relates to modified double-stranded oligoribonucleic acid (dsRNA) having improved stability in cells and biological fluids, and methods of making and identifying dsRNA having improved stability, and of using the dsRNA to inhibit the expression or function of a target gene.

19 Claims, 15 Drawing Sheets

OTHER PUBLICATIONS

Mignatti et al., "Biology and Biochemistry of Proteinases in Tumor Invasion" *Physiol. Rev.* 73:161-195 (1993).

Müllauer et al., "Mutations in apoptosis genes: a pathogenetic factor for human diseases" *Mutat. Res.* 488:211-231 (2001).

Normanno et al., "The Role of EGF-Related Peptides in Tumor Growth" *Front. Biosci.* 6.D685-707, (2001).

Norton, "ID helix-loop-helix proteins in cell growth, differentiation and tumorigenesis" *J. Cell Sci.* 113:3897-905 (2000).

Obika et al., "Stability and structural features of the duplexes containing nucleoside analogues with a fixed N-type conformation, 2'-O,4'-C-methyleneribonucleosides" *Tetrahedron Lett.* 39:5401-5404 (1998).

Parise et al., "New aspects of integrin signaling in cancer" *Semin. Cancer Biol.* 10:407-414 (2000).

Prusiner et al., "Prion Protein Biology" *Cell* 93:337-348 (1998).

Reed,, "Mechanisms of Apoptosis" *Am. J. Pathol.* 157:1415-1430 (2000).

Rubinstein et al. "Recent Advances in Cytokines, Cytokine Receptors and Signal Transduction" *Cytokine Growth Factor Rev.* 9:175-81 (1998).

Safar et al., "Molecular studies of prion diseases" *Prog. Brain Res.* 117:421-434 (1998).

Stetler-Stevenson et al., "Tumor Cell Interactions with the Extracellular Matrix During Invasion and Metastasis" *Annu. Rev. Cell Biol.* 9:541-573 (1993).

Strasser et al., "Apoptosis Signaling" *Annu. Rev. Biochem.* 69:217-245 (2000).

Yokota, "Tumor progression and metastasis" *Carcinogenesis* 21:497-503 (2000).

Hammond et al., "Post-Transcriptional Gene Silencing by Double-Stranded RNA" *Nature Reviews Genetics* 2:110-119 (2001).

Parrish et al., "Functional Anatomy of a dsRNA Trigger: Differential Requirement for the Two Trigger Strands in RNA Interference" *Molecular Cell* 6:1077-1087 (2000).

GenBank Accession No. D89815, Hepatitis C virus genomic RNA, complete sequence, Mar. 7, 1998.

GenBank Accession No. NM_000384, Homo sapiens apolipoprotein B (including Ag(x) antigen) (APOB), mRNA, Apr. 22, 2005.

GenBank Accession No. U47298, Cloning vector pGL3-Promoter, complete sequence, Apr. 17, 2002.

GenBank Accession No. X75932, H.sapiens PLK mRNA for serine/threonine protein kinase, May 5, 1994.

Layzer et al., "In vivo activity of nuclease-resistant siRNAs", vol. 10, No. 5, 2004, pp. 766-771.

Prakash et al., "Positional effects of chemical modification on siRNA activity", Internet Citation, [online], Mar. 28, 2004, p. MEDI175.

Harborth et al., "Sequence, chemical, and structural variation of small interfering RNAs and short hairpin RNAs and the effect on mammalian gene silencing", Antisense & Nucleic Acid Drug Deveopment, vol. 13, No. 2, 2003, pp. 83-105.

Elbashir, et al., "Duplexes of 21-Nucleotide RNAs Mediate RNA Interference in Cultured Mammalian Cells", Nature, vol. 411, 2001, pp. 494-498.

\* cited by examiner

Solid phase (controlled pore glass, CPG)

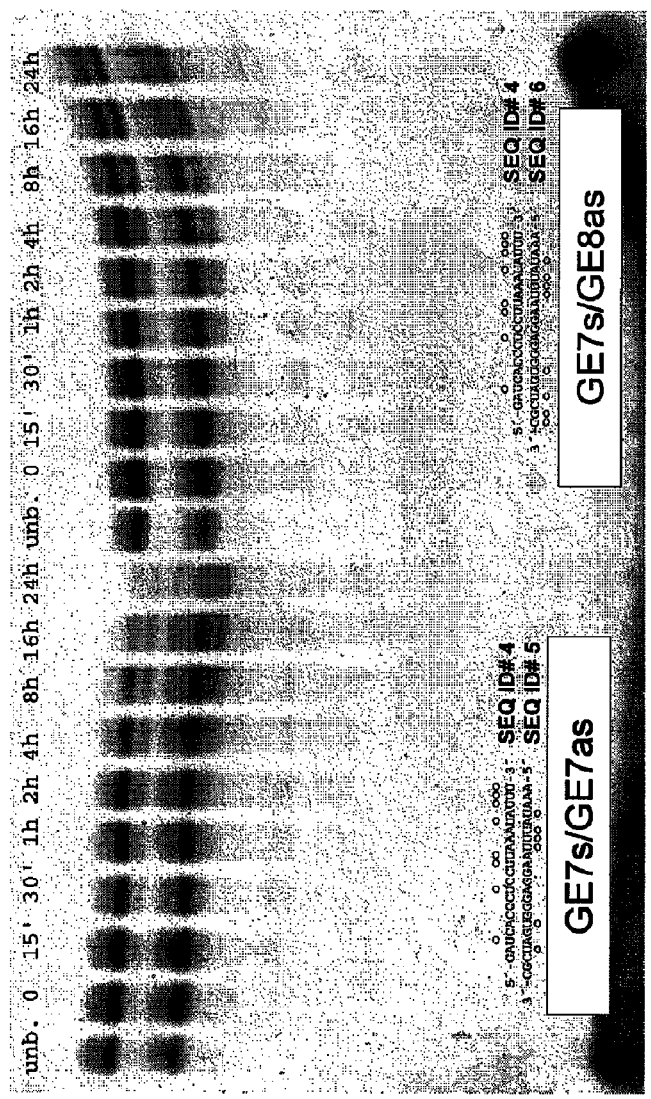
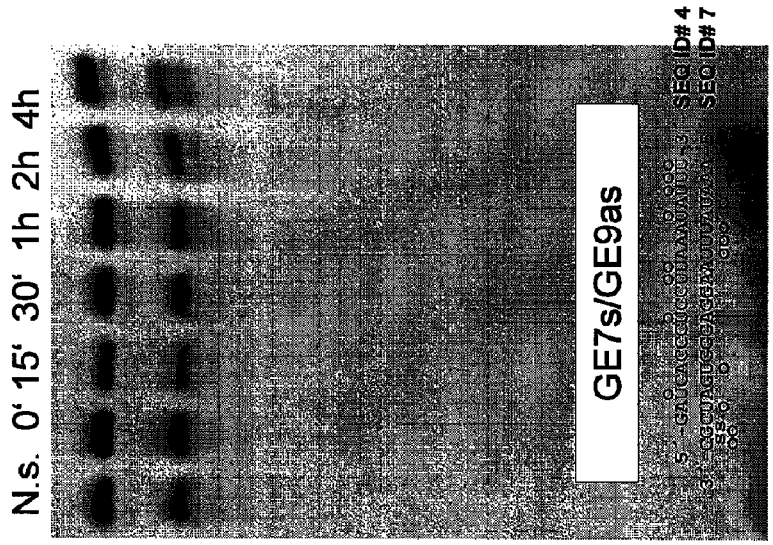
Figure 10
Figure 9
Figure 8

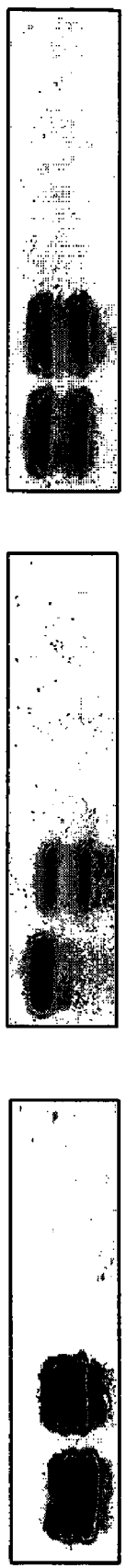
FIG. 31
FIG. 30
FIG. 29

NUCLEASE RESISTANT DOUBLE-STRANDED RIBONUCLEIC ACID

RELATED APPLICATIONS

This application claims the benefit of U.S. Provisional Application No. 60/574,744, filed May 27, 2004; U.S. Provisional Application No. 60/607,850, filed Sep. 7, 2004; U.S. Provisional Application No. 60/607,790, filed Sep. 8, 2004; and U.S. Provisional Application No. 60/634,860, filed Dec. 9, 2004. Each of these applications is incorporated herein by reference in its entirety.

SUBMISSIONS ON COMPACT DISC

A Sequence Listing as required under 37 C.F.R. §1.821(c) is submitted on a compact disc as permitted under 37 C.F.R. §1.52(e). The data file on the compact disc has the file name 14174-08600.txt, contains 55 KB of data, and was created on Sep. 12, 2005. The contents of the compact disc are hereby incorporated by reference in their entirety.

Two duplicate copies (Copy 1 and Copy 2) of the compact disc are submitted. The contents of Copy 1 and Copy 2 are identical.

FIELD OF THE INVENTION

This invention relates to modified double-stranded oligoribonucleic acid (dsRNA) having improved stability in cells and biological fluids, and methods of making and identifying dsRNA having improved stability, and of using the dsRNA to inhibit the expression or function of a target gene.

BACKGROUND OF THE INVENTION

Many diseases (e.g., cancers, hematopoietic disorders, endocrine disorders, and immune disorders) arise from the abnormal expression or activity of a particular gene or group of genes. Similarly, disease can result through expression of a mutant form of protein, as well as from expression of viral genes that have been integrated into the genome of their host. The therapeutic benefits of being able to selectively silence these abnormal or foreign genes are obvious.

Double-stranded RNA molecules (dsRNA) can block gene expression by virtue of a highly conserved regulatory mechanism known as RNA interference (RNAi). Briefly, the RNA III Dicer enzyme processes dsRNA into small interfering RNA (siRNA) of approximately 22 nucleotides. One strand of the siRNA (the "antisense strand") then serves as a guide sequence to induce cleavage of messenger RNAs (mRNAs) comprising a nucleotide sequence which is at least partially complementary to the sequence of the antisense strand by an RNA-induced silencing complex RISC (Hammond, S. M., et al., Nature (2000) 404:293-296). The antisense strand is not cleaved or otherwise degraded in this process, and the RISC comprising the antisense strand can subsequently effect the cleavage of further mRNAs.

SUMMARY OF THE INVENTION

The present invention discloses double-stranded ribonucleic acid (dsRNA) having improved stability in cells and biological fluids, methods of making and identifying dsRNA having improved stability, as well as compositions and methods for inhibiting the expression of a target gene in a cell using the dsRNA. The present invention also discloses compositions and methods for treating diseases caused by the expression or activity of the target gene. The dsRNA of the invention comprises at least one type of nucleotide modified in the 2'-position, which type of nucleotide is in a sequence context rendering it particularly prone to endonucleolytic degradation. Such modification renders the dsRNA more resistant to enzymatic or chemical degradation, and thus more stable and bioavailable than an otherwise identical dsRNA but without the modified nucleotide.

In one aspect, the invention relates to a double-stranded ribonucleic acid (dsRNA) having increased stability in a biological sample, wherein the dsRNA comprises at least one of (a) 2'-modified uridines in all occurrences of the sequence motif 5'-uridine-adenine-3' (5'-ua-3'), or (b) 2'-modified uridines in all occurrences of the sequence motif 5'-uridine-guanine-3' (5'-ug-3'), or (c) 2'-modified cytidines in all occurrences of the sequence motif 5'-cytidine-adenine-3' (5'-ca-3'), or (d) 2'-modified 5'-most uridines in all occurrences of the sequence motif 5'-uridine-uridine-3' (5'-uu-3'), or (e) 2'-modified 5'-most cytidines in all occurrences of the sequence motif 5'-cytidine-cytidine-3' (5'-cc-3'), or (f) 2'-modified cytidines in all occurrences of the sequence motif 5'-cytidine-uridine-3' (5'-cu-3'), or (g) 2'-modified uridines in all occurrences of the sequence motif 5'-uridine-cytidine-3' (5'-uc-3').

The dsRNA of the invention may comprise at least two, three, four or five different features of the features (a) through (g) above. Where there are at least four different features of the features (a) through (g) above, the four different features may be chosen to be (a), (b), (c), and (d). The dsRNA may comprise at least two or at least three occurrences of at least one of the sequence motifs of (a) through (g). The dsRNA may further comprise at least one dinucleotide selected from the group of 5'-uu-3', 5'-ua-3', 5'-ug-3', 5'-uc-3', 5'-cu-3', 5'-ca-3', 5'-cg-3', 5'-cc-3', wherein no nucleotide is a 2'-O-modified nucleotide. The 2'-modified nucleotide can be a 2'-deoxy nucleotide, a 2'-O-methyl nucleotide, a 2'-deoxyfluoro nucleotide, a 2'-O-methoxyethyl nucleotide, a 2'-O-NMA, a 2'-DMAEOE, a 2'-AP, 2'-hydroxy, 2'-ara-F, or a locked nucleic acid nucleotide, extended nucleic acid, hexose nucleic acid, or cyclohexose nucleic acid. The dsRNA may further comprise a nucleotide overhang having 1 to 4 unpaired nucleotides. The overhang may be free of nucleotides T and U. The overhang may have the nucleotide sequence 5'-gcnn-3', wherein n is a, g, c, u, T, U or nothing. The first paired nucleotide adjacent to the 5'-guanine of the 5'-gcnn-3' overhang can be a cytidine (c). The unpaired nucleotides may comprise at least one phosphorothioate dinucleotide linkage. The nucleotide overhang can be at the 3'-end of the antisense RNA strand of the dsRNA. The antisense RNA strand of the dsRNA can comprise a nucleotide sequence 18-30 nucleotides in length which is complementary to the sense strand. The antisense and sense RNA strands of the dsRNA can be connected by a chemical linker.

In a second aspect, the invention relates to a method of preparing a pharmaceutical composition, comprising formulating the dsRNA of the invention in a pharmaceutically acceptable carrier.

In a third aspect, the invention relates to a pharmaceutical composition for inhibiting the expression of a target gene in a mammal, comprising at least one dsRNA of the invention and a pharmaceutically acceptable carrier. The pharmaceutically acceptable carrier may be an aqueous solution, e.g. physiological saline.

In a fourth aspect, the invention relates to a method for inhibiting the expression of a target gene in a cell, comprising the steps of introducing a dsRNA of the invention into the cell, and maintaining the cell for a time sufficient to obtain inhibition of expression of the target gene in the cell, wherein methods of treatment or diagnosis to be performed on a human or animal body are excluded. The cell may be a mammalian cell.

In a fifth aspect, the invention relates to a method for making a double-stranded RNA (dsRNA) with high stability in biological samples for inhibiting the expression of a target gene comprising the steps of:
  (a) selecting one or more nucleotide sequences of between 18 and 30 nucleotides in length from the nucleotide sequence of the mRNA resulting from the transcription of the target gene; and
  (b) synthesizing one or more dsRNAs, wherein one strand comprises a sequence complementary to one of the nucleotide sequences selected in a.; and
  (c) testing said one or more dsRNAs for their capability to inhibit the expression of the target gene in a biological sample; and
  (d) selecting one of the one or more dsRNAs of c. possessing the capability to inhibit the expression of the target gene in a biological sample; and
  (e) in the dsRNA selected in d., identifying in the nucleotide sequences of the sense strand as well as the antisense strand all occurrences of the dinucleotides 5'-ua-3', 5'-ca-3', 5'-ug-3', 5'-uu-3', 5'-cc-3', 5'-uc-3' and 5'-cu-3'; and
  (f) synthesizing a dsRNA, wherein the 5'-uridines and/or 5'-cytidines in all occurrences of at least one of the dinucleotides identified in e. is replaced by a 2'-modified uridine and/or cytidine, respectively.

In one embodiment of this method, the 5'-uridines and/or 5'-cytidines in all occurrences of at least two of the dinucleotides identified in e. are replaced by a 2'-modified uridine and/or cytidine, respectively. Preferably, the 5'-uridines and/or 5'-cytidines in all occurrences of at least three of the dinucleotides identified in e. are replaced by a 2'-modified uridine and/or cytidine, respectively. More preferably, the 5'-uridines and/or 5'-cytidines in all occurrences of at least four of the dinucleotides identified in e. are replaced by a 2'-modified uridine and/or cytidine, respectively. Said four dinucleotides may, for example, be 5'-ua-3', 5'-ug-3', 5'-uu-3', and 5'-ca-3'. Most preferably, the 5'-uridines and/or 5'-cytidines in all occurrences of at least five of the dinucleotides identified in e. are replaced by a 2'-modified uridine and/or cytidine, respectively.

In a sixth aspect, the invention relates to a method of treating a disease caused by expression of a target gene in a subject, said method comprising administering to said subject a pharmaceutical composition comprising the dsRNA of the invention and a pharmaceutically acceptable carrier. Said subject may, for example, be a human.

In a seventh aspect, the invention relates to a method of increasing the nuclease resistance of a dsRNA, comprising the steps of:
  (a) identifying in the nucleotide sequences of the sense strand as well as the antisense strand of the dsRNA all occurrences of the dinucleotides 5'-ua-3', 5'-ca-3', 5'-ug-3', 5'-uu-3', 5-cc-3', 5'-uc-3' and 5'-cu-3'; and
  (b) replacing the 5'-uridines and/or 5'-cytidines in all occurrences of at least one of the dinucleotides identified in (a) by 2'-modified uridines and/or cytidines, respectively.

In a preferred embodiment of said method, all of the 5'-uridines and/or 5'-cytidines in at least two of the dinucleotides identified in (a) are replaced by 2'-modified uridines and/or cytidines, respectively. Preferably, all of the 5'-uridines and/or 5'-cytidines in at least three of the dinucleotides identified in (a) are replaced by 2'-modified uridines and/or cytidines, respectively. More preferably, all of the 5'-uridines and/or 5'-cytidines in at least four of the dinucleotides identified in (a) are replaced by 2'-modified uridines and/or cytidines, respectively. Said four dinucleotides may, for example, be 5'-ua-3', 5'-ug-3', 5'-uu-3', and 5'-ca-3'. Most preferably, all of the 5'-uridines and/or 5'-cytidines in at least five of the dinucleotides identified in (a) are replaced by 2'-modified uridines and/or cytidines, respectively.

In another embodiment, the replacement of uridines and cytidines by 2'-modified uridines and cytidines, respectively, is carried out stepwise, wherein
  (a) in one step, all uridines in a 5'-ua-3' sequence context are replaced by 2'-modified uridines, and,
  (b) in an optional further step, all uridines in a 5'-ua-3' sequence context and all cytidines in a 5'-ca-3' sequence context are replaced by the respective 2'-modified nucleotides, and,
  (c) in an optional further step, all uridines in a 5'-ua-3' sequence context and all cytidines in a 5'-ca-3' sequence context and all uridines in a 5'-ug-3' are replaced by the respective 2'-modified nucleotides, and,
  (d) in an optional further step, all uridines in a 5'-ua-3' sequence context and all cytidines in a 5'-ca-3' sequence context and all uridines in a 5'-ug-3' and all uridines in a 5'-uu-3' sequence context are replaced by the respective 2'-modified nucleotides, and,
  (e) in an optional further step, all uridines in a 5'-ua-3' sequence context and all cytidines in a 5'-ca-3' sequence context and all uridines in a 5'-ug-3' and all uridines in a 5'-uu-3' sequence context and all cytidines in a 5'-cc-3' sequence context are replaced by the respective 2'-modified nucleotides, and,
  (f) in an optional further step, all uridines in a 5'-ua-3' sequence context and all cytidines in a 5'-ca-3' sequence context and all uridines in a 5'-ug-3' and all uridines in a 5'-uu-3' sequence context and all cytidines in a 5'-cc-3' sequence context and all uridines in a 5'-uc-3' sequence context are replaced by the respective 2'-modified nucleotides, and,
  (g) in an optional further step, all uridines in a 5'-ua-3' sequence context and all cytidines in a 5'-ca-3' sequence context and all uridines in a 5'-ug-3' and all uridines in a 5'-uu-3' sequence context and all cytidines in a 5'-cc-3' sequence context and uridines in a 5'-uc-3' sequence context and all cytodines in a 5'-cu-3' are replaced by the respective 2'-modified nucleotides, wherein at least one of steps (a) through (g) is actually performed and wherein, after each step, the stability of the modified dsRNA(s) in biological samples is determined.

In an eighth aspect, the invention relates to a method to identify a dsRNA with increased stability in biological samples, comprising the steps of:
  (a) synthesizing a first dsRNA of claim 1 and a second dsRNA identical to the first dsRNA except that it does not comprise the 2'-modified nucleotides of the dsRNA of claim 1, and
  (b) determining the stability of said first and said second dsRNA in a biological sample by contacting both under identical conditions with the biological sample, and monitoring their degradation, whereby, where the first dsRNA is degraded less rapidly than the second dsRNA, a dsRNA with increased stability in biological samples is identified.

In a ninth aspect, the invention relates to a method of treating a disease caused by expression of a target gene in a subject, said method comprising administering to said subject a pharmaceutical composition comprising the dsRNA of claim of the first aspect of the invention, and a pharmaceutically acceptable carrier.

While RNA interference using dsRNA has been shown to be an effective means for selective gene silencing, RNA can have less than desired stability in some bodily fluids, particularly in serum.

Thus, RNA, including dsRNA, can be degraded between the time it is administered to a subject and the time it enters a target cell. Even within the cell, RNA can undergo rapid degradation by nucleases. Methods of the invention can provide more stable or nuclease resistant dsRNAs that can offer better bioavailability and hence improved effectiveness. This is an improvement over the current insufficient methods for stabilizing dsRNA against degradation.

Thus despite significant recent developments in the field of RNA interference, there remains a need for a more effective dsRNA molecule that can selectively and efficiently silence a target gene. More specifically, a dsRNA molecule having enhanced resistance to chemical and/or enzymatic degradation, and hence improved stability in biological samples and bioavailability, and which can be readily and cost-effectively synthesized would be highly desirable. Compositions comprising such agents would be useful for treating diseases caused by abnormal expression or activity of a gene.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

FIG. 8 shows a gel electrophoretic separation, stained using the "stains all" reagent, of a nuclease resistant dsRNA of the present invention (referred to as "GE7s/GE9as") after 0, 15, 30, 60, 120 and 240 minutes of incubation in serum.

FIG. 9 shows a gel electrophoretic separation, stained using the "stains all" reagent, of a nuclease resistant dsRNA of the present invention (referred to as "GE7s/GE7as") after 0, 15, and 30 minutes, and 1, 2, 4, 8, 16 and 24 hours of incubation in serum.

FIG. 10 shows a gel electrophoretic separation, stained using the "stains all" reagent, of a nuclease resistant dsRNA of the present invention (referred to as "GE7s/GE8as") after 0, 15, and 30 minutes, and 1, 2, 4, 8, 16 and 24 hours of incubation in serum.

FIG. 29 shows a gel electrophoretic separation, stained using the "stains all" reagent, of the dsRNAs referred to herein as AL-DP-5098, AL-DP-5399, and AL-DP-5459 untreated (N.s.) or treated by incubation with human serum for 0, 1, 3, or 6 hours. Labels "2'-OMe" and "2'-F" have the meaning as described for FIG. 23.

FIG. 30 shows a gel electrophoretic separation, stained using the "stains all" reagent, of the dsRNAs referred to herein as AL-DP-5089, AL-DP-5395, and AL-DP-5455 untreated (N.s.) or treated by incubation with human serum for 0, 1, 3, or 6 hours. Labels "2'-OMe" and "2'-F" have the meaning as described for FIG. 23.

FIG. 31 shows a gel electrophoretic separation, stained using the "stains all" reagent, of the dsRNAs referred to herein as AL-DP-5030, AL-DP-5389, and AL-DP-5449 untreated (N.s.) or treated by incubation with human serum for 0, 1, 3, or 6 hours. Labels "2'-OMe" and "2'-F" have the meaning as described for FIG. 23.

DETAILED DESCRIPTION OF THE INVENTION

Figure 3:
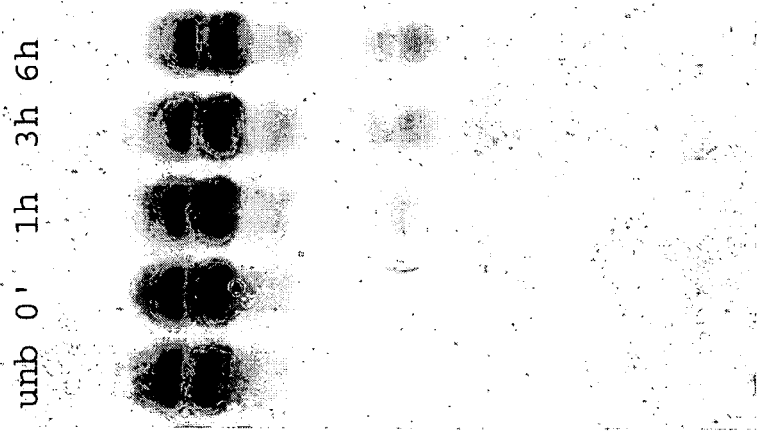
FIG. 3 shows a gel electrophoretic separation, stained using the "stains all" reagent, of the dsRNA referred to herein as AL-DP-5392 untreated (unb) or treated by incubation with human serum for 0, 1, 3, or 6 hours. AL-DP-5392 is identical in nucleotide sequence to AL-DP-5437, except that is bears additional 2'-modifications in the 5'-most uridines or cytidines of all occurrences of the sequence motifs 5'-ua-3', 5'-ug-3', 5'-uu-3', and 5'-ca-3', protecting this dsRNA against exonucleolytic and endonucleolytic attack.

The present invention discloses modified double-stranded ribonucleic acid (dsRNA) having improved stability in cells and biological fluids compared to unmodified dsRNA recognizing the same target RNA, methods of making the modified dsRNA, as well as compositions and methods for inhibiting the expression of a target gene in a cell or mammal using the dsRNA. The present invention also discloses compositions and methods for treating diseases in organisms caused by expression of a target gene using the modified dsRNA. dsRNA directs the sequence-specific degradation of mRNA through a process known as RNA interference (RNAi). The process occurs in a wide variety of organisms, including mammals and other vertebrates. The dsRNA of the invention comprises an antisense strand and a sense strand, wherein the antisense strand has a nucleotide sequence which is complementary to a target RNA, and comprises at least one of: 2'-modified uridines in all occurrences of the sequence motif 5'-uridine-adenine-3' (5'-ua-3'), or 2'-modified uridines in all occurrences of the sequence motif 5'-uridine-guanine-3' (5'-ug-3'), or 2'-modified cytidines in all occurrences of the sequence motif 5'-cytidine-adenine-3' (5'-ca-3'), or 2'-modified 5'-most uridines in all occurrences of the sequence motif 5'-uridine-uridine-3' (5'-uu-3'), or 2'-modified 5'-most cytidines in all occurrences of the sequence motif 5'-cytidine-cytidine-3' (5'-cc-3'), or 2'-modified cytidines in all occurrences of the sequence motif 5'-cytidine-uridine-3' (5'-cu-3'), or 2'-modified uridines in all occurrences of the sequence motif 5'-uridine-cytidine-3' (5'-uc-3'). The present inventors have discovered that dsRNAs comprising such modifications (i.e., a modified dsRNA) have significantly improved stability in biological samples compared to their unmodified dsRNA counterparts. The dinucleotide(s) chemically modified in the 2'-position may be strategically placed within the dsRNA for optimal stability and without affecting the interference activity. The present invention encompasses these modified dsRNAs, compositions comprising the modified dsRNAs, and the use of these compositions for specifically inactivating gene function. The use of modified dsRNAs having improved resistance to enzymatic degradation (i.e., increased in vivo half-life), and hence improved bioavailability, facilitates the targeted degradation of mRNA of genes that are implicated in a wide variety of disease processes. Because of the improved bioavailability of the modified dsRNAs, less dsRNA is required to produce the desired RNA interference effect. Thus, the methods and compositions of the present invention comprising the modified dsRNAs are useful for treating diseases and disorders caused by the expression or activity of a particular gene.

The invention also relates to methods of making and using the dsRNAs and compositions containing dsRNAs having improved stability in biological samples to inhibit the expression of a target gene, as well as compositions and methods for treating diseases and disorders caused by the expression of the target gene. Exemplary pharmaceutical compositions comprise a modified dsRNA having an antisense nucleotide sequence of, for example, 18 to 25 nucleotides in length, preferably 22 nucleotides in length, and which is substantially complementary to a region of an mRNA transcript of the target gene, together with a pharmaceutically acceptable carrier.

Accordingly, certain aspects of the present invention relate to pharmaceutical compositions comprising the modified dsRNA of the present invention together with a pharmaceutically acceptable carrier, methods of making and using the modified dsRNA to inhibit expression of a target gene, and methods of making and using the modified dsRNA to treat diseases caused by the expression or activity of a particular gene. Methods of identifying dsRNA having improved stability are also disclosed.

1. Definitions

For convenience, the meaning of certain terms and phrases used in the specification, examples, and appended claims, are provided below.

As used herein, "target gene" refers to a section of a DNA strand of a double-stranded DNA that is complementary to a section of a DNA strand, including all transcribed regions, that serves as a template for transcription. A target gene, usually the sense strand, is a gene whose expression is to be selectively inhibited or silenced through RNA interference. The term "target gene" specifically encompasses any cellular gene or gene fragment whose expression or activity is associated with a disease or disorder (e.g., an oncogene), as well as any foreign or exogenous gene or gene fragment whose expression or activity is associated with a disease, such as a gene from a pathogenic organism (e.g., a viral or pro-viral gene, viroid, or plasmodium). The target gene may be a viral gene, for example a (+) strand RNA virus such as a Hepatitis C Virus (HCV).

As used herein, the term "double-stranded RNA" or "dsRNA" (also called "siRNA" or "iRNA agent") refers to a ribonucleic acid molecule having a duplex structure comprising two at least partly, and preferably fully, mutually complementary and anti-parallel nucleic acid strands. The strands forming the duplex structure may be comprised on separate molecules, or they may be part of a single molecule, i.e. linked by one or more covalent bonds. Not all nucleotides of a dsRNA must exhibit Watson-Crick base pairs; the two RNA strands may be substantially complementary (i.e., having no more than two, preferably no more than one, nucleotide mismatches per 10 contiguous nucleotide base pairs). The RNA strands may have the same or a different number of nucleotides. Preferably, the complementary region between the antisense and sense RNA strands is at least 10, 15, 18, 19, 20, 22 or 23 nucleotides, but no more than 23, 24, 25, 28, 30, 35, or 49 nucleotides, in length. The term "duplex" or "duplex structure" refers to the region of the dsRNA molecule wherein the two separate RNA strands or the single self-complementary RNA strand are complementary, and thus hybridize to form a double-stranded structure.

The term "antisense RNA strand" (also referred to herein as the "antisense strand") refers to the strand of a dsRNA that is complementary to an mRNA transcript that is formed during expression of the target gene, or its processing products, or a region (such as the 3'-UTR) of a (+) strand RNA virus. As used herein, the term "antisense nucleotide sequence" refers to the region on the antisense RNA strand that is complementary to a region of an mRNA transcript of the target gene or a region (e.g., 3'-UTR) of a (+) strand RNA virus.

As used herein, "modified dsRNA" refers to a dsRNA molecule that comprises at least one alteration. The modified dsRNAs of the present invention include at least one of: 2'-modified uridines in all occurrences of the sequence motif 5'-uridine-adenine-3' (5'-ua-3'), or 2'-modified uridines in all occurrences of the sequence motif 5'-uridine-guanine-3' (5'-ug-3'), or 2'-modified cytidines in all occurrences of the sequence motif 5'-cytidine-adenine-3' (5'-ca-3'), or 2'-modified 5'-most uridines in all occurrences of the sequence motif 5'-uridine-uridine-3' (5'-uu-3'), or 2'-modified 5'-most cytidines in all occurrences of the sequence motif 5'-cytidine-cytidine-3' (5'-cc-3'), or 2'-modified cytidines in all occurrences of the sequence motif 5'-cytidine-uridine-3' (5'-cu-3'), or 2'-modified uridines in all occurrences of the sequence motif 5'-uridine-cytidine-3' (5'-uc-3').

The terms "modified nucleotide," "substituted nucleotide," and "additional nucleotide," as used herein, refer to a nucleotide which has been altered, or added to a nucleic acid sequence of a dsRNA in replacement of another nucleotide, or simply added to such nucleic acid sequence, respectively, to render the dsRNA more resistant to nucleases (i.e., more stable) than a naturally occurring dsRNA or a chemically synthesized dsRNA that recognizes the same target sequence but lacks the alteration, substitution, or addition of such nucleotide. Exemplary modifications that generate modified, substituted, or additional nucleotides that increase the stability of the dsRNA include, for example, replacing a naturally occurring or wild-type nucleotide with a 2'-modified nucleotide, as defined below (e.g., replacing a uridine with a 2'-O-methyl uridine or a 2'-deoxy-2'-fluoro uridine), addition of one or more unpaired nucleotides or dinucleotides at an end of the double stranded structure (e.g., incorporating a 5'-GC-3' sequence which does not normally flank the target RNA sequence), chemical modification of a nucleotide (e.g., replacing a 2'-hydroxyl group on the sugar moiety with a 2'-O-methyl group or a 2'-deoxy-2'-fluoro group), and alteration of a nucleotide linkage (e.g., replacing a phosphodiester bond with a phosphorothioate bond). The "modified dsRNA" of the present invention contains a modification in its chemical structure that produces a measurable increase in stability as compared to an identical dsRNA without the substituted or modified nucleotide.

Particularly, the term "2'-modified nucleotide," as used herein, refers to a nucleotide which has been modified as to prevent the enzymatic cleavage of the phosphate backbone of an RNA at or near the nucleotide so modified. Often, such cleavage is mediated by the 2'-OH of a nucleotide via formation of a cyclic phosphate. Removing or replacing the 2'-OH group can effectively block cleavage, e.g. by not allowing the formation of the cyclic phosphate. Modifications within the scope of the instant invention include, without limitation, the removal of the 2'-OH, resulting in a 2'-deoxy nucleotide, or the replacement of the 2'-OH by $OR^1$, $O(CH_2CH_2O)_m CH_2CH_2OR^1$; $O(CH_2)_nR^2$; $O(CH_2)_nOR^2$, halogen; $NH_2$; $NHR^1$; $N(R^1)_2$; $NH(CH_2CH_2NH)_mCH_2CH_2NHR^9$; $NHC(O)R^1$; cyano; mercapto, $SR^1$; alkyl-thio-alkyl; alkyl, aralkyl, cycloalkyl, aryl, heteroaryl, alkenyl, or alkynyl, each of which may be optionally substituted with halogen, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, or ureido; $R^1$ is alkyl, cycloalkyl, aryl, aralkyl, heterocyclyl, heteroaryl, amino acid, or sugar; $R^2$ is $NH_2$, alkylamino, dialkylamino, heterocyclyl, arylamino, diaryl amino, heteroaryl amino, diheteroaryl amino, or amino acid; m is 0-1,000,000, and n is 0-20; or the 2'-oxygen may be used to form an [—O—$CH_2$—] covalently bound bridge between the sugar 2' and 4' carbon atoms (commonly, a "locked nucleic acid"). The skilled person will be aware of further modifications to achieve the desired effect of blocking endonuclease cleavage. Furthermore, additional such modifications developed in the future but are equivalent in effect are within the scope of the present invention.

As used herein, the terms "stability" and "stable" refer to resistance to degradation, e.g., by chemicals or nucleases, specifically endonucleases, which normally degrade RNA molecules. The modified dsRNA molecules of the present invention have a measurable change in stability, and hence longer half-lives, than their unmodified dsRNA counterparts.

As used herein, a "measurable change" or "measurable increase" in dsRNA stability refers to a quantity that is empirically determined and that will vary depending upon the method used to monitor dsRNA stability. The present invention encompasses any difference between the test and control combinations in any measurable physical parameter (e.g., stability in serum), where the difference is greater than expected due to random statistical variation. For example, a modified dsRNA of the present invention has "increased stability" or is "more stable" than a control dsRNA when the amount of non-degraded modified dsRNA is at least 10%, 25%, 35%, or 50% more than that of a control dsRNA after incubation of both dsRNAs with, for example, a biological sample.

As used herein, the term "control" refers to a dsRNA molecule that is structurally similar or identical to a modified dsRNA molecule except that it lacks at least one of the modified, substituted, or added nucleotides present in the modified dsRNA. As will be appreciated by those skilled in the art, the "control" dsRNA will depend upon the experimental design, and will vary depending upon the structural feature or features being evaluated. Preferably, the modified dsRNAs of the invention are substantially resistant to enzymatic (e.g., endonuclease and exonuclease) degradation, more preferably substantially resistant to endonucleases, and most preferably highly resistant to endonucleases. Also as used herein, the term "control cell" refers to a cell that is capable of expressing a target gene, and which does not include the modified dsRNA.

As used herein, a modified dsRNA is "substantially resistant" to nucleases when it is at least about 2-fold more resistant to attack by one nuclease, or a set of nucleases, and is "highly nuclease resistant" when it is at least about 5-fold more resistant to a nuclease or a set of nucleases than a control dsRNA.

As used herein, the term "biological sample" refers to a whole organism or a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). "A biological sample" further refers to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from a multi-cellular organism, such as an animal, but the term "biological sample" can also refer to cells or tissue analyzed in vivo, i.e., without removal from the multi-cellular organism, or to cells propagated and/or analyzed in vitro, which may or may not stem from a multi-cellular organism, e.g., bacterial cells. Typically, a "biological sample" will contain cells from the animal, but the term can also refer to non-cellular biological material, such as non-cellular fractions of blood, saliva, or urine, that can be used to measure a disease-associated polynucleotide or polypeptide levels. "A biological sample" further refers to a medium, such as a nutrient broth or gel in which an organism has been propagated, which contains cellular components, such as proteins or nucleic acid molecules.

As used herein, the term "subject" refers to an organism to which the nucleic acid molecules of the invention can be administered. In one embodiment, a subject is a mammal (such as a mouse, rat, human, or nonhuman primate) or mammalian cells. In another embodiment, a subject is a human or human cells.

"Introducing into" means facilitating uptake or absorption into a cell, as is understood by those skilled in the art. Absorption or uptake of dsRNA can occur through unaided diffusive or cellular processes, or by means of auxiliary agents or devices, such as viral and synthetic vectors. For example, for introduction of dsRNA into cells in vivo, dsRNA can be injected into a tissue site or administered systemically. Introduction of dsRNA into cells in vitro includes methods known in the art such as electroporation and lipofection.

As used herein, a "nucleotide overhang" refers to the unpaired nucleotide or nucleotides that protrude from the duplex structure when a 3'-end of one RNA strand extends beyond the 5'-end of the other complementary strand, or vice versa. "3'-blunt"- or "5'-blunt" or "blunt end" means that there are no unpaired nucleotides at that end of the dsRNA, i.e., no nucleotide overhang. A "blunt ended" dsRNA is a dsRNA that is double stranded over its entire length, i.e., no nucleotide overhang at either end of the molecule.

The term "terminal base pair," as used herein, means the last nucleotide base pair on one end of the duplex region of the dsRNA. Thus, where the dsRNA is blunt ended (i.e., has no nucleotide overhangs), the last nucleotide base pairs at both ends of the dsRNA are terminal base pairs. Where a dsRNA has a nucleotide overhang at one or both ends of the duplex structure, the last nucleotide base pair(s) immediately adjacent the nucleotide overhang(s) is(are) the terminal base pair(s) at that end(s) of the dsRNA.

The term "position" with respect to a nucleotide forming part of an oligonucleotide refers to the relative position of the nucleotide within the oligonucleotide, counting all nucleotides in integers from the 5'-end of the oligonucleotide, position 1 being the 5'-terminal nucleotide. For example, the oligonucleotide 5'-aucg-3' comprises an adenosine monophosphate in position 1, uridine monophosphate in position 2, cytidine monophosphate in position 3, and guanosine monophosphate in position 4.

The term "sequence motif" or "sequence context", as used herein, refers to a certain nucleotide sequence of at least 2 nucleotides comprised in a larger oligonucleotide sequence. A sequence motif may occur once in an oligonucleotide sequence, or it may occur any number of times. For example, the oligonucleotide 5'-aucaucaug-3' comprises three occurrences of the sequence motif 5'-au-3', two occurrences of the sequence motifs 5'-uc-3' and 5'-ca-3', and one occurrence of the sequence motif 5'-ug-3'.

2. Double-stranded Ribonucleic Acids (dsRNA) with Improved Stability in Biological Samples In one embodiment, the invention relates to a double-stranded ribonucleic acid (dsRNA) having improved resistance to chemical and/or nuclease digestion, and thus increased stability in biological samples and a longer in vivo half-life. Increasing the in vivo half-life of the dsRNA results in enhanced bioavailability, and hence improved effectiveness in inhibiting expression or activity of a target gene. Thus, the present invention is based, at least in part, on improving the efficiency of dsRNA as a therapeutic agent, by increasing the stability in biological samples of the dsRNA, while maintaining the ability of the dsRNA to mediate RNA interference in vivo.

The dsRNA of the present invention comprises at least one substituted or modified nucleotide that enhances the stability in biological samples of the dsRNA compared to an identical dsRNA that recognizes the same target sequence but that lacks the substituted or modified nucleotide. As discussed below, the substituted or modified nucleotide is strategically located within the dsRNA for optimal stability, yet having little or no effect on interference activity. The dsRNA of the present invention may further comprise at least one phosphorothioate internucleoside linkage that preferably enhances the stability in biological samples of the dsRNA. As discussed in detail below, the dsRNA can be synthesized by standard methods known in the art, e.g., using an automated DNA synthesizer, such as those commercially available from Biosearch, Applied Biosystems, Inc., or other manufacturers known to the skilled person.

The present invention is based, in part, on the discovery that dsRNA molecules modified to contain at least one of 2'-modified uridines in all occurrences of the sequence motif 5'-uridine-adenine-3' (5'-ua-3'), or 2'-modified uridines in all occurrences of the sequence motif 5'-uridine-guanine-3' (5'-ug-3'), or 2'-modified cytidines in all occurrences of the sequence motif 5'-cytidine-adenine-3' (5'-ca-3'), or 2'-modified 5'-most uridines in all occurrences of the sequence motif 5'-uridine-uridine-3' (5'-uu-3'), or 2'-modified 5'-most cytidines in all occurrences of the sequence motif 5'-cytidine-cytidine-3' (5'-cc-3'), or 2'-modified cytidines in all occurrences of the sequence motif 5'-cytidine-uridine-3' (5'-cu-3'), or 2'-modified uridines in all occurrences of the sequence motif 5'-uridine-cytidine-3' (5'-uc-3'), have significantly enhanced stability in biological samples. Thus, for example, all uridines in the sequence context 5'-uridine-adenine-3' (5'-ua-3') can be replaced with 2'-O-methyl uridines to increase the stability of a dsRNA as compared to the stability of a corresponding dsRNA comprising unmethylated uridine (2'-OH). Furthermore, the inventors have found it to be particularly advantageous to replace all uridines and cytidines in sequence contexts 5'-ua-3', 5'-ug-3', 5'-uu-3', and 5'-ca-3'. The present inventors have discovered that incorporation of a, for example, 2'-O-methyl modification into a dsRNA comprising certain sequence motifs particularly prone to enzymatic cleavage significantly enhances the stability as compared to the corresponding unmodified dsRNA.

Cleavage of RNA or dsRNA by nucleolytic enzymes requires the formation of an enzyme-substrate complex, i.e., a particular nuclease-oligonucleotide complex. The nucleases generally require specific binding sites on the oligonucleotide for appropriate attachment. If the binding sites are removed or blocked, such that the nucleases are unable to attach to the oligonucleotide, the oligonucleotide will become nuclease resistant. This concept is well established particularly for the protection of oligonucleotides from degradation of exonucleases, enzymes that degrade oligonucleotides exclusively from their ends.

Figure 2:
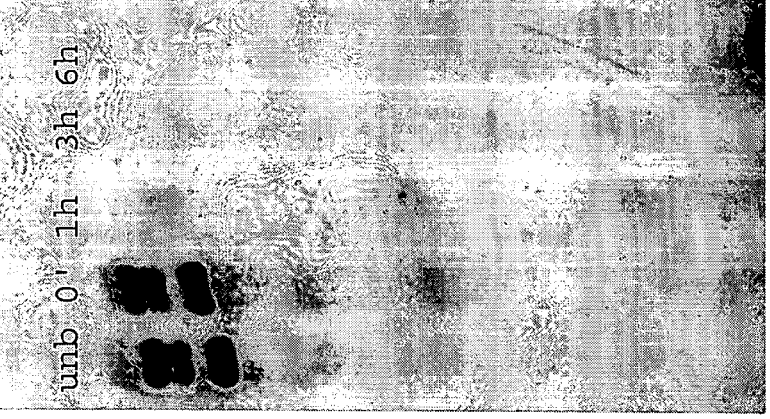
FIG. 2 shows a gel electrophoretic separation, stained using the "stains all" reagent, of the dsRNA referred to herein as AL-DP-5437 untreated (unb) or treated by incubation with human serum for 0, 1, 3, or 6 hours. AL-DP-5437 is identical in nucleotide sequence to AL-DP-5048, except that is bears phosphorothioate linkages between positions 20 an 21 of the sense strand, and between positions 21 and 22, as well as between 22 and 23, of the antisense strand, protecting this dsRNA against exonucleolytic attack.
Figure 1:
FIG. 1 shows a gel electrophoretic separation, stained using the "stains all" reagent, of the dsRNA referred to herein as AL-DP-5048 untreated (unb) or treated by incubation with human serum for 0, 1, 3, or 6 hours. AL-DP-5048 is an all-ribonucleic acid bearing no 2'-modifications or phosphorothioates.
Figure 4:
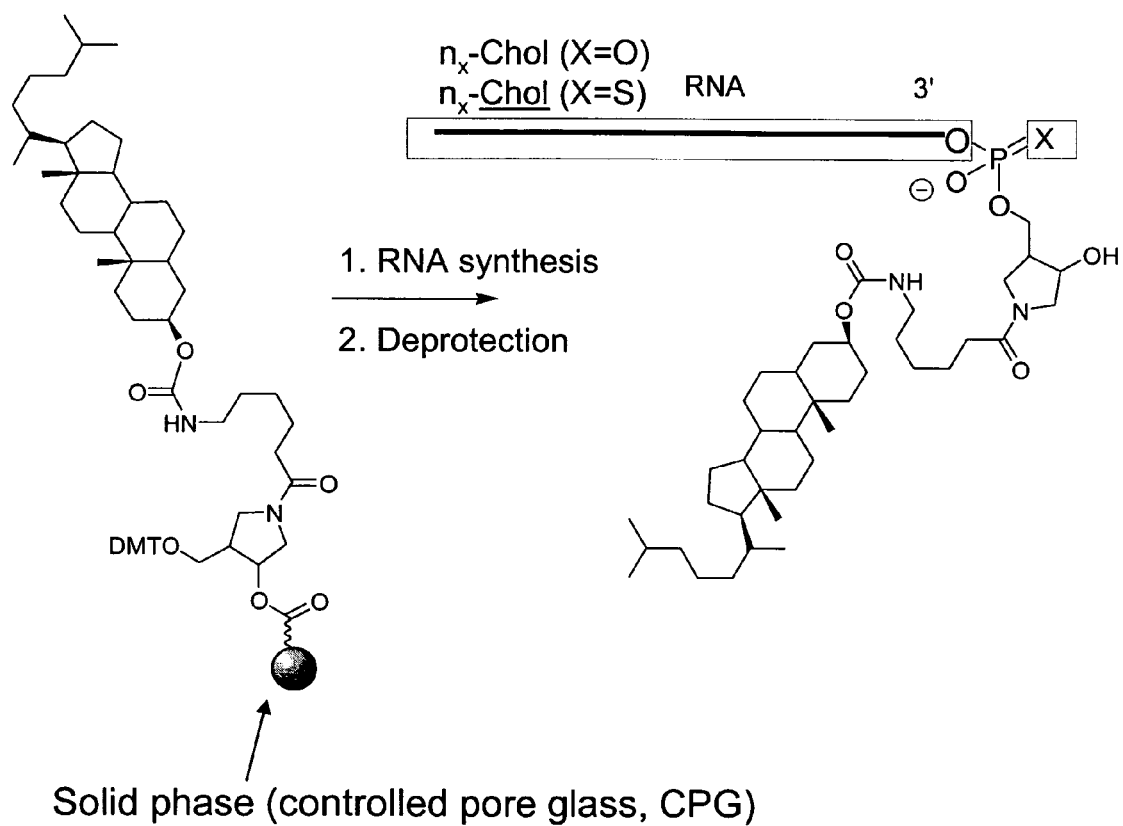
FIG. 4 shows the synthesis and structure of RNA strands conjugated to a cholesteryl moiety as described herein.
Figure 7:
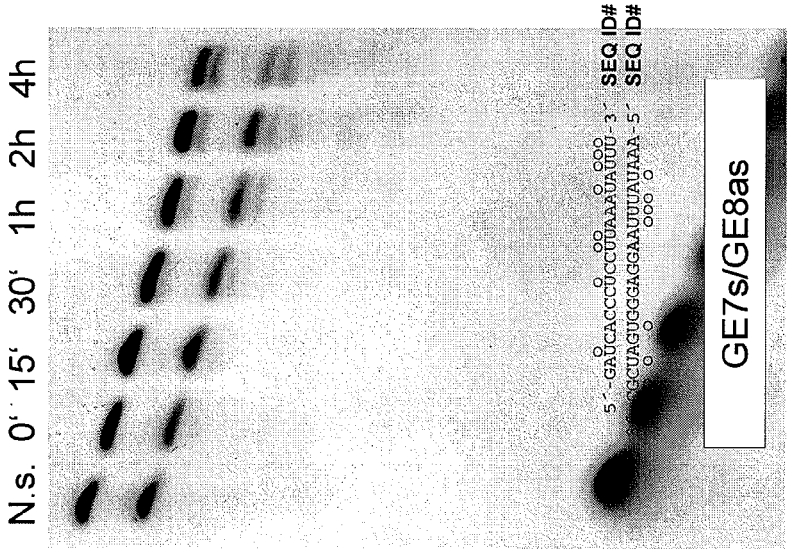
FIG. 7 shows a gel electrophoretic separation, stained using the "stains all" reagent, of a nuclease resistant dsRNA of the present invention (referred to as "GE7s/GE8as") after 0, 15, 30, 60, 120 and 240 minutes of incubation in serum.
Figure 6:
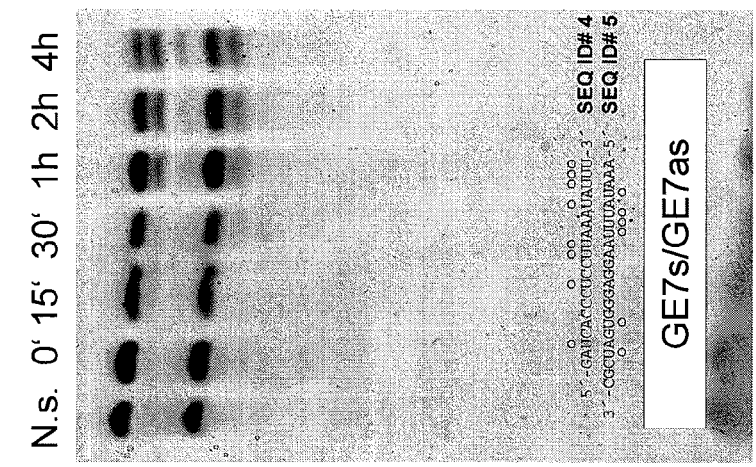
FIG. 6 shows a gel electrophoretic separation, stained using the "stains all" reagent, of a nuclease resistant dsRNA of the present invention (referred to as "GE7s/GE7as") after 0, 15, 30, 60, 120 and 240 minutes of incubation in serum.

The skilled person is well aware that incorporation of, for example, 2'-modified nucleotides, e.g. 2'-O-methylated nucleotides, at, or phosphorothioate linkages between, the two or three 3'-most and/or 5'-most, but particularly 3'-most, nucleotide positions of an oligonucleotide has been shown to be an efficient means for protection against exonucleolytic degradation. However, the present inventors have found that protection against exonucleolytic degradation is not sufficient to confer to a dsRNA the desired stability in biological samples. A dsRNA that is protected from exonucleolytic attack is still degraded quickly in biological samples by the action of omnipresent endonucleolytic enzymes. For example, FIG. 1, FIG. 2, and FIG. 3 show, respectively, the incubation of one unmodified dsRNA, a dsRNA protected against exonucleolytic attack by incorporation of phosphorothioate linkages between the 3'-terminal nucleotides, and a dsRNA that bears, in addition to phosphorothioate linkages between the 3'-terminal nucleotides, 2'-O-mthyl modifications in all occurrences of certain sequence motifs found particularly prone to endonucleolytic attack, namely 5'-ua-3', 5'-ug-3', 5'-uu-3', and 5'-ca-3'. The figures aptly demonstrate that only the latter survives to any measurable amount beyond 1 hour incubation in human serum.

The incorporation of 2'-modified non-terminal nucleotides has been reported to increase the stability of the modified dsRNA by increasing its resistance to nucleases, see Chiu, Y. L., and Rana, T. M., *RNA* (2003), 9:1034-1048, Braasch, D. A., et al.,. *Biochemistry* (2003), 42:7967-7975, Czauderna, F., et al., *Nucleic Acids Research* (2003), 31:2705-2716, and McSwiggen et al., WO 03070918. However, no rationale is given in the prior art for the incorporation of 2'-modified nucleotides, nor any algorithm for the design of nuclease resistant dsRNAs, other than the modification of every, or every other, or of every pyrimidine-comprising, nucleotide in a dsRNA. In addition, some reports show that the gene expression inhibiting activity of a dsRNA in mammalian cells is increasingly compromised by the incorporation of increasing numbers of 2'-modified nucleotides. This is consistent with studies in *Drosophila melanogaster*, which show that the complete substitution of all nucleotides with 2'-O-alkyl modifications abolished RNA interference activity (see Elbashir, S. M., et al., *EMBO J.* (2001) 20:6877-6888), as well as with the findings of the present inventors. Thus, there is a need for a design method yielding the sites of modifications with maximum effect in stabilizing a specific dsRNA towards degradation, while minimizing the overall number of modifications in order to preserve activity. The identification of sites particularly prone to enzymatic cleavage by the instant inventors enables such a method.

The present inventors have discovered that the location of a 2'-modification within a dsRNA has a significant influence on its stabilizing effect. As shown in the examples herein, the stabilizing effect of the incorporation of a 2'-O-methyl uridine is sequence specific, with the most significant effect being observed in the context of a 5'-uridine-adenine-3' (5'-ua-3') dinucleotide. Whereas the uridines in a 5'-ua-3' sequence context are vulnerable to endonucleolytic attack, the uridines in 5'-AU-3' sequence context are not. Finally, as evidenced by the data presented herein, the 2'-modifications must be present in both strands of the modified dsRNA for optimal nuclease resistance.

Similar findings were obtained for the dinucleotides 5'-uridine-guanine-3' (5'-ug-3'), 5'-cytidine-adenine-3' (5'-ca-3'), 5'-uridine-uridine-3' (5'-uu-3'), 5'-cytidine-cytidine-3' (5'-cc-3'), 5'-uridine-cytidine-3' (5'-uc-3'), and 5'-cytidine-uridine-3' (5'-cu-3'). Particularly, it was found that it was possible to design a dsRNA with a desired degree of stability by stepwise modification of uridines and cytidines present in the above sequence contexts, e.g, in a given siRNA having low stability in biological samples, by replacing in one step all uridines in a 5'-ua-3' sequence context by 2'-modified uridines, and in an optional further step, replacing all uridines in a 5'-ua-3' sequence context and all cytidines in a 5'-ca-3' sequence context by the respective 2'-modified nucleotides, and, in an optional further step, replacing all uridines in a 5'-ua-3' sequence context and all cytidines in a 5'-ca-3' sequence context and all uridines in a 5'-ug-3' by the respective 2'-modified nucleotides, and, in an optional further step, replacing all uridines in a 5'-ua-3' sequence context and all cytidines in a 5'-ca-3' sequence context and all uridines in a 5'-ug-3' and all uridines in a 5'-uu-3" sequence context by the respective 2'-modified nucleotides, and, in an optional further step, replacing all uridines in a 5'-ua-3' sequence context and all cytidines in a 5'-ca-3' sequence context and all uridines in a 5'-ug-3' and all uridines in a 5'-uu-3' sequence context and all cytidines in a 5'-cc-3' sequence context by the respective 2'-modified nucleotides, and, in an optional further step, replacing all uridines in a 5'-ua-3' sequence context and all cytidines in a 5'-ca-3' sequence context and all uridines in a 5'-ug-3' and all uridines in a 5'-uu-3' sequence context and all cytidines in a 5'-cc-3' sequence context and all uridines in a 5'-uc-3' sequence context by the respective 2'-modified nucleotides, and, in an optional further step, replacing all uridines in a 5'-ua-3' sequence context and all cytidines in a 5'-ca-3' sequence context and all uridines in a 5'-ug-3' and all uridines in a 5'-uu-3' sequence context and all cytidines in a 5'-cc-3' sequence context and uridines in a 5' -uc-3' sequence context and all cytodines in a 5'-cu-3' by the respective 2'-modified nucleotides, wherein, after each step, the stability of the modified dsRNA(s) in biological samples is determined.

The modified dsRNA of the present invention may be further stabilized by the presence of at least one phosphorothioate internucleoside linkage. The present inventors have discovered that replacing a phosphorus linkage with a phosphorothioate bond further increases the nuclease resistance of the modified dsRNA. Not all of the phosphodiester bonds of the dsRNA need be replaced with phosphorothioate linkages. Although the phosphorothiate bond(s) may be located anywhere within the modified dsRNA, the placement of the phosphorothioate bonds at specific locations has a substantial effect on stability. Specifically, the present inventors have discovered that incorporation of a phosphorothioate bond near the ends of the dsRNA, and particularly in the nucleotide overhang(s), has the most pronounced effect on nuclease resistance.

Thus, in another embodiment, the modified dsRNA comprises at least one phosphorothioate linkage, and preferably at least one phosphorothioate linkage on each strand. In a preferred embodiment, the dsRNA contains multiple phosphorothioate linkages on both RNA strands. The phosphorothioate linkage is preferably introduced at or near the ends of the modified dsRNA, and particularly in a nucleotide overhang. Moreover, when the modified dsRNA contains a string of contiguous or non-contiguous 2'-modified nucleotides, the dsRNA preferably contains at least one, and more preferably at least two, phosphorothioate linkages within the string of 2'-modified nucleotides.

In another embodiment, at least one end of the modified dsRNA is blunt. dsRNA with at least one blunt end show improved stability as compared to dsRNA having two nucleotide overhangs. dsRNA with at least one blunt end shows greater in vivo stability (i.e., is more resistant to degradation in the blood, plasma, and cells). However, dsRNA having at least one nucleotide overhang have superior inhibitory properties than their blunt-ended counterparts. The presence of only one nucleotide overhang strengthens the interference activity of the dsRNA, without effecting its overall stability. dsRNA having only one overhang has proven particularly effective in vivo (as well as in a variety of cells, and cell culture mediums), and are more stable than dsRNA having two blunt ends. The single-stranded nucleotide overhang may be 1 to 20, preferably 1 to 10, more preferably 1 to 5, and most preferably 1 or 2, nucleotides in length. Preferably, the single-stranded overhang is located at the 3'-end of the antisense RNA strand. When the nucleotide overhang is 2 nucleotides in length, the sequence of the 3'-end of the antisense RNA strand is preferably 5'-GC-3! or 5'-CGC-3'. In another preferred embodiment, the nucleotide overhang is at the 3'-end of the antisense RNA strand, and the 5'-end is blunt. In a particularly preferred embodiment, the sequence of the 3'-end of the antisense RNA strand is preferably 5'-GC-3' or 5'-CGC-3', wherein the phosphodiester bonds within and adjacent to the overhang are replaced with phosphorothioate linkages.

As described in co-pending U.S. Application Ser. No. 60/479,354, filed Jun. 18, 2003, which is hereby incorporated in its entirety, the presence of a purine base on the nucleotide overhang immediately adjacent to the terminal base pair provides further resistance to degradation. Thus, the modified dsRNA comprises a nucleotide overhang, wherein the unpaired nucleotide adjacent to the terminal base pair is a purine base, such as guanine (G) or adenine (A).

In yet another embodiment, the modified dsRNA is chemically modified to further enhance its stability, i.e. increase resistance to nuclease degradation and/or strand dissociation. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. Preferably, the chemical groups that can be used to modify the dsRNA include, without limitation, methylene blue; bifunctional groups, preferably bis-(2-chloroethyl)amine; N-acetyl-N'-(p-glyoxylbenzoyl)cystamine; 4-thiouracil; and psoralen. In one preferred embodiment, the linker is a hexa-ethylene glycol linker. In this case, the dsRNA are produced by solid phase synthesis and the hexa-ethylene glycol linker is incorporated according to standard methods (e.g., Williams, D. J., and K. B. Hall, *Biochem.* (1996) 35:14665-14670). In a particular embodiment, the 5'-end of the antisense RNA strand and the 3'-end of the sense RNA strand are chemically linked via a hexa-ethylene glycol linker. Moreover, at least one nucleotide may be modified to form a locked nucleotide. A locked nucleotide contains a methylene bridge that connects the 2'-oxygen of ribose with the 4'-carbon of ribose. Oligonucleotides containing the locked nucleotide are described in Koshkin, A. A., et al., *Tetrahedron* (1998), 54: 3607-3630) and Obika, S. et al., *Tetrahedron Lett.* (1998), 39: 5401-5404). Introduction of a locked nucleotide into an oligonucleotide improves the affinity for complementary sequences and increases the melting temperature by several degrees (Braasch, D. A. and D. R. Corey, *Chem. Biol.* (2001), 8:1-7).

In still another embodiment, the present invention provides dsRNA having nucleotide sequences that are substantially identical or complementary to at least a portion of a target gene. 100% sequence identity, or complementarity, between the inhibitory dsRNA and the portion of the target gene is typically preferred. However, embodiments of the invention include modified dsRNA having at least 70%, or 85%, or 90% or 95% sequence identity/complemetarity to the target gene, as well as improved resistance to enzymatic degradation and/ or dissociation, are encompassed by the present invention.

3. Method of Identifying and/or Making Modified dsRNA Having Improved Stability

The invention further relates to a method to identify a dsRNA with increased stability in biological samples, comprising the steps of:
  (a) synthesizing a first dsRNA of the invention and a second dsRNA identical to the first dsRNA except that it does not comprise the 2'-modified nucleotides of the dsRNA of the invention, and
  (b) determining the stability of said first and said second dsRNA in a biological sample by contacting both under identical conditions with the biological sample, and monitoring their degradation,
whereby, where the first dsRNA is degraded less rapidly than the second dsRNA, a dsRNA with increased stability in biological samples is identified.

In order to determine the stability of a dsRNA in a biological sample, the dsRNA is first brought into contact with the biological sample for some time, or for various lengths of time. Subsequently, it is determined to what extent the dsRNA is still present, preferably in its full length form, or at least in a form that remains biologically active, i.e. able to inhibit the expression of its target gene.

To this purpose, the dsRNA may be analyzed while still in contact with the biological sample, for example by using a dsRNA labeled with a fluorescent or radioactive marker. Alternatively, the dsRNA and/or its degradation products are first isolated from the constituents of the biological sample, e.g. by extraction, precipitation, or filtering, and subsequently analyzed, for example, without limitation, by gel electrophoresis, mass spectrometry, capillary electrophoresis, or any other method known to the skilled person.

A number of non-limiting examples for methods to determine the stability of a given dsRNA in a biological sample are given hereinbelow.

The invention further relates to a method for making a dsRNA having improved stability in biological samples and hence improved bioavailability. The modified dsRNA of the invention can be isolated from cells, produced from a DNA template, or can be chemically synthesized using methods known in the art prior to alteration using the methods of the invention.

In one embodiment, the modified dsRNAs are chemically synthesized. A method for making a double-stranded RNA (dsRNA) with high stability in biological samples for inhibiting the expression of a target gene comprising according to the instant invention comprises one or more of the steps of:
  (a) selecting one or more nucleotide sequences of between 18 and 30 nucleotides in length from the nucleotide sequence of the mRNA resulting from the transcription of the target gene; and
  (b) synthesizing one or more dsRNAs, wherein one strand comprises a sequence complementary to one of the nucleotide sequences selected in a.; and
  (c) testing said one or more dsRNAs for their capability to inhibit the expression of the target gene in a biological sample; and
  (d) selecting one of the one or more dsRNAs of c. possessing the capability to inhibit the expression of the target gene in a biological sample; and
  (e) in the dsRNA selected in (d), identifying in the nucleotide sequences of the sense strand as well as the antisense strand all occurrences of the dinucleotides 5'-ua-3', 5'-ca-3', 5'-ug-3', 5'-uu-3', 5'-cc-3', 5'-uc-3' and 5'-cu-3'.
  (f) synthesizing a dsRNA, wherein the 5'-uridines and/or 5'-cytidines in all occurrences of at least one of the dinucleotides identified in e. is replaced by a 2'-modified uridine and/or cytidine, respectively.

5'-uridines and/or 5'-cytidines in at least two, three, four, five, or more than five of the dinucleotides identified in (e) may be replaced by 2'-modified uridines and/or cytidines, respectively. Four is particularly preferred, and the replacement in sequence motifs 5'-ua-3', 5'-ca-3', 5'-ug-3', and 5'-uu-3' is most preferred.

Another embodiment of the instant invention is a method to increase the nuclease resistance of a double stranded RNA (dsRNA), comprising the steps of
  (a) identifying in the nucleotide sequences of the sense strand as well as the antisense strand of the dsRNA one, preferably more than one, more preferably all occurrences of the dinucleotides 5'-ua-3', 5'-ca-3', 5'-ug-3', 5'-uu-3', 5'-cc-3', 5'-uc-3' and 5'-cu-3'; and
  (b) replacing at least one of the 5'-uridines and/or 5'-cytidines in the dinucleotides identified in (a) with a 2'-modified uridine and/or cytidine, respectively.

5'-uridines and/or 5'-cytidines in at least two, three, four, five, or more than five of the dinucleotides identified in (a)

may be replaced by 2'-modified uridines and/or cytidines, respectively. Four is particularly preferred, and the replacement in sequence motifs 5'-ua-3', 5'-ca-3', 5'-ug-3', and 5'-uu-3' is most preferred.

The above methods may be carried out stepwise, for example wherein (a) in one step, all uridines in a 5'-ua-3' sequence context are replaced by 2'-modified uridines in addition to replacements performed in a previous step, and, (b) in an optional further step, all uridines in a 5'-ua-3' sequence context and all cytidines in a 5'-ca-3' sequence context are replaced by the respective 2'-modified nucleotides, and, (c) in an optional further step, all uridines in a 5'-ua-3' sequence context and all cytidines in a 5'-ca-3' sequence context and all uridines in a 5'-ug-3' are replaced by the respective 2'-modified nucleotides, and, (d) in an optional further step, all uridines in a 5'-ua-3' sequence context and all cytidines in a 5'-ca-3' sequence context and all uridines in a 5'-ug-3' and all uridines in a 5'-uu-3' sequence context are replaced by the respective 2'-modified nucleotides, and (e) in an optional further step, all uridines in a 5'-ua-3' sequence context and all cytidines in a 5'-ca-3' sequence context and all uridines in a 5'-ug-3' and all uridines in a 5'-uu-3' sequence context and all cytidines in a 5'-cc-3' sequence context are replaced by the respective 2'-modified nucleotides, and, (f) in an optional further step, all uridines in a 5'-ua-3' sequence context and all cytidines in a 5'-ca-3' sequence context and all uridines in a 5'-ug-3' and all uridines in a 5'-uu-3' sequence context and all cytidines in a 5'-cc-3' sequence context and all uridines in a 5'-uc-3' sequence context are replaced by the respective 2'-modified nucleotides, and, (g) in an optional further step, all uridines in a 5'-ua-3' sequence context and all cytidines in a 5'-ca-3' sequence context and all uridines in a 5'-ug-3' and all uridines in a 5'-uu-3' sequence context and all cytidines in a 5'-cc-3' sequence context and uridines in a 5'-uc-3' sequence context and all cytodines in a 5'-cu-3' are replaced by the respective 2'-modified nucleotides, wherein at least one of steps (a) through (g) is actually performed and wherein, after each step, the stability of the modified dsRNA(s) in biological samples is determined.

The skilled person will readily understand how to modify the above methods for dsRNAs lacking an occurrence of one of the above sequence contexts.

Preferably, at least four of the steps (a) through (g) are actually performed, and more preferably the steps (a), (b), (c), and (d) are first performed in this order. However, it is also within the scope of the instant invention to switch the various sequence motifs in the steps (a) through (g) of the stepwise methods according to the invention. For example, without limitation, rather than first replacing all uridines in a 5'-ua-3' sequence context by 2'-modified uridines, then replacing all uridines in a 5'-ua-3' sequence context and all cytidines in a 5'-ca-3' sequence context, and then replacing all uridines in a 5'-ua-3' sequence context and all cytidines in a 5'-ca-3' sequence context and all uridines in a 5'-ug-3', the stepwise method could be performed by first replacing all cytidines in a 5'-ca-3' sequence context, then replacing all cytidines in a 5'-ca-3' sequence context and all 5'-most uridines in 5'-uu-3' sequence context, and finally replacing all 5'-ca-3' and all 5'-most uridines in 5'-uu-3' sequence context and all uridines in a 5'-ug-3' sequence context.

In general, the oligonucleotides of the present invention can be synthesized using protocols known in the art, for example, as described in Caruthers, et al., *Methods in Enzymology* (1992) 211:3-19; Thompson, et al., International PCT Publication No. WO 99/54459; Wincott, et al., *Nucl. Acids Res.* (1995) 23:2677-2684; Wincott, et al., *Methods Mol. Bio.*, (1997) 74:59; Brennan, et al., *Biotechnol. Bioeng.* (1998) 61:33-45; and Brennan, U.S. Pat. No. 6,001,311; each of which is hereby incorporated by reference in its entirety herein. In general, the synthesis of oligonucleotides involves conventional nucleic acid protecting and coupling groups, such as dimethoxytrityl at the 5'-end, and phosphoramidites at the 3'-end. In a non-limiting example, small scale syntheses are conducted on a Expedite 8909 RNA synthesizer sold by Applied Biosystems, Inc. (Weiterstadt, Germany), using ribonucleoside phosphoramidites sold by ChemGenes Corporation (Ashland, Mass., USA). Alternatively, syntheses can be performed on a 96-well plate synthesizer, such as the instrument produced by Protogene (Palo Alto, Calif., USA), or by methods such as those described in Usman, et al., *J. Am. Chem. Soc.* (1987) 109:7845;-Scaringe, et al., *Nucl. Acids Res.* (1990) 18:5433; Wincott, et al., *Nucl. Acids Res.* (1990) 23:2677-2684; and Wincott, et al., *Methods Mol. Bio.* (1997) 74:59, each of which is hereby incorporated by reference in its entirety.

The nucleic acid molecules of the present invention may be synthesized separately and joined together post-synthetically, for example, by ligation (Moore, et al., *Science* (1992) 256: 9923; Draper, et al., International PCT publication No. WO 93/23569; Shabarova, et al., *Nucl. Acids Res.* (1991) 19:4247; Bellon, et al., *Nucleosides & Nucleotides* (1997) 16:951; and Bellon, et al., *Bioconjugate Chem.* (1997) 8:204; or by hybridization following synthesis and/or deprotection. The nucleic acid molecules can be purified by gel electrophoresis using conventional methods or can be purified by high pressure liquid chromatography (HPLC; see Wincott et al., supra, the totality of which is hereby incorporated herein by reference) and re-suspended in water.

In one embodiment, the method of making a modified dsRNA includes substituting at least one uridine or cytidine phosphoramidite with the corresponding 2'-O-methyl uridine or 2'-O-methyl cytidine phosphoramidite. In this embodiment, standard uridine or cytidine phosphoramidites are replaced with 2'-O-methyl uridine or 2'-O-methyl cytidine phosphoramidites during the synthetic process. Phosphorothioate dinucleotide linkages are introduced by substituting an iodine oxidizer solution with a solution of the Beaucage reagent (*J. Am. Chem. Soc.* (1990) 12:1253) or, for example, with EDITH (3-ethoxy-1,2,4-dithiazoline-5-one; Xu et al., Nucleic Acids Research 1996, 24:3643-3644). In addition, additional nucleotides containing G and C bases may be inserted so as to produce appropriately placed G-C base pairs, i.e., positioned to form a terminal nucleotide base pairs or to produce G-C base pairs within the four consecutive terminal nucleotides of the duplex structure.

In another embodiment, at least one nucleotide of the dsRNA is chemically modified to introduce chemical moieties or other structural features that differ from those seen in naturally occurring RNA. Such modifications may affect the ability of a base to hydrogen bond with its normal complementary base, and include, without limitation, heterocyclic derivatives, nucleotide analogs, covalent modifications such as the introduction of modified nucleotides, or the inclusion of pendant groups that are not naturally found in RNA molecules. Exemplary modifications and methods for introducing such modifications into dsRNA are known in the art, including those modifications and methods discussed in Section II above and the references cited therein.

In other embodiments, dsRNA is isolated from cells or produced from a DNA template prior to alteration using methods known in the art. In these alternate embodiments, the stability of the dsRNA can be increased prior to use by any of a number of well-known techniques, including those discussed above.

4. Methods to Inhibit the Expression of a Gene

In another aspect, the present invention relates to a method for inhibiting the expression of a target gene in a cell, comprising the steps of introducing a dsRNA of the invention into the cell, and maintaining the cell for a time sufficient to obtain inhibition of expression of the target gene in the cell, wherein methods of treatment or diagnosis to be performed on a human or animal body are excluded. The cell may be a mammalian cell.

The dsRNA may be directly introduced into the cell (i.e., intracellularly); or introduced extracellularly into a cavity, interstitial space, into the circulation of an organism, introduced orally, or may be introduced by bathing an organism in a solution containing the dsRNA. Methods for oral introduction include direct mixing of the dsRNA with food of the organism. Physical methods of introducing nucleic acids, for example, injection directly into the cell or extracellular injection into the organism, may also be used. Physical methods of introducing nucleic acids include injection of a solution containing the dsRNA, bombardment by particles covered by the dsRNA, soaking the cell or organism in a solution of the dsRNA, or electroporation of cell membranes in the presence of the dsRNA. Other methods known in the art for introducing nucleic acids to cells may be used, such as lipid-mediated carrier transport, chemical-mediated transport, such as calcium phosphate, and the like. Thus the dsRNA may be introduced along with components that perform one or more of the following activities: enhance dsRNA uptake by the cell, stabilize the annealed strands, or otherwise increase inhibition of the target gene.

The present invention may be used to reduce the activity of the target gene in a cell, for example, without limitation, for the analysis of the function of the target gene. Alternatively, the method may be used to test the effect of a second agent, e.g a small molecule, co-administered with the dsRNA, on the cell, under conditions of reduced expression of the target cell. In another embodiment, the invention is used for cosmetic purposes, for example to reduce the expression of a gene promoting unwanted hair growth, hair loss, coloring of the skin, callous formation, or to reduce the expression of a gene preventing or reducing muscle formation.

5. Pharmaceutical Compositions Comprising dsRNA

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier or diluent for administration of a therapeutic agent. Pharmaceutically acceptable carriers for therapeutic use are well known in the pharmaceutical art, and are described, for example, in *Remington's Pharmaceutical Sciences*, Mack Publishing Co. (A. R. Gennaro, ed. 1985), which is hereby incorporated by reference herein. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid, or talc. If desired, the tablets may be coated with a material such as glyceryl monostearate or glyceryl distearate, to delay absorption in the gastrointestinal tract.

In one embodiment, the invention relates to a pharmaceutical composition comprising a modified dsRNA, as described in the preceding sections, and a pharmaceutically acceptable carrier, as described below. A pharmaceutical composition including the modified dsRNA is useful for treating a disease caused by expression of a target gene. In this aspect of the invention, the dsRNA of the invention is formulated as described below. The pharmaceutical composition is administered in a dosage sufficient to inhibit expression of the target gene.

The pharmaceutical compositions of the present invention are administered in dosages sufficient to inhibit the expression or activity of the target gene. Compositions comprising the dsRNA of the invention can be administered at surprisingly low dosages. A maximum dosage of 5 mg dsRNA per kilogram body weight per day may be sufficient to inhibit or completely suppress the expression or activity of the target gene.

In general, a suitable dose of modified dsRNA will be in the range of 0.01 to 5.0 milligrams per kilogram body weight of the recipient per day, preferably in the range of 0.1 to 2.5 milligrams per kilogram body weight of the recipient per day, more preferably in the range of 0.1 to 200 micrograms per kilogram body weight per day, and most preferably in the range of 0.1 to 100 micrograms per kilogram body weight per day. The pharmaceutical composition may be administered once per day, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the infection or disease, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNA encompassed by the invention can be made using conventional methodologies or on the basis of in vivo testing using an appropriate animal model, as described elsewhere herein.

Advances in mouse genetics have generated a number of mouse models for the study of various human diseases. For example, mouse repositories can be found at The Jackson Laboratory, Charles River Laboratories, Taconic, Harlan, Mutant Mouse Regional Resource Centers (MMRRC) National Network and at the European Mouse Mutant Archive. Such models may be used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), ocular, rectal, vaginal and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

For oral administration, the dsRNA useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that harbor the target gene or virus. Such substances include, for example, micellar structures, such as liposomes or capsids, as described below. Although microinjection, lipofection, viruses, viroids, capsids, capsoids, or other auxiliary agents are required to introduce dsRNA into cell cultures, surprisingly these methods and agents are not necessary for uptake of dsRNA in vivo. The dsRNA of the present invention are particularly advantageous in that they do not require the use of an auxiliary agent to mediate uptake of the dsRNA into the cell, many of which agents are toxic or associated with deleterious side effects. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions can also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

Toxicity and therapeutic efficacy of dsRNA can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. dsRNAs that exhibit high therapeutic indices are preferred.

The data obtained from cell culture assays and animal studies can be used in formulating a range of dosage for use in humans. The dosages of compositions of the invention are preferably within a range of circulating concentrations that include the ED50 with little or no toxicity. The dosage may vary within this range depending upon the dosage form employed and the route of administration utilized. For any dsRNA used in the method of the invention, the therapeutically effective dose can be estimated initially from cell culture assays. A dose may be formulated in animal models to achieve a circulating plasma concentration range of the dsRNA or, when appropriate, of the polypeptide product of a target sequence (e.g., achieving a decreased concentration of the polypeptide) that includes the IC50 (i.e., the concentration of the test dsRNA which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, dsRNAs relating to the invention can be administered in combination with other known agents effective in treating viral infections and diseases. In any event, the administering physician can adjust the amount and timing of dsRNA administration on the basis of results observed using standard measures of efficacy known in the art or described herein.

For oral administration, the dsRNA useful in the invention will generally be provided in the form of tablets or capsules, as a powder or granules, or as an aqueous solution or suspension.

6. Methods for Treating Diseases Caused by Expression of a Target Gene

In one embodiment, the invention relates to a method for treating a subject having a disease or at risk of developing a disease caused by the expression of a target gene. In this embodiment, dsRNAs can act as novel therapeutic agents for controlling one or more of cellular proliferative and/or differentiative disorders, disorders associated with bone metabolism, immune disorders, hematopoietic disorders, cardiovascular disorders, liver disorders, viral diseases, or metabolic disorders. The method comprises administering a pharmaceutical composition of the invention to the patient (e.g., a human), such that expression of the target gene is silenced. Because of their high efficiency and specificity, the dsRNA of the present invention specifically target mRNA of target genes of diseased cells and tissues, as described below, and at surprisingly low dosages. The pharmaceutical compositions are formulated as described in the preceding section, which is hereby incorporated by reference herein.

Examples of genes which can be targeted for treatment include, without limitation, an oncogene (Hanahan, D. and R. A. Weinberg, *Cell* (2000) 100:57; and Yokota, J., *Carcinogenesis* (2000) 21(3):497-503); a cytokine gene (Rubinstein, M., et al., *Cytokine Growth Factor Rev*. (1998) 9(2):175-81); a idiotype (Id) protein gene (Benezra, R., et al., *Oncogene* (2001) 20(58):8334-41; Norton, J. D., *J. Cell Sci.* (2000) 113(22):3897-905); a prion gene (Prusiner, S. B., et al., *Cell* (1998) 93(3):337-48; Safar, J., and S. B. Prusiner, *Prog. Brain Res.* (1998) 117:421-34); a gene that expresses molecules that induce angiogenesis (Gould, V. E. and B. M. Wagner, *Hum. Pathol.* (2002) 33(11):1061-3); adhesion molecules (Chothia, C. and E. Y. Jones, *Annu. Rev. Biochem.* (1997) 66:823-62; Parise, L. V., et al., *Semin. Cancer Biol.* (2000) 10(6):407-14); cell surface receptors (Deller, M. C., and Y. E. Jones, *Curr. Opin. Struct. Biol.* (2000) 10(2):213-9); genes of proteins that are involved in metastasizing and/or invasive processes (Boyd, D., *Cancer Metastasis Rev.* (1996) 15(1):77-89; Yokota, J., *Carcinogenesis* (2000) 21(3):497-503); genes of proteases a well as of molecules that regulate apoptosis and the cell cycle (Matrisian, L. M., *Curr. Biol.* (1999) 9(20): R776-8; Krepela, E., *Neoplasma* (2001) 48(5):332-49; Basbaum and Werb, *Curr Opin. Cell Biol.* (1996) 8:731-738; Birkedal-Hansen, et al., *Crit. Rev. Oral Biol. Med.* (1993) 4:197-250; Mignatti and Rifkin, *Physiol. Rev.* (1993) 73:161-195; Stetler-Stevenson, et al., *Annu. Rev. Cell Biol.* (1993) 9:541-573; Brinkerhoff, E., and L. M. Matrisan, *Nature Reviews* (2002) 3:207-214; Strasser, A., et al., *Annu. Rev. Biochem.* (2000) 69:217-45; Chao, D. T. and S. J. Korsmeyer, *Annu. Rev. Immunol.* (1998) 16:395-419; Mullauer, L., et al., *Mutat. Res.* (2001) 488(3):211-31; Foteda R., et al., *Prog. Cell Cycle Res.* (1996) 2:147-63; Reed, J. C., *Am. J Pathol.* (2000) 157(5):1415-30; D'Ari, R., *Bioassays* (2001) 23(7): 563-5); genes that express the EGF receptor; Mendelsohn, J. and J. Baselga, *Oncogene* (2000) 19(56):6550-65; Normanno, N., et al., *Front. Biosci.* (2001) 6:D685-707); and the multi-drug resistance 1 gene, MDR1 gene (Childs, S., and V. Ling, *Imp. Adv. Oncol.* (1994) 21-36).

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA substantially identical to all or part of a mutated gene associated with cancer, or one expressed at high levels in tumor cells, may be brought into contact with or introduced into a cancerous cell or tumor gene.

Examples of cellular proliferative and/or differentiative disorders include cancer, e.g., a carcinoma, sarcoma, metastatic disorder or hematopoietic neoplastic disorder, such as a leukemia. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state or condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplastic cells of hematopoietic origin, e.g., arising from myeloid, lymphoid or erythroid lineages, or precursor cells thereof.

The pharmaceutical compositions of the present invention can also be used to treat a variety of immune disorders, in particular those associated with overexpression or aberrant expression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

In another embodiment, the invention relates to methods for treating viral diseases, including but not limited to hepatitis C, hepatitis B, herpes simplex virus (HSV), HIV-AIDS, poliovirus, and smallpox virus. dsRNA of the invention are prepared as described herein to target expressed sequences of a virus, thus ameliorating viral activity and replication. The dsRNAs can be used in the treatment and/or diagnosis of viral infected tissue, both animal and plant. Also, such dsRNA can be used in the treatment of virus-associated carcinoma, such as hepatocellular cancer.

For example, the dsRNA of the present invention are useful for treating a subject having an infection or a disease associated with the replication or activity of a (+) strand RNA virus having a 3'-UTR, such as HCV. In this embodiment, the dsRNA can act as novel therapeutic agents for inhibiting replication of the virus. The method comprises administering a pharmaceutical composition of the invention to the patient (e.g., a human), such that viral replication is inhibited. Examples of (+) strand RNA viruses which can be targeted for inhibition include, without limitation, picornaviruses, caliciviruses, nodaviruses, coronaviruses, arteriviruses, flaviviruses, and togaviruses. Examples of picornaviruses include enterovirus (poliovirus 1), rhinovirus (human rhinovirus 1A), hepatovirus (hepatitis A virus), cardiovirus (encephalomyocarditis virus), aphthovirus (foot-and-mouth disease virus O), and parechovirus (human echovirus 22). Examples of caliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is the representative nodavirus. Coronaviruses include coronavirus (avian infections bronchitis virus) and torovirus (Berne virus). Arterivirus (equine arteritis virus) is the representative arteriviridus. Togavirises include alphavirus (Sindbis virus) and rubivirus (Rubella virus). Finally, the flaviviruses include flavivirus (Yellow fever virus), pestivirus (bovine diarrhea virus), and hepacivirus (hepatitis C virus). In a preferred embodiment, the virus is hepacivirus, the hepatitis C virus. Although the foregoing list exemplifies vertebrate viruses, the present invention encompasses the compositions and methods for treating infections and diseases caused by any (+) strand RNA virus having a 3'-UTR, regardless of the host. For example, the invention encompasses the treatment of plant diseases caused by sequiviruses, comoviruses, potyviruses, sobemovirus, luteoviruses, tombusviruses, tobavirus, tobravirus, bromoviruses, and closteroviruses.

The pharmaceutical compositions encompassed by the invention may be administered by any means known in the art including, but not limited to, oral or parenteral routes, including intravenous, intramuscular, intraperitoneal, subcutaneous, transdermal, airway (aerosol), ocular, rectal, vaginal, and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

7. Methods for Inhibiting Expression of a Target Gene

In yet another aspect, the invention relates to a method for inhibiting the expression of a target gene in a cell or organism. In one embodiment, the method comprises administering the inventive dsRNA or a pharmaceutical composition comprising the dsRNA to a cell or an organism, such as a mammal, such that expression of the target gene is silenced. Because of their surprisingly improved stability and bioavailability, the dsRNA of the present invention effectively inhibit expression or activity of target genes at surprisingly low dosages. Compositions and methods for inhibiting the expression of a target gene using dsRNA can be performed as described in the preceding sections, particularly Sections 4 and 5.

In this embodiment, a pharmaceutical composition comprising the dsRNA may be administered by any means known in the art including, but not limited to oral or parenteral routes, including intravenous, intramuscular, intraperitoneal, subcutaneous, transdermal, airway (aerosol), ocular, rectal, vaginal, and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

The methods for inhibiting the expression of a target gene can be applied to any gene one wishes to silence, thereby specifically inhibiting its expression, provided the cell or organism in which the target gene is expressed comprises the cellular machinery which effects RNA interference. Examples of genes which can be targeted for silencing include, without limitation, developmental genes including but not limited to adhesion molecules, cyclin kinase inhibitors, Wnt family members, Pax family members, Winged helix family members, Hox family members, cytokines/lymphokines and their receptors, growth/differentiation factors and their receptors, and neurotransmitters and their receptors; (2) oncogenes including but not limited to ABLI, BCL1, BCL2, BCL6, CBFA2, CBL, CSFIR, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES; (3) tumor suppresser genes including but not limited to APC, BRCA1, BRCA2, MADH4, MCC, NF1, NF2, RB1, TP53 and WT1; and (4) enzymes including but not limited to ACP desaturases and hydroxylases, ADP-glucose pyrophorylases, ATPases, alcohol dehydrogenases, amylases, amyloglucosidases, catalases, cellulases, cyclooxygenases, decarboxylases, dextrinases, DNA and RNA polymerases, galactosidases, glucanases, glucose oxidases, GTPases, helicases, hemicellulases, integrases, invertases, isomerases, kinases, lactases, lipases, lipoxygenases, lysozymes, pectinesterases, peroxidases, phosphatases, phospholipases, phosphorylases, polygalacturonases, proteinases and peptideases, pullanases, recombinases, reverse transcriptases, topoisomerases, and xylanases.

In addition to in vivo gene inhibition, the skilled artisan will appreciate that the dsRNA of the present invention are useful in a wide variety of in vitro applications. Such in vitro applications, include, for example, scientific and commercial research (e.g., elucidation of physiological pathways, drug discovery and development), and medical and veterinary diagnostics. In general, the method involves the introduction of the dsRNA into a cell using known techniques (e.g., absorption through cellular processes, or by auxiliary agents or devices, such as electroporation and lipofection), then maintaining the cell for a time sufficient to obtain degradation of an mRNA transcript of the target gene.

8. Methods for Identifying dsRNA Having Increased Stability

In yet another aspect, the invention relates to methods for identifying dsRNA having increased stability in biological tissues and fluids such as serum. dsRNA having increased stability have enhanced resistance to degradation, e.g., by chemicals or nucleases (particularly endonucleases) which normally degrade RNA molecules. Methods for detecting increases in nucleic acid stability are well known in the art. Any assay capable of measuring or detecting differences between a test dsRNA and a control dsRNA in any measurable physical parameter may be suitable for use in the methods of the present invention. In general, because the inhibitory effect of a dsRNA on a target gene activity or expression requires that the molecule remain intact, the stability of a particular dsRNA can be evaluated indirectly by observing or measuring a property associated with the expression of the gene. Thus, the relative stability of a dsRNA can be determined by observing or detecting (1) an absence or observable decrease in the level of the protein encoded by the target gene, (2) an absence or observable decrease in the level of mRNA product from the target gene, and (3) a change or loss in phenotype associated with expression of the target gene. In the context of a medical treatment, the stability of a dsRNA may be evaluated based on the degree of the inhibition of expression or function of the target gene, which in turn may be assessed based on a change in the disease condition of the patient, such as reduction in symptoms, remission, or a change in disease state.

In one embodiment, the method comprises preparing a dsRNA as described in Section III above (e.g., through chemical synthesis), incubating the dsRNA with a biological sample, then analyzing and identifying those dsRNA that exhibit an increased stability as compared to a control dsRNA.

In an exemplified embodiment, dsRNA is produced in vitro by mixing/annealing complementary single-stranded RNA strands, preferably in a molar ratio of at least about 3:7, more preferably in a molar ratio of about 4:6, and most preferably in essentially equal molar amounts (e.g., a molar ratio of about 5:5). Preferably, the single-stranded RNA strands are denatured prior to mixing/annealing, and the buffer in which the mixing/annealing reaction takes place contains a salt, preferably potassium chloride. Single-stranded RNA strands may be synthesized by solid phase synthesis using, for example, an Expedite 8909 synthesizer (Applied Biosystems, Applera Deutschland GmbH, Darmstadt, Germany), as described above.

dsRNA are incubated with a biological sample under the conditions sufficient or optimal for enzymatic function. After incubating with a biological sample, the stability of the dsRNA is analyzed by means conventional in the art, for example using RNA gel electrophoresis as exemplified herein. For example, when the sample is serum, the dsRNA may be incubated at a concentration of 1-10 µM, preferably 2-8 µM, more preferably 3-6 µM, and most preferably 4-5 µM. The incubation temperature is preferably between 25° C. and 45° C., more preferably between 35° C. and 40° C., and most preferably about 37° C.

The biological sample used in the incubation step may be derived from tissues, cells, biological fluids or isolates thereof. For example, the biological sample may be isolated from a subject, such as a whole organism or a subset of its tissues or cells. The biological sample may also be a component part of the subject, such as a body fluid, including but not limited to blood, serum, plasma, mucus, lymphatic fluid, synovial fluid, cerebrospinal fluid, saliva, amniotic fluid, amniotic cord blood, urine, vaginal fluid and semen. Preferably, the biological sample is a serum derived from a blood sample of a subject. The subject is preferably a mammal, more preferably a human or a mouse.

In another embodiment, the method includes selecting a dsRNA having increased stability by measuring the mRNA and/or protein expression levels of a target gene in a cell following introduction of the dsRNA. In this embodiment, a dsRNA of the invention inhibits expression of a target gene in a cell, and thus the method includes selecting a dsRNA that induces a measurable reduction in expression of a target gene as compared to a control dsRNA. Assays that measure gene expression by monitoring RNA and/or protein levels can be performed within about 24 hours following uptake of the dsRNA by the cell. For example, RNA levels can be measured by Northern blot techniques, RNAse Protection Assays, or Quality Control-PCR (QC-PCR) (including quantitative reverse transcription coupled PCR (RT-PCR)) and analogous methods known in the art. Protein levels can be assayed, for example, by Western blot techniques, flow cytometry, or reporter gene expression (e.g., expression of a fluorescent reporter protein, such as green fluorescent protein (GFP)). RNA and/or protein levels resulting from target gene expression can be measured at regular time intervals following introduction of the test dsRNA, and the levels are compared to those following introduction of a control dsRNA into cells. A control dsRNA can be a nonsensical dsRNA (i.e., a dsRNA having a scrambled sequence that does not target any nucleotide sequence in the subject), a dsRNA that can target a gene not present in the subject (e.g., a luciferase gene, when the dsRNA is tested in human cells), or a dsRNA otherwise previously shown to be ineffective at silencing the target gene. The mRNA and protein levels of the test sample and the control sample can be compared. The test dsRNA is selected as having increased stability when there is a measurable reduction in expression levels following absorption of the test dsRNA as compared to the control dsRNA. mRNA and protein measurements can be made using any art-recognized technique (see, e.g., Chiang, M.Y., et al., *J. Biol Chem.* (1991) 266:18162-71; Fisher, T, et al., *Nucl. Acids Res.* (1993) 21:3857; and Chen et al., *J. Biol. Chem.* (1996) 271:28259).

The ability of a dsRNA composition of the invention to inhibit gene expression can be measured using a variety of techniques known in the art. For example, Northern blot analysis can be used to measure the presence of RNA encoding a target protein. The level of the specific mRNA produced by the target gene can be measured, e.g., using RT-PCR. Because dsRNA directs the sequence-specific degradation of endogenous mRNA through RNAi, the selection methods of the invention encompass any technique that is capable of detecting a measurable reduction in the target RNA. In yet another example, Western blots can be used to measure the amount of target protein present. In still another embodiment, a phenotype influenced by the amount of the protein can be detected. Techniques for performing Western blots are well known in the art (see, e.g., Chen, et al., *J. Biol. Chem.* (1996) 271:28259).

When the target gene is to be silenced by a dsRNA that targets a promoter sequence of the target gene, the target gene can be fused to a reporter gene, and reporter gene expression (e.g., transcription and/or translation) can be monitored. Similarly, when the target gene is to be silenced by a dsRNA that targets a sequence other than a promoter, a portion of the target gene (e.g., a portion including the target sequence) can be fused with a reporter gene so that the reporter gene is transcribed. By monitoring a change in the expression of the reporter gene in the presence of the dsRNA, it is possible to determine the effectiveness of the dsRNA in inhibiting the expression of the reporter gene. The expression levels of the reporter gene in the presence of the test dsRNA versus a control dsRNA are then compared. The test dsRNA is selected as having increased stability when there is a measurable reduction in expression levels of the reporter gene as compared to the control dsRNA. Examples of reporter genes useful for use in the present invention include, without limitation, those coding for luciferase, GFP, chloramphenicol acetyl transferase (CAT), β-galactosidase, and alkaline phosphatase. Suitable reporter genes are described, for example, in *Current Protocols in Molecular Biology*, John Wiley & Sons, New York (Ausubel, F. A., et al., eds., 1989); Gould, S. J., and S. Subramani, *Anal. Biochem.* (1988) 7:404-408; Gorman, C. M., et al., *Mol. Cell. Biol.* (1982) 2:1044-1051; and Selden, R., et al., *Mol. Cell. Biol.* (1986) 6:3173-3179; each of which is hereby incorporated by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

1. dsRNA Synthesis

1.1 Source of Reagents

Where the source of a reagent is not specifically given herein, such reagent may be obtained from any supplier of reagents for molecular biology at a quality/purity standard for application in molecular biology.

1.2 siRNA Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

Cholesterol was conjugated to siRNA as illustrated in FIG. 1. For the synthesis of these 3'-cholesterol-conjugated siRNAs, an appropriately modified solid support was used for RNA synthesis. The modified solid support was prepared as follows:

1.2.1 Diethyl-2-azabutane-1,4-dicarboxylate AA

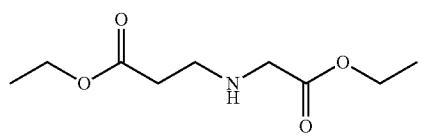

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

1.2.2 3-{Ethoxycarbonylmethyl-[6-(9H-fluoren-9-ylmethoxycarbonyl-amino)-hexanoyl]-amino}-propionic acid ethyl ester AB

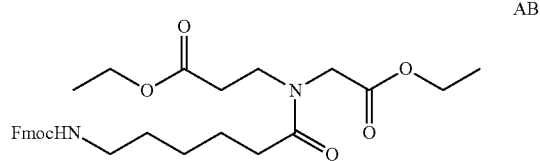

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

1.2.3 3-[(6-Amino-hexanoyl)-ethoxycarbonylmethyl-amino]-propionic acid ethyl ester AC

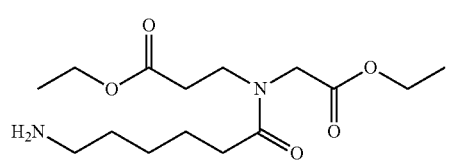

3-{Ethoxycarbonylmethyl-[6-(9H-fluoren-9-ylmethoxycarbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

1.2.4 3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethylamino)-propionic acid ethyl ester AD

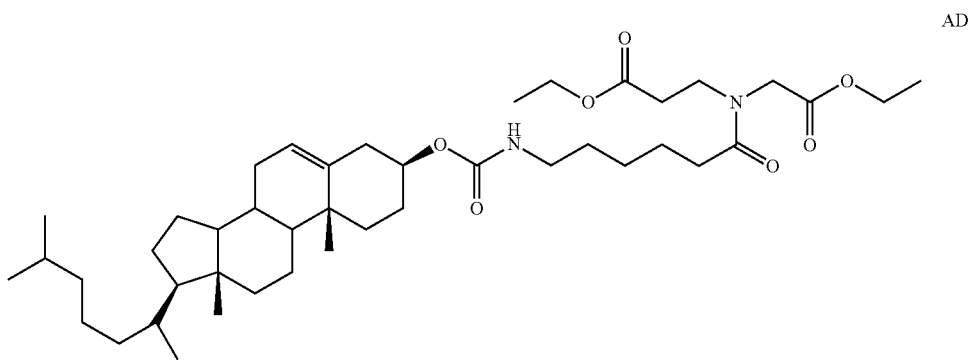

AD

The hydrochloride salt of 3-[(6-Amino-hexanoyl)-ethoxycarbonylmethyl-amino]-propionic acid ethyl ester AC (4.7 g, 14.8 mmol) was taken up in dichloromethane. The suspension was cooled to 0° C. on ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1.2.5 1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of $NaH_2PO_4 \cdot H_2O$ in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

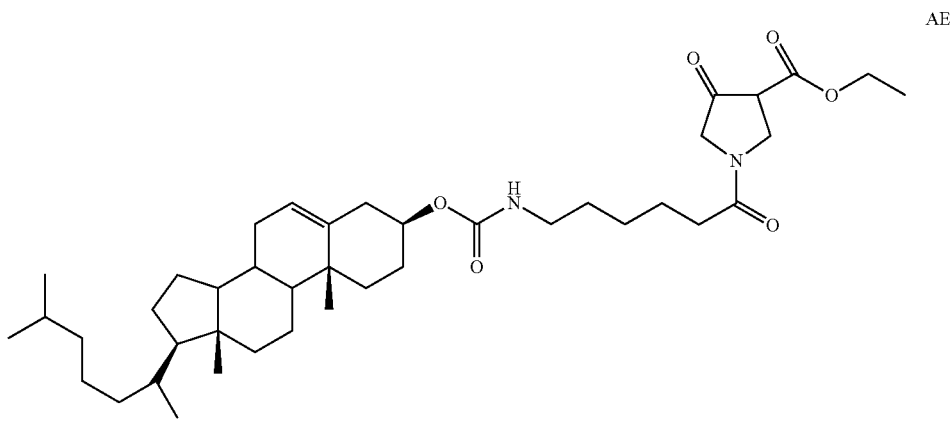

AE 1.2.6 [6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

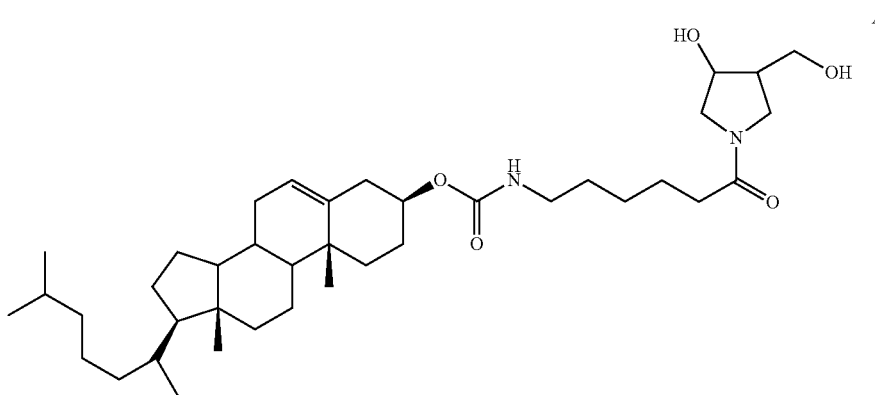

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl$_3$) (1.75 g, 95%).

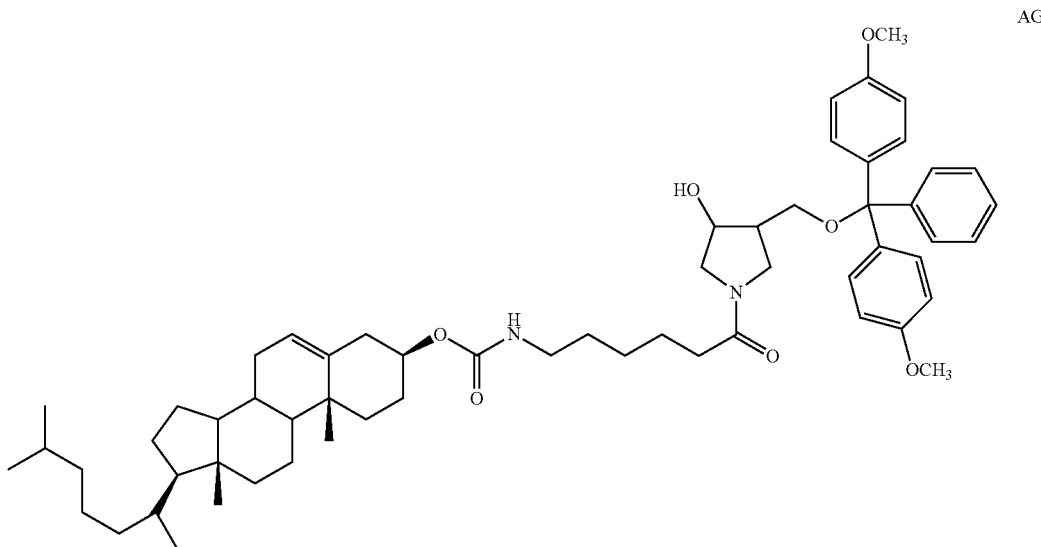

1.2.7 Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a] phenanthren-3-yloxycarbonylamino]-hexanoyl}-pyrrolidin-3-yl) ester AH

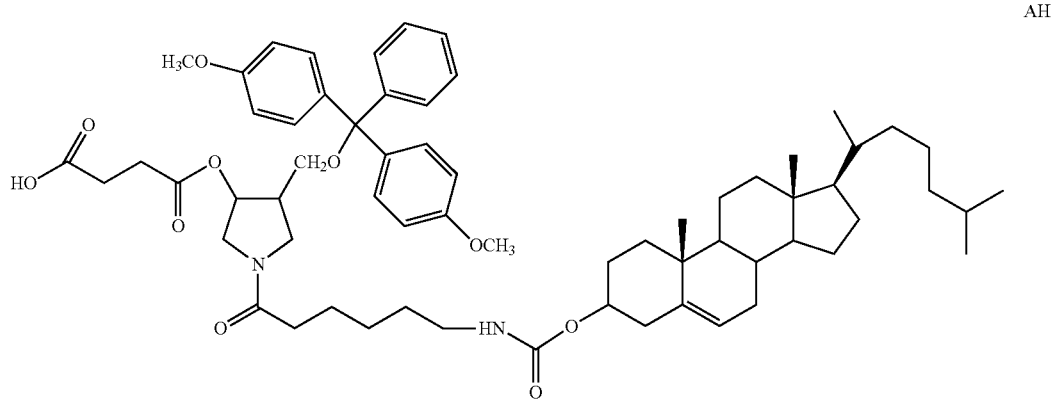

AH

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

1.2.8 Cholesterol derivatised CPG A1

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/pyridine. The achieved loading of the CPG was measured by taking UV measurement (37 mM/g).

The synthesis and structure of cholesterol conjugated RNA strands is illustrated in FIG. 1.

2. siRNA Agent Design and Selection

Nucleic acid sequences are represented below using standard nomenclature, and specifically the abbreviations of Table 1.

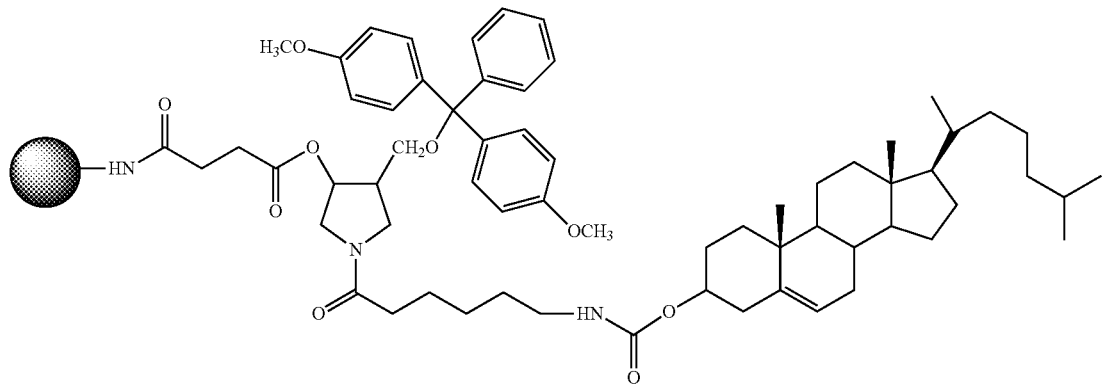

AI

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
|---|---|
| A, a | 2'-deoxy-adenosine-5'-monophosphate, adenosine-5'-monophosphate |
| C, c | 2'-deoxy-cytidine-5'-monophosphate, cytidine-5'-monophosphate |
| G, g | 2'-deoxy-guanosine-5'-monophosphate, guanosine-5'-monophosphate |
| T, t | 2'-deoxy-thymidine-5'-monophosphate, thymidine-5'-monophosphate |
| U, u | 2'-deoxy-uridine-5'-monophospate, uridine-5'-monophospate |
| N, n | any 2'-deoxy-nucleotide/nucleotide (G, A, C, or T, g, a, c or u) |
| am | 2'-O-methyladenosine-5'-monophospate |
| cm | 2'-O-methylcytidine-5'-monophospate |
| gm | 2'-O-methylguanosine-5'-monophospate |
| tm | 2'-O-methyl-thymidine-5'-monophospate |
| um | 2'-O-methyluridine-5'-monophospate |
| af | 2'-fluoro-2'-deoxy-adenosine-5'-monophospate |
| cf | 2'-fluoro-2'-deoxy-cytidine-5'-monophospate |
| gf | 2'-fluoro-2'-deoxy-guanosine-5'-monophospate |
| tf | 2'-fluoro-2'-deoxy-thymidine-5'-monophospate |
| uf | 2'-fluoro-2'-deoxy-uridine-5'-monophospate |
| <u>A</u>, <u>C</u>, <u>G</u>, <u>T</u>, <u>U</u>, <u>a</u>, <u>c</u>, <u>g</u>, <u>t</u>, <u>u</u> | underlined: nucleoside-5'-phosphorothioate |
| <u>am</u>, <u>cm</u>, <u>gm</u>, <u>tm</u>, <u>um</u> | underlined: 2'-O-methyl-nucleoside-5'-phosphorothioate |
| *A, C, G, T, U, a, c, g, t, u* | bold italic: 2'-deoxy-adenosine, 2'-deoxy-cytidine, 2'-deoxy-guanosine, 2'-deoxy-thymidine, 2'-deoxy-uridine, adenosine, cytidine, guanosine, thymidine, uridine (5'-hydroxyl) |
| *am, cm, gm, tm, um* | bold italic: 2'-O-methyl-adenosine, 2'-O-methyl-cytidine, 2'-O-methyl-guanosine, 2'-O-methyl-thymidine, 2'-O-methyl-uridine (5'-hydroxyl) |
| -tp | 2'- or 3'-terminal phosphate or 2'/3'-terminal cyclic phosphate |
| -Chol | 1-{6-[cholester-3-yloxycarbonylamino]-hexanoyl}-4-hydroxy-pyrrolidin-3-phosphorothioate diester |

[a] capital letters represent 2'-deoxyribonucleotides (DNA), lower case letters represent ribonucleotides (RNA)

Table 2 summarizes the sequences of the sense and antisense strands of a first group of double stranded RNAs tested for stability in human serum herein.

TABLE 2

Sequences of sense and antisense strands of a first group of double stranded RNAs tested for stability in human serum. All sequences are given 5' → 3'.

| Duplex Descriptor | Sense | SEQ ID NO: | Antisense | SEQ ID NO: |
|---|---|---|---|---|
| GE1s/GE1as | *g*aucacccuccuuaaauauuu | 2 | *u*ucuagugggaggaauuuauaaa | 3 |
| GE7s/GE7as | *g*aumcacccumccumumaaaumaumumum | 4 | *c*gcumagumgggaggaaumumumaumaaa | 5 |
| GE7s/GE8as | *g*aumcacccumccumumaaaumaumumum | 4 | *c*gmcmumagumgggaggaaumumumaumaaa | 6 |
| GE7s/GE9as | *g*aumcacccumccumumaaaumaumumum | 4 | *c*<u>gmcm</u>umagumgggaggaaumumumaumaaa | 7 |
| GE7s/GE10as | *g*aumcacccumccumumaaaumaumumum | 4 | *c*gmcmumagugggaggaauuumaumaaa | 8 |
| GE7s/GE11as | *g*aumcacccumccumumaaaumaumumum | 4 | *c*gmcmuagugggaggaaumuuaumaaa | 9 |
| GE1s/GE7as | *g*aucacccuccuuaaauauuu | 2 | *c*gcumagumgggaggaaumumumaumaaa | 5 |
| GE1s/GE8as | *g*aucacccuccuuaaauauuu | 2 | *c*gmcmumagumgggaggaaumumumaumaaa | 6 |
| GE1s/GE9as | *g*aucacccuccuuaaauauuu | 2 | *c*<u>gmcm</u>umagumgggaggaaumumumaumaaa | 7 |
| GE1s/GE10as | *g*aucacccuccuuaaauauuu | 2 | *c*gmcmumagugggaggaauuumaumaaa | 8 |
| GE1s/GE11as | *g*aucacccuccuuaaauauuu | 2 | *c*gmcmuagugggaggaaumuuaumaaa | 9 |
| GE7s/GE1as | *g*aumcacccumccumumaaaumaumumum | 4 | *u*ucuagugggaggaauuuauaaa | 3 |
| LC1s/LC1as | *c*uuacgcugaguacuucgaTT | 10 | *u*cgaaguacucagcguaagTT | 11 |
| LC2s/LC2as | *g*cggaucaaaccucaccaaTT | 12 | *u*cgaaguacucagcguaagTT | 13 |

TABLE 2-continued

Sequences of sense and antisense strands of a first group of double stranded RNAs tested for stability in human serum. All sequences are given 5' → 3'.

| Duplex Descriptor | Sense | SEQ ID NO: | Antisense | SEQ ID NO: |
|---|---|---|---|---|
| AL-DP-5097 | cuuuacaagccuugguucagu | 14 | acugaaccaaggcuuguaaagug | 15 |
| AL-DP-5398 | cumumumacmaagccumumggumucmagu | 16 | acumgaaccmaaggcuumgumaaagumg | 17 |
| AL-DP-5458 | cufufufacfaagccufufggufucfagu | 18 | acufgaaccfaaggcuufgufaaaagmumg | 19 |
| AL-DP-5542 | cumumumacmaagccumumggumucmagu-Chol | 20 | cumgaaccmaaggcuumgumaaagmumg | 21 |
| AL-DP-5543 | cuuuacaagccuugguucagu-Chol | 22 | acugaaccaaggcuuguaaagmumg | 23 |
| AL-DP-5098 | ggaaucuuauauuugauccaa | 24 | uuggaucaaauauaagauucccu | 25 |
| AL-DP-5399 | ggaaucumumaumaumumumgauccmaa | 26 | umumggaucmaaaumaumaagaumuccmcmu | 27 |
| AL-DP-5459 | ggaaucufufaufaufufufgauccfaa | 28 | ufufggaucfaaaufaufaagaufuccmcmu | 29 |
| AL-DP-5544 | ggaaucumumaumaumumumgauccmaa-Chol | 30 | umumggaucmaaaumaumaagaumuccmcmu | 31 |
| AL-DP-5545 | ggaaucuuauauuugauccaa-Chol | 32 | uuggaucaaauauaagauuccmcmu | 33 |
| AL-DP-5024 | agguguauggcuucaacccug | 34 | cagggcuugaagccauacaccucu | 35 |
| AL-DP-5388 | aggumgumaumggcumucmaacccug | 36 | cmagggumumgaagccmaumacmaccumcmu | 37 |
| AL-DP-5448 | aggufgufaufggcufucfaacccug | 38 | cfagggufufgaagccfaufacfaccumcmu | 39 |
| AL-DP-5013 | gguguauggcuucaacccuga | 40 | ucagggcuugaagccauacaccuc | 41 |
| AL-DP-5387 | ggumgumaumggcumucmaacccumga | 42 | ucmagggumumgaagccmaumacmaccmumc | 43 |
| AL-DP-5447 | ggufgufaufggcufucfaacccufga | 44 | ucfagggufufgaagccfaufacfaccmumc | 45 |
| AL-DP-5084 | cugaacaucaagaggggcauc | 46 | gaugcccucuugauguucagga | 47 |
| AL-DP-5394 | cumgaacmaucaagaggggcmauc | 48 | gaumgcccucumumgaumgumucmagga | 49 |
| AL-DP-5454 | cufgaacfaucaagaggggcfauc | 50 | gaufgcccucufufgaufgufucfagmgma | 51 |
| AL-DP-5094 | gccccaucacuuuacaagccu | 52 | aggcuuguaaagugauggggcug | 53 |
| AL-DP-5397 | gccccmaucmacumumumacmaagccu | 54 | aggcumumgumaaagumgaumggggcmumg | 55 |
| AL-DP-5457 | gccccfaucfacufufufacfaagccu | 56 | aggcufufgufaaagufgaufggggcmumg | 57 |
| AL-DP-5093 | ucacauccuccaguggcugaa | 58 | uucagccacuggaggaugugagu | 59 |
| AL-DP-5396 | ucmacmauccuccmagumggcumgaa | 60 | umucmagccmacumggaggaumgumgagu | 61 |
| AL-DP-5456 | ucfacfauccuccfagufggcufgaa | 62 | ufucfagccfacufggaggaufgufgamgmu | 63 |
| AL-DP-5089 | gaguuugugacaaauauggggc | 64 | gcccauauuugucacaaacucca | 65 |
| AL-DP-5395 | gagumumumgumgacmaaaumaumgggc | 66 | gcccaumaumumumgucmacmaaacucmcma | 67 |
| AL-DP-5455 | gagufufufgufgacfaaaufaufgggc | 68 | gcccaufaufufufgucfacfaaacucmcma | 69 |
| AL-DP-5030 | gaacaccaacuucuuccacga | 70 | ucguggaagaaguuggugucau | 71 |
| AL-DP-5389 | gaacmaccmaacumucumuccmacga | 72 | ucgumggaagaagumumggumgumucmau | 73 |
| AL-DP-5449 | gaacfaccfaacufucufuccfacga | 74 | ucgufggaagaagufufggufgufucmamu | 75 |
| AL-DP-5035 | caccaacuucuuccacgaguc | 76 | gacucguggaagaaguugguguu | 77 |
| AL-DP-5390 | cmaccmaacumucumuccmacgaguc | 78 | gacucgumggaagaagumumggumgumu | 79 |
| AL-DP-5450 | cfaccfaacufucufuccfacgaguc | 80 | gacucgufggaagaagufufggumgmumu | 81 |
| AL-DP-5046 | aucaagugucaucacacugaa | 82 | uucaguguaugacacuugauuu | 83 |

TABLE 2-continued

Sequences of sense and antisense strands of a first group of double stranded RNAs tested for stability in human serum. All sequences are given 5' → 3'.

| Duplex Descriptor | Sense | SEQ ID NO: | Antisense | SEQ ID NO: |
|---|---|---|---|---|
| AL-DP-5391 | ªucmaagumgucmaucmacmacumgaa | 84 | umucmagumgumgaumgacmacumumgau mumu | 85 |
| AL-DP-5451 | ªucfaagufgucfaucfacfacufgaa | 86 | ufucfagufgufgaufgacfacufufgaum umu | 87 |
| AL-DP-5048 | ᵍucaucacacugaauaccaau | 88 | ªuugguauucagugugaugacac | 89 |
| AL-DP-5392 | ᵍucmaucmacmacumgaaumaccmaau | 90 | aumumggumaumucmagumgumgaumgac mac | 91 |
| AL-DP-5452 | ᵍucfaucfacfacufgaaufaccfaau | 92 | aufufggufaufucfagufgufgaufgacm amc | 93 |
| AL-DP-5002 | ᵍauugauugaccuguccauuc | 94 | ᵍaauggacaggucaaucaaucuu | 95 |
| AL-DP-5386 | ᵍaumumgaumumgaccumguccmaumuc | 96 | gaaumggacmaggucmaaucmaaucmumu | 97 |
| AL-DP-5446 | ᵍaufufgaufufgaccufguccfaumuc | 98 | gaaufggacfaggucfaaucfaaucmumu | 99 |
| AL-DP-5049 | ᶜuguccauucaaaacuaccac | 100 | ᵍugguaguuuugaauggacaggu | 101 |
| AL-DP-5393 | ᶜumguccmaumucmaaaacumaccmac | 102 | gumggumagumumumumgaaumggacmag gu | 103 |
| AL-DP-5453 | ᶜufguccfaufucfaaaacufaccfac | 104 | pgufggufagufufufufgaaufggacfagm gmu | 105 |
| AL-DP-5437 | ᵍucaucacacugaauaccaau | 106 | ªuugguauucagugugaugacac | 107 |
| AL-DP-5392 | ᵍucmaucmacmacumgaaumaccmaau | 108 | paumumggumaumucmagumgumgaumga cmac | 109 |
| AL-DP-HCV | ªcggcuagcugugaaaggucc | 110 | ᵍgaccuuucacagcuagccguga | 111 |

The sense strands GE1s and GE7s were annealed respectively with the anti sense strands GE1as, GE8as, GE9as, GE10as, GE11as; sense strand LC1s was annealed with anti-sense strand LC1as. The resulting double strand RNA duplexes are referred to herein as [sense strand]/[anti sense strand], e.g. GE1s/GE1as is used to denominate the duplex formed by annealing of GE1s with GE1as.

The nucleotides at positions 1-21, counting 5, to 3', of the anti sense strands GE1as, GE7as, GB8as, GE9as, GE10as, and GE11as are complementary to position 1488-1508 of the sequence available under GenBank accession number X75932. The nucleotides at positions 1-19 of the anti sense strand LC1as are complementary to positions 434-452 of the sequence available under GenBank accession number U47298.

AL-DP-5097, AL-DP-5398, AL-DP-5458, AL-DP-5542, and AL-DP-5543 are identical in sequence except for 2'-modifications, phosphorothioate linkages, and 3'-teminal cholesteryl ligands. The anti sense strands are complementary to positions 1259-1281 of the human ApoB gene (GenBank accession no. NM_000384).

AL-DP-5098, AL-DP-5399, AL-DP-5459, AL-DP-5544, and AL-DP-5545 are identical in sequence except for 2'-modifications, phosphorothioate linkages, and 3'-teminal cholesteryl ligands. The antisense strands are complementary to positions 2096-2118 of the human ApoB gene.

AL-DP-5024, AL-DP-5388, and AL-DP-5448 are identical in sequence except for 2'-modifications, phosphorothioate linkages, and 3'-teminal cholesteryl ligands. The antisense strands are complementary to positions 428-450 of the human ApoB gene.

AL-DP-5013, AL-DP-5387, and AL-DP-5447 are identical in sequence except for 2'-modifications, phosphorothioate linkages, and 3'-teminal cholesteryl ligands. The antisense strands are complementary to positions 429-451 of the human ApoB gene.

AL-DP-5084, AL-DP-5394, and AL-DP-5454 are identical in sequence except for 2'-modifications, phosphorothioate linkages, and 3'-teminal cholesteryl ligands. The antisense strands are complementary to positions 586-608 of the human ApoB gene.

AL-DP-5094, AL-DP-5397, and AL-DP-5457 are identical in sequence except for 2'-modifications, phosphorothioate linkages, and 3'-teminal cholesteryl ligands. The antisense strands are complementary to positions 1250-1272 of the human ApoB gene.

AL-DP-5093, AL-DP-5396, and AL-DP-5456 are identical in sequence except for 2'-modifications, phosphorothioate linkages, and 3'-teminal cholesteryl ligands. The antisense strands are complementary to positions 1302-1324 of the human ApoB gene.

AL-DP-5089, AL-DP-5395, and AL-DP-5455 are identical in sequence except for 2'-modifications, phosphorothioate linkages, and 3'-teminal cholesteryl ligands. The antisense strands are complementary to positions 2770-2792 of the human ApoB gene.

AL-DP-5030, AL-DP-5389, and AL-DP-5449 are identical in sequence except for 2'-modifications, phosphorothioate linkages, and 3'-teminal cholesteryl ligands. The antisense strands are complementary to positions 2829-2851 of the human ApoB gene.

AL-DP-5035, AL-DP-5390, and AL-DP-5450 are identical in sequence except for 2'-modifications, phosphorothioate linkages, and 3'-teminal cholesteryl ligands. The antisense strands are complementary to positions 2832-2854 of the human ApoB gene.

AL-DP-5046, AL-DP-5391, and AL-DP-5451 are identical in sequence except for 2'-modifications, phosphorothioate linkages, and 3'-teminal cholesteryl ligands. The antisense strands are complementary to positions 10158-10180 of the human ApoB gene.

AL-DP-5048, AL-DP-5392, and AL-DP-5452 are identical in sequence except for 2'-modifications, phosphorothioate linkages, and 3'-teminal cholesteryl ligands. The antisense strands are complementary to positions 10165-10187 of the human ApoB gene.

AL-DP-5002, AL-DP-5386, and AL-DP-5446 are identical in sequence except for 2'-modifications, phosphorothioate linkages, and 3'-teminal cholesteryl ligands. The antisense strands are complementary to positions 13682-13704 of the human ApoB gene.

AL-DP-5049, AL-DP-5393, and AL-DP-5453 are identical in sequence except for 2'-modifications, phosphorothioate linkages, and 3'-teminal cholesteryl ligands. The antisense strands are complementary to positions 13693-13715 of the human ApoB gene.

The sense strand of AL-DP-HCV corresponds to positions 9475-9495 of the 3'-untranslated region of hepatitis C virus (GenBank accession number: D89815).

3. Serum Incubation Assay

Blood of 8 human volunteers (270 mL) was collected and kept at room temperature for 3 hours. The blood pool was then centrifuged at 20° C. and 3000 rcf using Megafuge 1.0 (Heraeus Instruments, Kendro Laboratory Products GmbH, Langenselbold) to separate the serum from the cellular fraction. The supernatant was stored in aliquots at −20° C. and used as needed. Alternatively, human serum or mouse serum obtained from Sigma (Sigma-Aldrich Chemie GmbH, Taufkirchen, Germany, cat. No. human serum H1513, mouse serum M5905) was employed. Assay results reported herein were consistent among the different human serum sources. Mouse serum showed somewhat higher exonucleolytic activity than human serum.

Double stranded RNAs (300 pmol, ca. 4.2 µg) dissolved in 6 µl phosphate buffered saline (PBS) were added to 60 µl human serum in a 1.5 ml Eppendorf tube, and the mixture was incubated for varying extents of time, e.g. 0, 15, or 30 minutes, or 1, 2, 4, 8, 16, or 24 hours in a thermomixer (Eppendorf thermomixer comfort; Eppendorf, Hamburg, Germany) at 37° C. and 1050 rpm. Subsequently, the whole tube containing the RNA/serum solution was immediately processed further or frozen in liquid nitrogen and stored at −80° C. until analysis. As a control, the same amount of double stranded RNA was added to 60 µl annealing buffer, incubated a 37° C. for 0, 24 or 48 hours, and immediately further processed or frozen in liquid nitrogen and stored at −80° C. until analysis.

4. Analysis by Electrophoresis and "Stains All" Detection

For analysis, frozen serum incubation samples from store were thawed, their constituents were isolated by phenol-extraction and ethanol-precipitation, separated on denaturing 14% polyacrylamide gels (6M Urea, 20% formamide, Carl Roth GmbH & Co KG Karlsruhe, Germany) and detected by staining with the "stains-all" reagent (Sigma-Aldrich Chemie GmbH, Steinheim, Germany). Reaction mixtures from incubation of selected dsRNAs were further analysed covering the time points 8 hours, 16 hours and 24 hours.

4.1 Isolation of siRNA

For analysis, the frozen samples were placed on ice and 450 µl of 0.5 M NaCl was added, followed by brief vortexing. After complete thawing, the resulting solution was transferred to Phase-Lock Gel tubes (Eppendorf, Hamburg, Germany; cat. No. 0032 005.152), fixed with 500 µl 50% phenol, 48% chloroform, 2% isoamylacohol (Carl Roth GmbH & Co KG, Karlsruhe, Germany, cat. No. A156.2), and an additional 300 µl chloroform were added. The tubes were vortexed vigorously for 30 seconds and subsequently centrifuged for 15 min at 16.200 rcf and 4° C. The aqueous supernatant was transferred to a fresh tube, mixed with 40 µl 3M Na-acetate pH 5.2, 1 µl GlycoBlue (Ambion, Tex., USA; cat. No. 9515) and 1 ml Ethanol 95%, and vortexed vigorously for ca. 20 s. Precipitation of RNA was brought to completion over night at −20° C.

4.2 Denaturing Gel Electrophoresis and RNA Staining

The following day, tubes were centrifuged for 30 min at 16.200 rcf and 4° C. The supernatant was removed and discarded. The RNA pellet was washed with 500 µl ice-cold Ethanol 70%, and re-pelleted by centrifugation for 10 min at 16.200 rcf and 4° C. All liquid was removed, the pellet was air-dried for 1 min and dissolved in 12 µl gel loading buffer (95% formamide, 5% EDTA 1M, 0.02% xylene cyanol, 0,02% bromophenol blue). The gel was pre-run for 1 h at 100 W. The samples were boiled for 10 min at 95° C. and chilled quickly on ice. 4 µl were loaded on a denaturing 14% polyacrylamide gel (8M Urea, 20% formamide, 19:1 acrylamide: N,N-Methylenebisacrylamide). The RNA was separated for about 40 min at 100 W (Sequi-Gen GT gel system, 38×30 cm, Bio-Rad Laboratories, Hercules, Calif., USA, cat. no. 165-3862). RNA bands were visualized by staining with the "stains-all" reagent (Sigma-Aldrich Chemie GmbH, Steinheim, Germany, cat. no. E9379) according to manufacturer's instructions.

5. Analysis by LC/MS

Frozen serum incubation samples from store were thawed, their constituents were isolated by phenol-extraction and ethanol-precipitation, the resulting pellet was dissolved in 50 µl of water and 42 µl of this solution was injected into the HPLC-system (Amersham Biosciences Ettan mLC-System equipped with UV-detection system and Jetstream column heater coupled to Thermo Finnigan LCQ DecaXp mass spectrometer; HPLC column: Waters Xterra C8-MS; 2.1×50 mm; particle size 2.5 µm; 60° C.; Flow 200 µl/min; UV-Detection at 254 nm; ESI source and IonTrap-detector, total ion current detection for MS-detection). The MS-instrument was started with a 3 min time delay after the injection to protect the mass spectrometer from salt and other unbound sample impurities. An eluent gradient was employed as follows:

Eluents:
A: 400 mM Hexafluoroisopropanol/16.3 mM Triethylamine in deionized water; pH=7.9
B: Methanol (LC-MS grade)

| Gradient table: | 0->3 min: | 1% B; |
|---|---|---|
| | 3->33 min: | 1%->24% B linear; |
| | 33.1 min: | 100% B; |
| | 33.1->35 min: | 100% B |
| | 35.1 min: | 1% B |
| | 35.1->38 min: | 1% B |

Due to the denaturing conditions on the column (60° C.), all sample fragments elute as single strands. Every fragment is detected as one peak in the UV- and the TIC-chromatogram. A raw mass spectrum of every peak is extracted from the TIC-chromatogram and deconvoluted using the software "Bioworks", Version 3.1 (Thermo Electron GmbH, Dreieich, Germany). At the end of each run, the column is washed and re-equilibrated.

Comparison between the experimentally detected and the calculated masses of all possible fragments of both duplex strands leads to the identification of the cleavage fragments generated during serum incubation. The LC-MS method is insensitive to phosphate-induced shifts as are the gel assays and allows an exact mapping of all cleavage sites.

Data evaluation steps:

1.) Average isotopic masses are calculated for all hypothetical fragments of both the sense and the antisense strand.

2.) 62.0 Da are added to the hypothetical fragment masses to account for a cyclic diester phosphate terminus at the cleavage site; for a cyclic diester phosphorothioate at the cleavage position, +78,06 Da are added; 80,0 Da are added for a 2'- or 3'-monoester phosphate group, and +96.06 Da are added for a phosphorothioate monoester.

3.) All experimental masses are compared to these predicted masses; a fragment is identified if its experimentally determined mass falls to within ±1 Da of the predicted mass.

4.) Fragments unequivocally assignable allow the identification of cleavage positions.

5.) The increase or decrease of a peak at different time points allow conclusions on whether the cleavage is a primary or secondary event.

2'-3'-cyclic phosphates and the resulting hydrolyzed 2'- or 3'-phosphates as possible termini after the cleavage event were included into the mass calculation of the fragments. This end group analysis provided an insight to the cleavage mechanism. If a cyclic phosphate was detected at the 3'-end of a fragment resulting from cleavage, a nucleophilic attack of the 2'-OH on the 3'-O—P phosphorus of the internal base must have been involved in the cleavage mechanism. For stabilization against degradation following this mechanism, a 2'-modification, e.g. a 2'-O-Methyl substitution on the respective nucleotide, may be employed.

6. Determination of siRNA Degradation Time Course by HPLC Following Proteinase K Treatment of Serum Samples In order to get a more quantitative means of determining siRNA strand degradation, a method comprising Proteinase K treatment of serum samples followed by the separation of serum sample constituents on an HPLC was developed. By comparison of different modified and unmodified siRNAs, this method can be used to identify sites and sequence motifs in siRNA strands that are particularly vulnerable to nucleolytic degradation.

The example below shows the analyses of serum samples which were contacted with siRNAs in vitro. However, this method can equally be applied to biological samples ex vivo, i.e. obtained from a subject which was contacted with an siRNA in vivo.

Proteinase K (20 mg/ml) was obtained from peQLab (Erlangen, Germany; Cat.-No. 04-1075) and diluted 1:1 with deionized water (18.2 mΩ) to a final concentration of 10 mg/ml Proteinase K. Proteinase K Buffer (4.0 ml TRIS-HCl 1M pH 7.5, 1.0 ml EDTA 0.5M, 1.2 ml NaCl 5M, 4.0 ml SDS 10%) was prepared fresh and kept at 50° C. until use to avoid precipitation.

A 40 mer of poly(L-dT), $(L-dT)_{40}$ was obtained from Noxxon Pharma AG (Berlin, Germany) and used as an internal standard. Polymers of the L-enantiomers of nucleic acids show an extraordinary stability towards nucleolytic degradation (Klussman S, et al., Nature Biotechn. 1996, 14:1112) but otherwise very similar properties when compared to naturally occuring nucleic acids consisting of R-enantiomers.

6.1 Proteinase K Treatment of Serum Incubation Samples

To terminate the siRNA-degradation, 25 µl of Proteinase K buffer were added to serum incubation samples immediately after expiry of the respective incubation period, the mixture vortexed at highest speed for 5 s (Vortex Genie 2, Scientific Industries, Inc., Bohemia, N.Y., USA, cat. no. SI 0256), 8 µl Proteinase K (10 mg/ml) were added followed by vortexing for 5 s, and finally the mixture was incubated for 20 min in a thermomixer at 42° C. and 1050 rpm.

6 µl of a 50 µM solution (300 pmole) of $(L-dT)_{40}$ were added as an internal standard, the solution was vortexed for 5 s, and the tube centrifuged for 1 min in a tabletop centrifuge to collect all droplets clinging to the inner surfaces of the tube at the bottom. The solution was transferred to a Microcon Centrifugal Filter Unit YM-100 (Millipore GmbH, Eschborn, Germany, Cat. No. 42413) and filtered by centrifugation at 21900 rcf for 45 min.

The incubation tube was washed with 47.5 µl deionized water (18.2 mΩ), the wash filtered through the Microcon Centrifugal Filter Unit at 21900 rcf for 15 min, and the wash step repeated. Approximately 180 µl of the theoretical total volume of 200 µl are on average recovered after the second washing step.

6.2 Ion Exchange Chromatographic Separation of siRNA Single Strands from Each Other and from Degradation Products:

A Dionex BioLC HPLC-system equipped with inline-degasser, autosampler, column oven and fixed wavelength UV-detector (Dionex GmbH, Idstein, Germany) was used under denaturing conditions. Standard run parameters were:

Column: Dionex DNA-Pac100; 4×250 mm
Temperature: 75° C.
Eluent A: 10 mM $NaClO_4$, 20 mM TRIS-HCl, 1 mM EDTA; 10% acetonitrile, pH=8.0
Eluent B: 800 mM $NaClO_4$, 20 mM TRIS-HCl, 1 mM EDTA; 10% acetonitrile, pH=8.0
Detection: @ 260 nm

| Gradient: | 0-1 min: | 10% B |
|---|---|---|
| | 1-11 min: | 10%->35% B |
| | 11-12 min: | 35% B->100% B |
| | 12-14 min: | 100% B->10% B |
| | 14-16 min: | 10% B for column reequilibration |

Injection volume: 20 µl

Where separation between the two strands of an siRNA was not satisfactory or a degradation fragment co-eluted with one strand, the chromatographic parameters were adjusted by changing temperature, pH, and/or the concentration of acetonitrile, until separation was achieved which allowed separate quantitation of the peaks from sense and antisense strand.

Peak areas for full length strands were obtained by integration of the UV detector signal using software supplied by the manufacturer of the instrument (Chromeleon 6.5; Dionex GmbH, Idstein, Germany).

6.3 Data Analysis:

Integrated sense strand, antisense strand, and internal standard peak areas were obtained for all samples and the normalization control.

A correction factor CF, accounting for liquid losses in the filtration and washing steps, was determined for every sample by calculating the ratio of experimental to theoretical internal standard peak area. The theoretical internal standard peak area is obtained, e.g. from a calibration curve of the internal standard obtained by injecting 20 µl each of a serial dilution of the 50 µM solution of (L-dT)$_{40}$ onto the HPLC column, and calculation of the theoretical peak area corresponding to 30 pmole (L-dT)$_{40}$ with the equation obtained by linear least square fit to the peak areas from the dilution series. The correction factor CF to be applied to the peak areas of the sense and antisense strand is obtained as:

CF=PeakArea$_{intstd}$ (theoretical)/PeakArea$_{intstd}$ (Sample)

This treatment assumes that, by virtue of washing the filter twice, virtually complete recovery is achieved in the combined filtrates, and corrects for the variable volume of wash water retained in the filter, such that peak areas from different samples can be compared.

The peak areas obtained for the sense and antisense strand peaks for each time point are then multiplied with the correction factor CF to obtain Normalized Peak Areas (NPA$_{sense,t}$, NPA$_{antisense,t}$):

NPA$_{sense\ or\ antisense,t}$=(Peak Area$_{sense\ or\ antisense,t}$)×CF

To obtain the relative amount of remaining Full Length Product (%FLP) for the sense and antisense strands at time t, the Normalized Peak Area for each strand at time t=0 min (NPA$_{sense,t=0}$, NPA$_{antisense,t=0}$) is set as 100%, and the NPAs from other time points are divided by these values.

% FLP$_{t=1, 2, 3 \ldots n}$=(NPA$_{t=1, 2, 3 \ldots n}$/NPA$_{t=0}$)*100

The value obtained from the control sample, where the siRNA was incubated with annealing buffer only, may serve as a control of the accuracy of the method. The %FLP for both strands should lie near 100%, within error margins, regardless of time of incubation.

The degradation half life $t_{1/2}$ may then be calculated for each strand, assuming first order kinetics, from the slope of a linear least square fit to a plot of 1 n(% FLP) versus time as:

$t_{1/2}$=1 n(0,5)/slope

7. Analysis of the Ability of Unmodified and Modified siRNAs to Inhibit the Expression of a Target Gene
7.1 Incubation of Cultured HepG2 Cells with siRNAs Specific for Human ApoB The ability of siRNAs bearing no modifications or various combinations of 2'-O-methyl, 2'-deoxy-2'-fluoro, and phosphorothioate linkages to inhibit the expression of human ApoB was tested. HepG2 cells in culture were used for quantitation of ApoB mRNA in total mRNA isolated from cells incubated with ApoB-specific siRNAs by branched DNA assay. HepG2 cells were obtained from American Type Culture Collection (Rockville, Md., cat. No. HB-8065) and cultured in MEM (Gibco Invitrogen, Invitrogen GmbH, Karlsruhe, Germany, cat. No. 21090-022) supplemented to contain 10% fetal calf serum (FCS) (Biochrom AQ Berlin, Germany, cat. No. S0115), 2 mM L-Glutamin (Biochrom AC; Berlin, Germany, cat. No. K0238), Penicillin 100 U/ml, Streptomycin 100 µg/ml (Biochrom AG, Berlin, Germany, cat. No. A2213), 1× non-essential amino acids (NEA) (Biochrom AG, Berlin, Germany, cat. No. K0293) and 1 mM sodium pyruvate (Biochrom AG, Berlin, Germany, cat. No. L0473) at 37° C. in an atmosphere with 5% $CO_2$ in a humidified incubator (Heraeus HERAcell, Kendro Laboratory Products, Langenselbold, Germany).

For transfection with siRNA, HepG2 cells were seeded at a density of 1.5×10$^4$ cells/well in 96-well plates and cultured for 24 hours. Transfection of siRNA was carried out with oligofectamine (Invitrogen GmbH, Karlsruhe, Germany, cat. No. 12252-011) as described by the manufacturer. SiRNAs were transfected at a concentration of 30 nM for the screening of siRNA duplexes. 24 hours after transfection, the medium was changed and cells were incubated for an additional 24 hours. For measurement of ApoB mRNA by branched DNA assay, as described below, cells were harvested and lysed following procedures recommended by the manufacturer of the Quantigene Explore Kit (Genospectra, Fremont, Calif., USA, cat. No. QG-000-02) for bDNA quantitation of mRNA, except that 2 µl of a 50 µg/µl stock solution of Proteinase K (Epicentre, Madison, Wis., USA, Cat. No. MPRK092) was added to 600 µl of Tissue and Cell Lysis Solution (Epicentre, Madison, Wis., USA, cat. No. MTC096H). Lysates were stored at −80° C. until analysis by branched DNA assay.

AL-DP-HCV (see Table 2, SEQ ID NO. 10 and SEQ ID NO. 111) was used as negative control.
7.2 Branched DNA Assay for the Quantitation of ApoB mRNA in Cultured HepG2 Cells ApoB100 mRNA levels were measured by branched-DNA (bDNA) assay. The assay was performed using the Quantigene Explore Kit (Genospectra, Fremont, Calif., USA, cat. No. QG-000-02). Frozen lysates were thawed at room temperature, and ApoB and GAPDH mRNA quantified using the Quantigene Explore Kit according to manufacturer's instructions. Nucleic acid sequences for Capture Extender (CE), Label Extender (LE) and blocking (BL) probes were selected from the nucleic acid sequences of ApoB and GAPDH with the help of the QuantiGene ProbeDesigner Software 2.0 (Genospectra, Fremont, Calif., USA, cat. No. QG-002-02). Probe nucleotide sequences used in quantization of human ApoB are shown in Table 3. Probe nucleotide sequences used in quantization of human GAPDH are shown in Table 4.

The ApoB mRNA levels were normalized across different samples by comparing the ratio of ApoB mRNA to GAPDH mRNA present in the samples. The activity of a given ApoB specific siRNA duplex was expressed as a percentage of ApoB mRNA (ApoB mRNA/GAPDH mRNA) in treated cells relative to cells treated with the control siRNA.

TABLE 3

DNA probes for human ApoB used in branched-DNA assays

| Probe type[a] | Nucleotide sequence | SEQ. ID. No. |
|---|---|---|
| CE | GATTGGATTTTCAGAATACTGTATAGCTTTTTTCTCTTGGAAAGAAAGT | 156 |
| CE | CCTGCTTCGTTTGCTGAGGTTTTTTCTCTTGGAAAGAAAGT | 157 |
| CE | GCAGTGATGGAAGCTGCGATATTTTTCTCTTGGAAAGAAAGT | 158 |

TABLE 3-continued

DNA probes for human ApoB used in branched-DNA assays

| Probe type[a] | Nucleotide sequence | SEQ. ID. No. |
|---|---|---|
| CE | GAACTTCTAATTTGGACTCTCCTTTGTTTTTCTCTTGGAAAGAAAGT | 159 |
| CE | ACTCCTTCAGAGCCAGCGGTTTTTCTCTTGGAAAGAAAGT | 160 |
| CE | ACTCCCATGCTCCGTTCTCATTTTTCTCTTGGAAAGAAAGT | 161 |
| CE | AGGGTAAGCTGATTGTTTATCTTGATTTTTCTCTTGGAAAGAAAGT | 162 |
| LE | GGTTCCATTCCCTATGTCAGCATTTTTAGGCATAGGACCCGTGTCT | 163 |
| LE | ATTAATCTTAGGGTTTGAGAGTTGTGTTTTTAGGCATAGGACCCGTGTCT | 164 |
| LE | CACTGTGTTTGATTTTCCCTCAATATTTTTAGGCATAGGACCCGTGTCT | 165 |
| LE | TGTATTTTTTCTGTGTGTAAACTTGCTTTTTAGGCATAGGACCCGTGTCT | 166 |
| LE | CAATCACTCCATTACTAAGCTCCAGTTTTTAGGCATAGGACCCGTGTCT | 167 |
| BL | TGCCAAAAGTAGGTACTTCAATTG | 168 |
| BL | TTTGCATCTAATGTGAAAAGAGGA | 169 |
| BL | CATTTGCTTGAAAATCAAAATTGA | 170 |
| BL | GGTACTTGCTGGAGAACTTCACTG | 171 |
| BL | GCATTTCCAAAAAACAGCATTTC | 172 |

[a] CE = Capture Extender probe;
LE = Label Extender probe;
BL = blocking probe

TABLE 4

DNA probes for human GAPDH used in branched-DNA assays

| Probe type[a] | Nucleotide sequence | SEQ. ID. No. |
|---|---|---|
| CE | GAATTTGCCATGGGTGGAATTTTTTCTCTTGGAAAGAAAGT | 173 |
| CE | GGAGGGATCTCGCTCCTGGATTTTTCTCTTGGAAAGAAAGT | 174 |
| CE | CCCCAGCCTTCTCCATGGTTTTTTCTCTTGGAAAGAAAGT | 175 |
| CE | GCTCCCCCCTGCAAATGAGTTTTTCTCTTGGAAAGAAAGT | 176 |
| LE | AGCCTTGACGGTGCCATGTTTTTAGGCATAGGACCCGTGTCT | 177 |
| LE | GATGACAAGCTTCCCGTTCTCTTTTTAGGCATAGGACCCGTGTCT | 178 |
| LE | AGATGGTGATGGGATTTCCATTTTTTAGGCATAGGACCCGTGTCT | 179 |
| LE | GCATCGCCCCACTTGATTTTTTTAGGCATAGGACCCGTGTCT | 180 |
| LE | CACGACGTACTCAGCGCCATTTTTAGGCATAGGACCCGTGTCT | 181 |
| LE | GGCAGAGATGATGACCCTTTTGTTTTTAGGCATAGGACCCGTGTCT | 182 |
| BL | GGTGAAGACGCCAGTGGACTC | 183 |

[a] CE = Capture Extender probe;
LE = Label Extender probe;
BL = blocking probe

8. Results
8.1 Results from Electrophoretic Separation of dsRNA Fragments Followed by Staining The stability of the partially modified dsRNA of Table 2 labelled GE1s/GE1as through GE7s/GE1as was assessed using the serum incubation assay using human serum followed by analysis of fragments using the "stains all" or LC/MS procedure. A number of sequence motifs were found to be particularly susceptible to cleavage by endonucleases present in mammalian serum. By incorporating 2'-O-methyl modified nucleotides at strategic sites within a dsRNA it was possible to significantly increase the stability and integrity of such molecules in biologic media such as serum.

Figure 5:
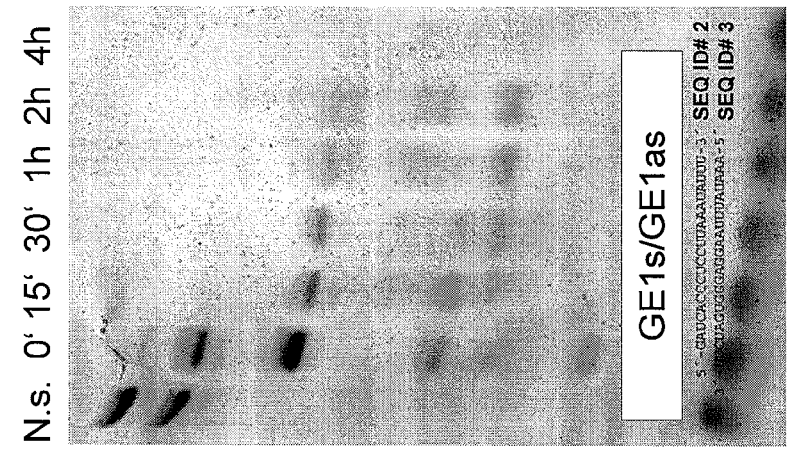
FIG. 5 shows a gel electrophoretic separation, stained using the "stains all" reagent, of an unmodified (control) dsRNA (referred to as "GE1s/GE1as") after 0, 15, 30, 60, 120 and 240 minutes of incubation in serum.
Figures 11, 12, 13:
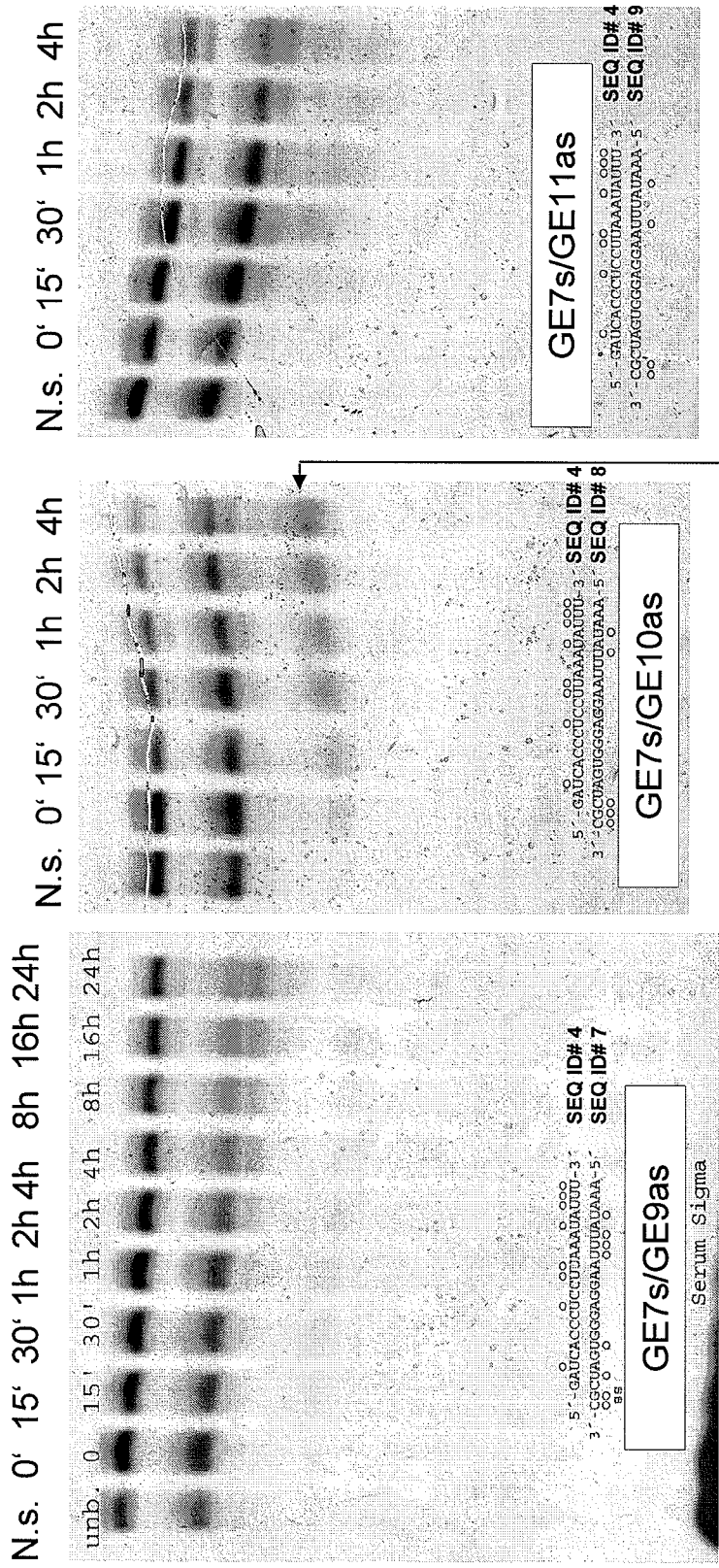
FIG. 11 shows a gel electrophoretic separation, stained using the "stains all" reagent, of a nuclease resistant dsRNA of the present invention (referred to as "GE7s/GE9as") after 0, 15, and 30 minutes, and 1, 2, 4, 8, 16 and 24 hours of incubation in serum.
FIG. 12 shows a gel electrophoretic separation, stained using the "stains all" reagent, of a nuclease resistant dsRNA of the present invention (referred to as "GE7s/GE10as") after 0, 15, 30, 60, 120 and 240 minutes of incubation in serum. The sequence of one major fragment derived from endonucleolytic attack on the antisense strand between positions 8 and 9 (5'-$U^8|A^9$-3'), as determined by mass spectrometry, is shown.
FIG. 13 shows a gel electrophoretic separation, stained using the "stains all" reagent, of a nuclease resistant dsRNA of the present invention (referred to as "GE7s/GE11as") after 0, 15, 30, 60, 120 and 240 minutes of incubation in serum.
Figures 14, 15, 16:
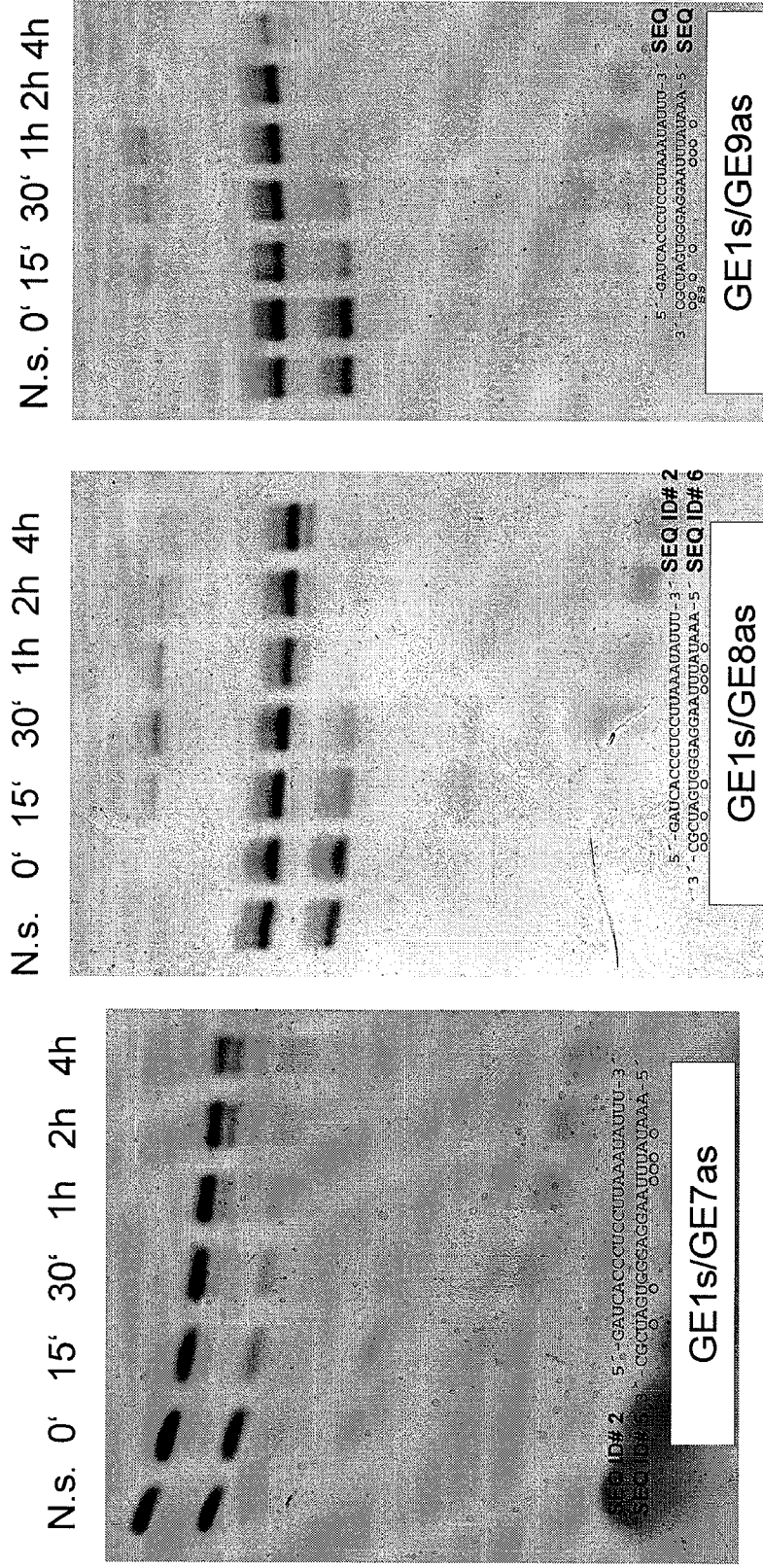
FIG. 14 shows a gel electrophoretic separation, stained using the "stains all" reagent, of the dsRNA referred to herein as "GE1s/GE7as" after 0, 15, 30, 60, 120 and 240 minutes of incubation in serum.
FIG. 15 shows a gel electrophoretic separation, stained using the "stains all" reagent, of the dsRNA referred to herein as "GE1s/GE8as" after 0, 15, 30, 60, 120 and 240 minutes of incubation in serum.
FIG. 16 shows a gel electrophoretic separation, stained using the "stains all" reagent, of the dsRNA referred to herein as "GE1s/GE9as" after 0, 15, 30, 60, 120 and 240 minutes of incubation in serum.
Figures 17, 18, 19:
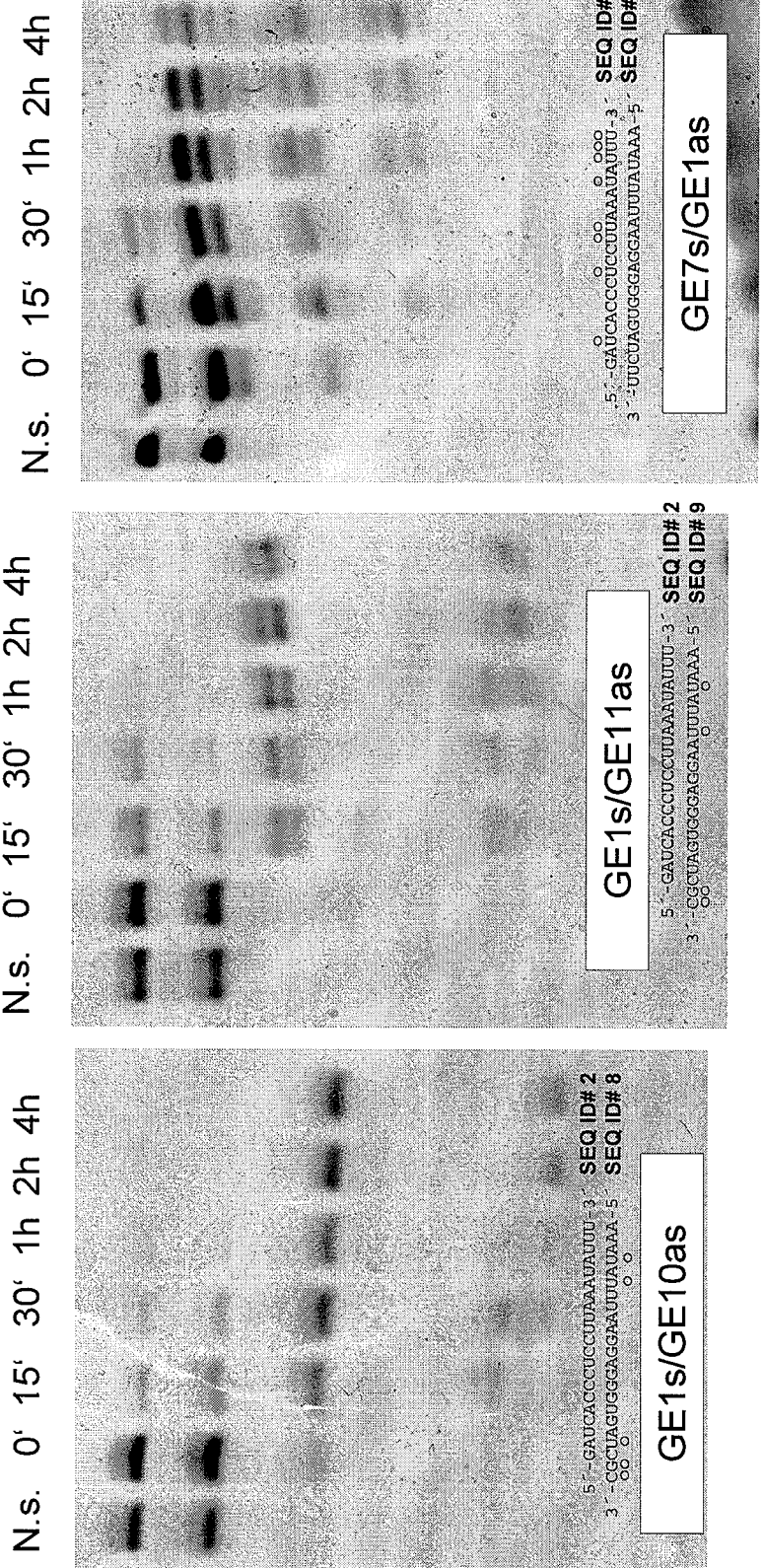
FIG. 17 shows a gel electrophoretic separation, stained using the "stains all" reagent, of the dsRNA referred to herein as "GE1s/GE10as" after 0, 15, 30, 60, 120 and 240 minutes of incubation in serum.
FIG. 18 shows a gel electrophoretic separation, stained using the "stains all" reagent, of the dsRNA referred to herein as "GE1s/GE11as" after 0, 15,30,60, 120 and 240 minutes of incubation in serum.
FIG. 19 shows a gel electrophoretic separation, stained using the "stains all" reagent, of the dsRNA referred to herein as "GE7s/GE1as" after 0, 15, 30, 60, 120 and 240 minutes of incubation in serum.
Figure 20:
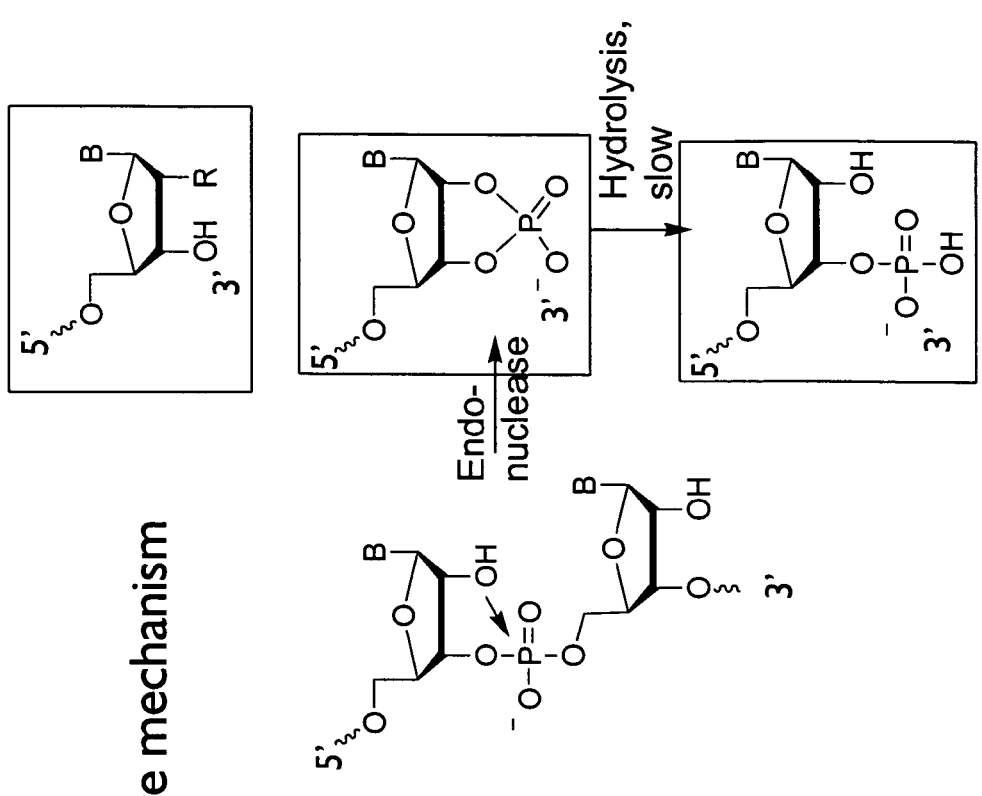
FIG. 20 shows schematically the difference between the products of exo- and endonucleolytic degradation of RNA. Exonucleolytic degradation requires a phosphodiester bond between the last and penultimate bases on the 3'-end of the RNA strand and may be hindered by substituting the phosphodiester group by a phosphorothioate. Endonucleolytic degradation proceeds via nucleophilic attack of a 2'-hydroxyl group on its 3'-phosphorous, and may be hindered by substituting the 2'-hydroxyl group by, e.g. a 2'-O-methyl group.
Figure 21:
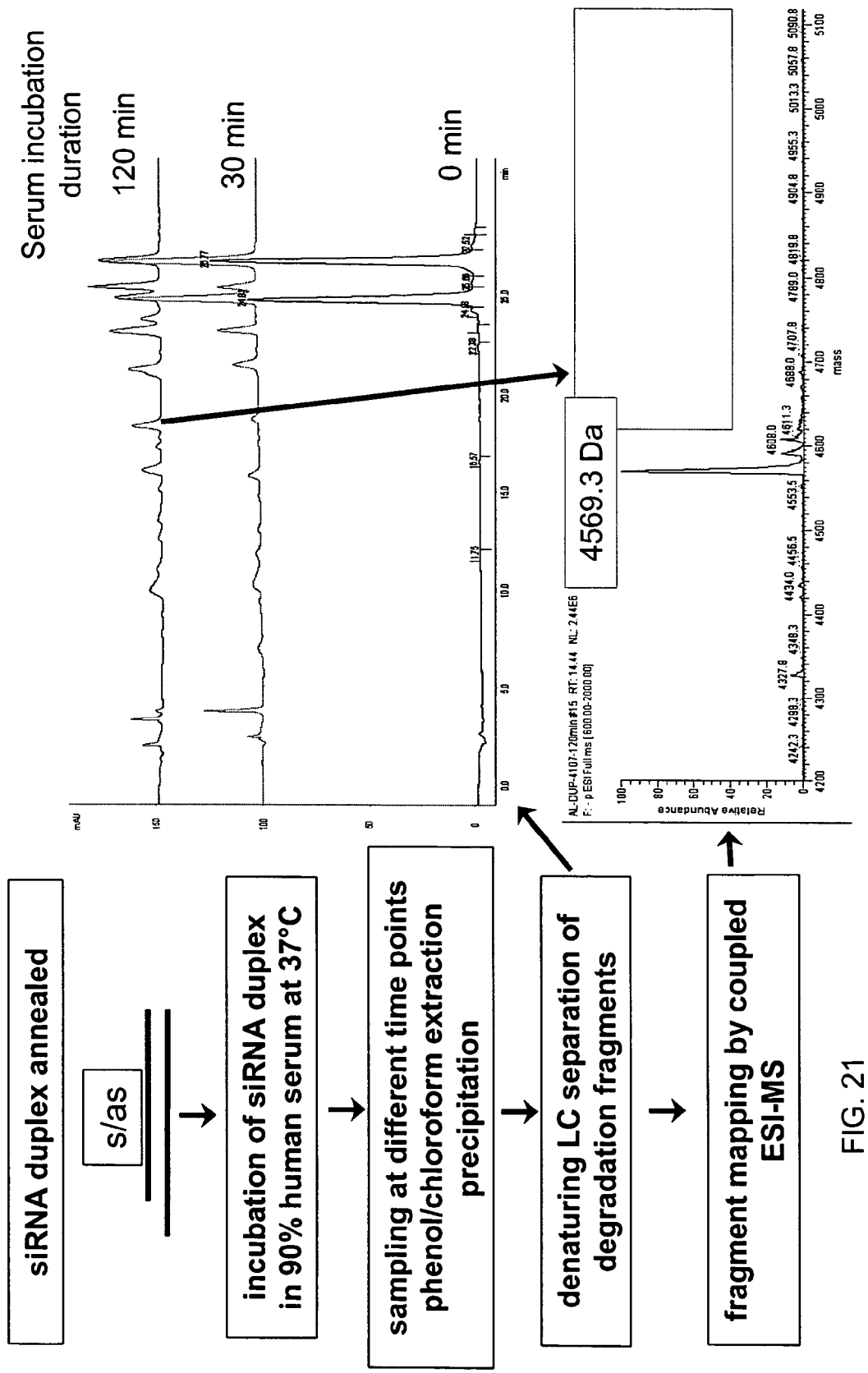
FIG. 21 shows schematically the process by which the products of nucleolytic degradation of dsRNA in serum were identified using liquid chromatography/mass spectrometry (LC/MS). DsRNA was incubated with mouse or human serum for various time spans, total RNA was isolated from the incubation mix and fragments separated on an LC under denaturing conditions. The LC output was fed into a mass spectrometer and the mass of ions appearing in mass spectrometric analysis was compared to the predicted masses of all possible fragments for a given dsRNA.
Figure 22:
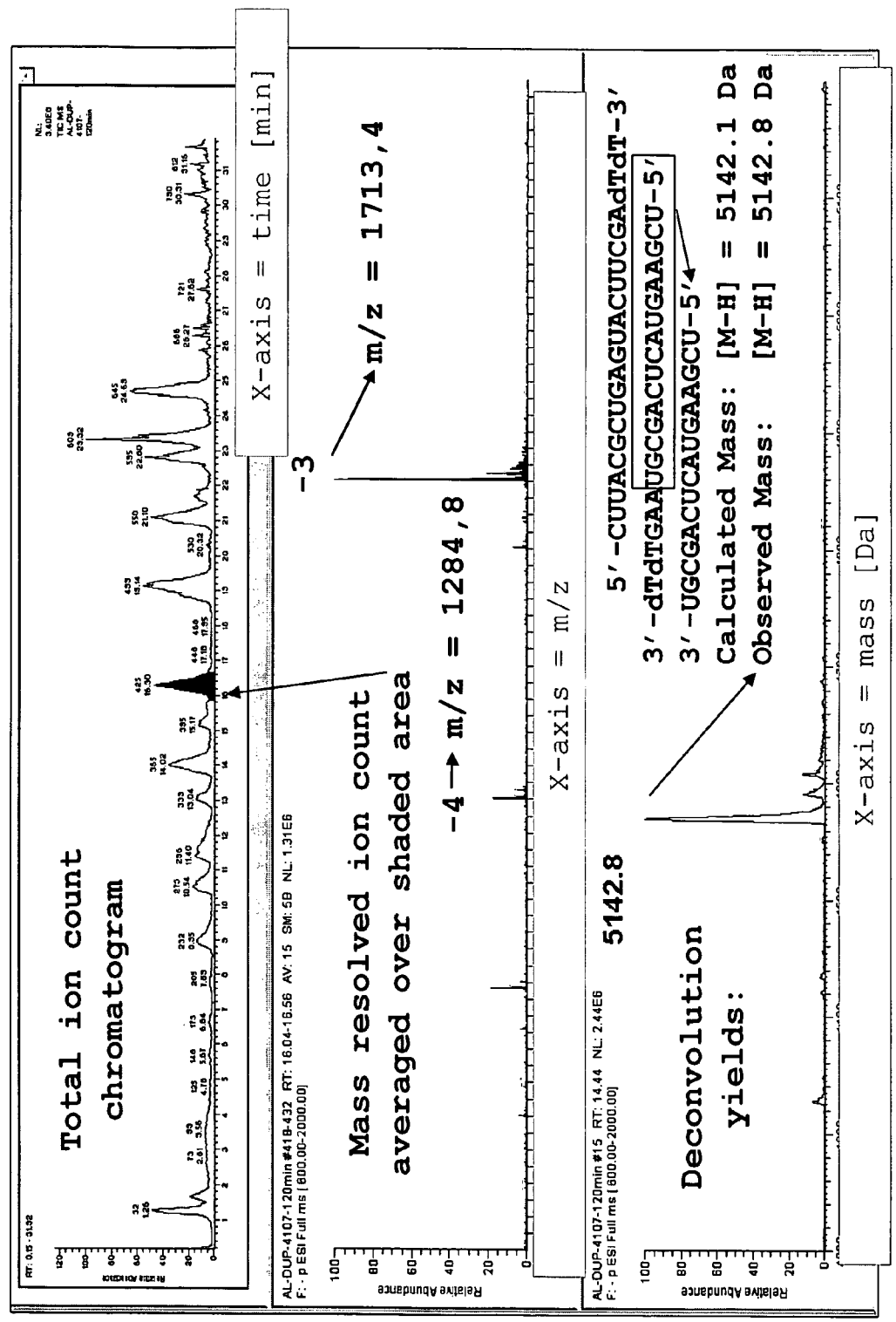
FIG. 22 shows in more detail the LC/MS analysis of fragments of dsRNA after incubation with serum. The upper panel depicts a plot of the total ion current measured by the mass spectrometer as a function of time; the peaks corresponding to the various RNA fragments of different lengths are clearly separated. The center panel depicts the result of a mass separation of ions generated from an RNA fragment appearing as one peak in the upper panel, plotting relative abundancy of ionic species vs. the mass to charge ratio of each ionic species. The lower panel shows the result of deconvoluting the data shown in the middle panel, i.e. correcting mass to charge for charge. The two main peaks at m/z=1284.8 and 1713,4 thereby collapse into a single peak corresponding to a mass of the parent RNA [M–H]=5142.8 DA. This observed mass corresponds within error limits to the predicted mass of the fragment 5'-ucgaaguacucagcgu-3' (SEQ. ID NO:1), which may be derived from the antisense strand of the dsRNA (SEQ. ID NO:185), (SEQ. ID NO:184) (referred to herein as LC1s/LC1 as by endonucleolytic cleavage of the 5'-ua-3' dinucleotide at positions 16-17.
Figures 23, 24, 25:
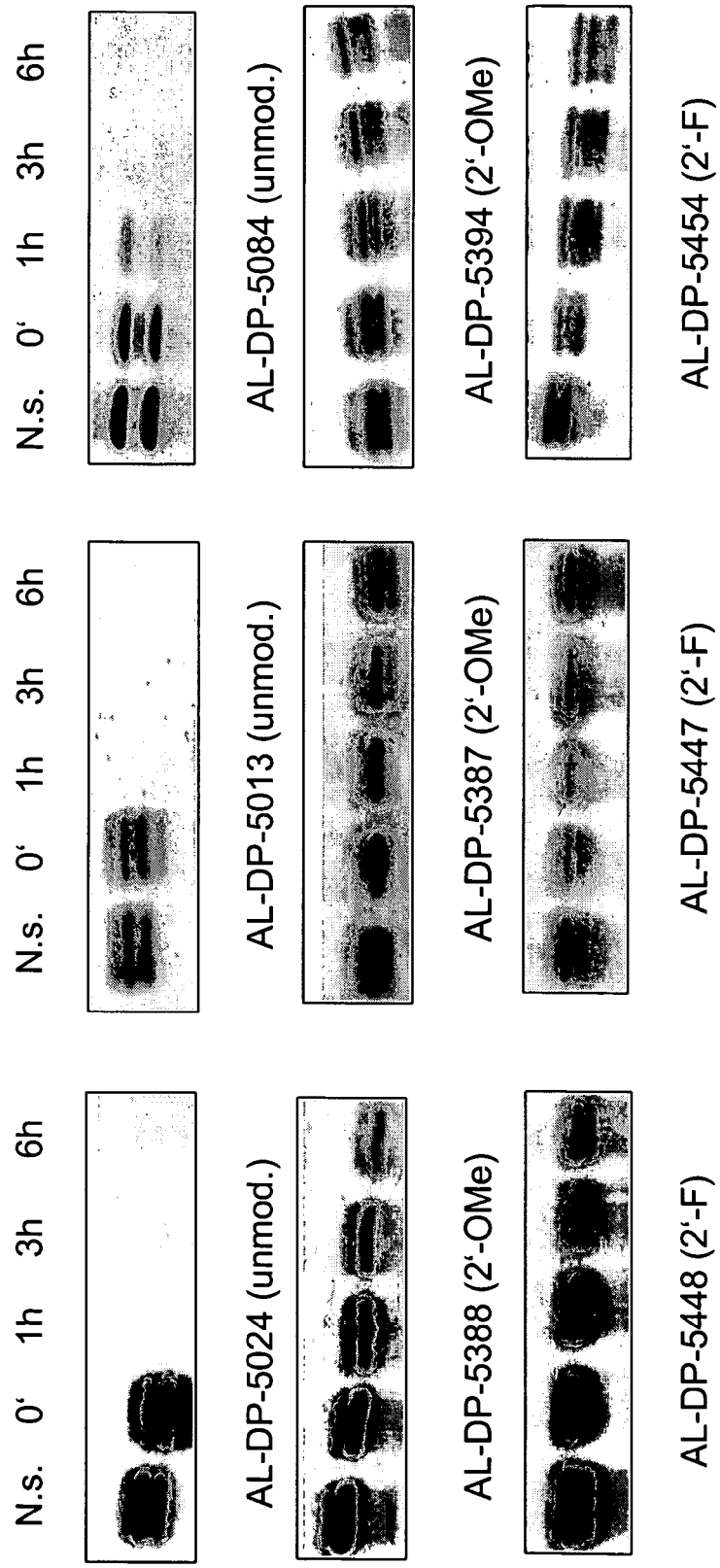
FIG. 23 shows a gel electrophoretic separation, stained using the "stains all" reagent, of the dsRNAs referred to herein as AL-DP-5024, AL-DP-5388, and AL-DP-5448 untreated (N.s.) or treated by incubation with human serum for 0, 1, 3, or 6 hours. These dsRNAs are identical in nucleotide sequence, except that AL-DP-5024 is an unmodified ribonucleotide, AL-DP-5388 bears 2'-O-methyl-modifications of the 5'-uridine or 5'-cytidine in all occurrences of the sequence motifs 5'-ua-3', 5'-ug-3', 5'-ca-3', and 5'-uu-3', as well as in positions 22 and 23 of the antisense strand, phosphorothioate linkages between positions 20 an 21 of the sense strand, and between positions 22 and 23 of the antisense strand (labeled "2'-OMe"), and AL-DP-5448 bears 2'-deoxy-2'-fluoro-modifications of the 5'-uridine or 5'-cytidine in all occurrences of the sequence motifs 5'-ua-3', 5'-ug-3', 5'-ca-3', and 5'-uu-3',2'-O-methyl-modifications in positions 22 and 23 of the antisense strand unless already 2'-deoxy-2'-fluoro-modified, phosphorothioate linkages between positions 20 an 21 of the sense strand, and between positions 22 and 23 of the antisense strand (labeled "2'-F").
FIG. 24 shows a gel electrophoretic separation, stained using the "stains all" reagent, of the dsRNAs referred to herein as AL-DP-5013, AL-DP-5387, and AL-DP-5447 untreated (N.s.) or treated by incubation with human serum for 0, 1, 3, or 6 hours. Labels "2'-OMe" and "2'-F" have the meaning as described for FIG. 23.
FIG. 25 shows a gel electrophoretic separation, stained using the "stains all" reagent, of the dsRNAs referred to herein as AL-DP-5084, AL-DP-5394, and AL-DP-5454, untreated (N.s.) or treated by incubation with human serum for 0, 1, 3, or 6 hours. Labels "2'-OMe" and "2'-F" have the meaning as described for FIG. 23.
Figures 26, 27, 28:
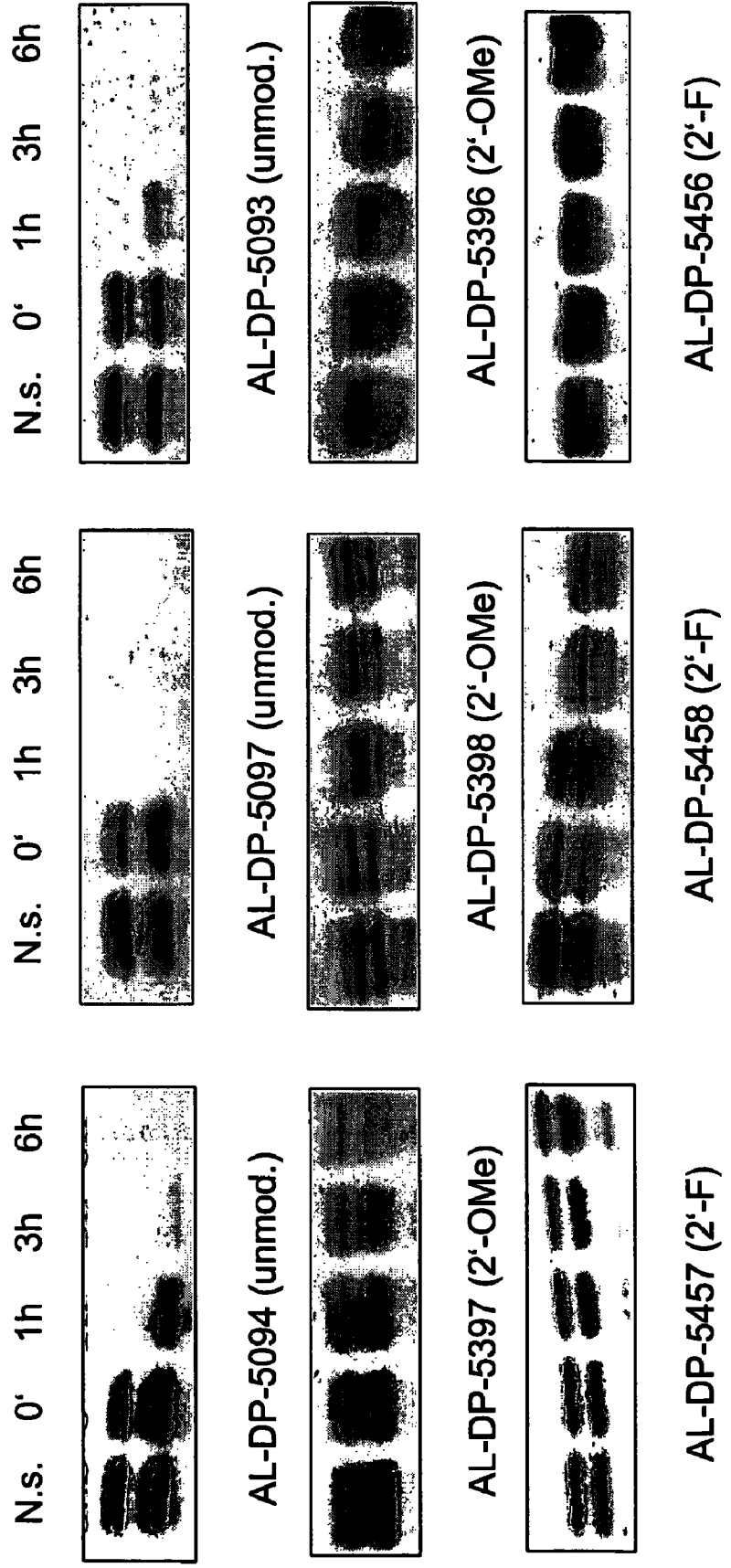
FIG. 26 shows a gel electrophoretic separation, stained using the "stains all" reagent, of the dsRNAs referred to herein as AL-DP-5094, AL-DP-5397, and AL-DP-5457 untreated (N.s.) or treated by incubation with human serum for 0, 1, 3, or 6 hours. Labels "2'-OMe" and "2'-F" have the meaning as described for FIG. 23.
FIG. 27 shows a gel electrophoretic separation, stained using the "stains all" reagent, of the dsRNAs referred to herein as AL-DP-5097, AL-DP-5398, and AL-DP-5458 untreated (N.s.) or treated by incubation with human serum for 0, 1, 3, or 6 hours. Labels "2'-OMe" and "2'-F" have the meaning as described for FIG. 23.
FIG. 28 shows a gel electrophoretic separation, stained using the "stains all" reagent, of the dsRNAs referred to herein as AL-DP-5093, AL-DP-5396, and AL-DP-5456 untreated (N.s.) or treated by incubation with human serum for 0, 1, 3, or 6 hours. Labels "2'-OMe" and "2'-F" have the meaning as described for FIG. 23.
Figures 32, 33, 34:
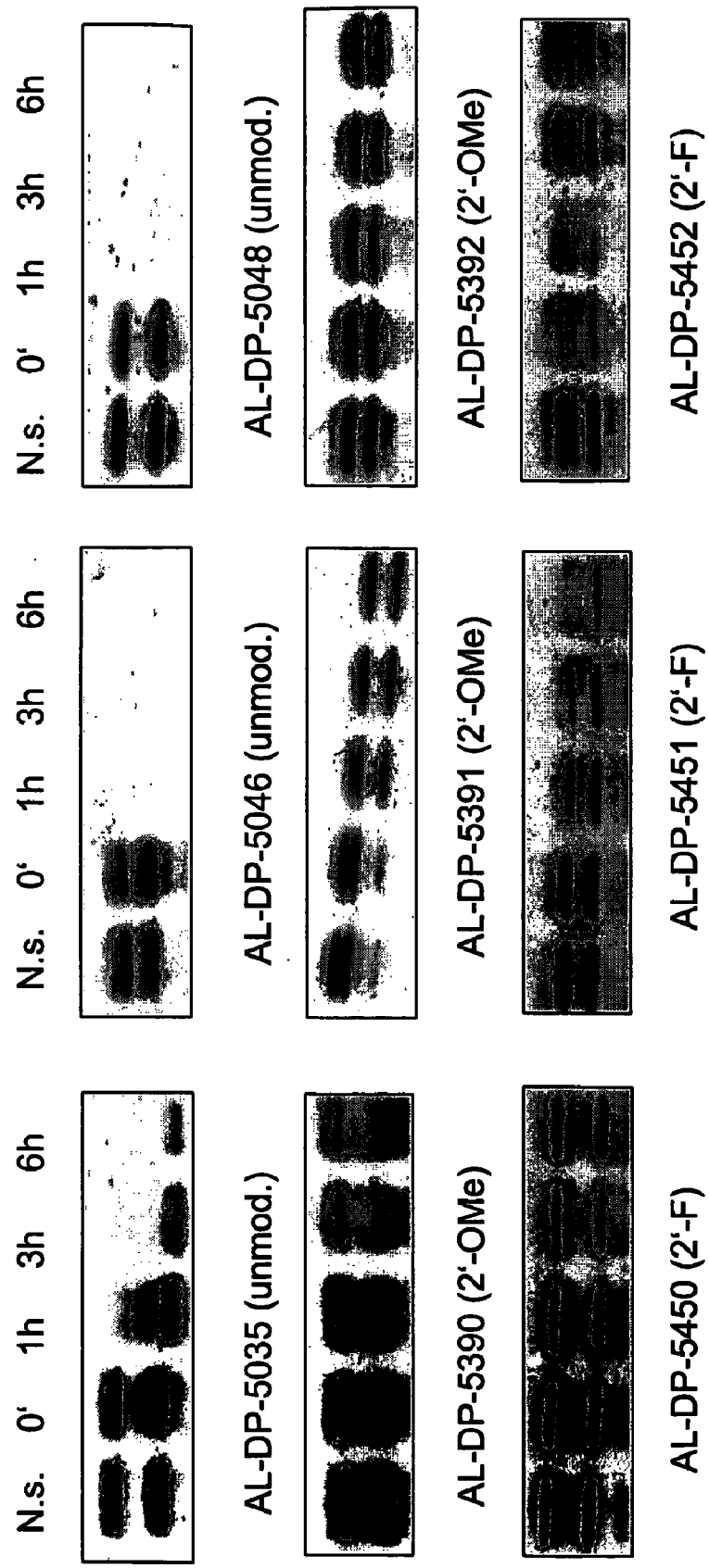
FIG. 32 shows a gel electrophoretic separation, stained using the "stains all" reagent, of the dsRNAs referred to herein as AL-DP-5035, AL-DP-5390, and AL-DP-5450 untreated (N.s.) or treated by incubation with human serum for 0, 1, 3, or 6 hours. Labels "2'-OMe" and "2'-F" have the meaning as described for FIG. 23.
FIG. 33 shows a gel electrophoretic separation, stained using the "stains all" reagent, of the dsRNAs referred to herein as AL-DP-5046, AL-DP-5391, and AL-DP-5451 untreated (N.s.) or treated by incubation with human serum for 0, 1, 3, or 6 hours. Labels "2'-OMe" and "2'-F" have the meaning as described for FIG. 23.
FIG. 34 shows a gel electrophoretic separation, stained using the "stains all" reagent, of the dsRNAs referred to herein as AL-DP-5048, AL-DP-5392, and AL-DP-5452 untreated (N.s.) or treated by incubation with human serum for 0, 1, 3, or 6 hours. Labels "2'-OMe" and "2'-F" have the meaning as described for FIG. 23.
Figure 36:
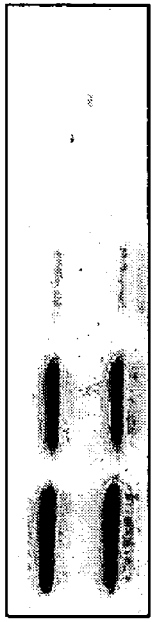
FIG. 36 shows a gel electrophoretic separation, stained using the "stains all" reagent, of the dsRNAs referred to herein as AL-DP-5049, AL-DP-5393, and AL-DP-5453 untreated (N.s.) or treated by incubation with human serum for 0, 1, 3, or 6 hours. Labels "2'-OMe" and "2'-F" have the meaning as described for FIG. 23.
Figure 36:
Figure 36:
Figure 35:
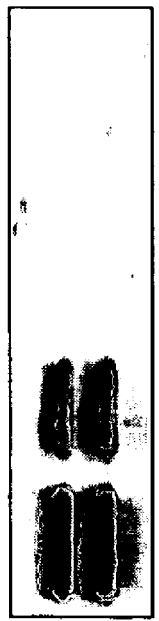
FIG. 35 shows a gel electrophoretic separation, stained using the "stains all" reagent, of the dsRNAs referred to herein as AL-DP-5002, AL-DP-5386, and AL-DP-5446 untreated (N.s.) or treated by incubation with human serum for 0, 1, 3, or 6 hours. Labels "2'-OMe" and "2'-F" have the meaning as described for FIG. 23.
Figure 35:

The unmodified all-ribo dsRNA GE1s/GE1as was completely degraded within 15 minutes (see FIG. 5). Even in the sample taken immediately after bringing the dsRNA into contact with the serum, the upper band corresponding to the antisense strand had already almost completely disappeared. By replacing all uridine nucleotides with 2'-O-methyl modified uridines, the GE7s/GE7as dsRNA was stabilized such that an appreciable amount was still detectable after a 4 hour incubation in serum. Even after 24 h in serum, trace amounts of the undegraded strands were still visible.

Introduction of two more 2'-O-methyl nucleotides at position 21 (G) and 22 (C) in the single stranded 3'-overhang of the antisense strand, as in case of GE7s/GE8s, further enhanced stability, as evidenced by the stronger bands corresponding to undegraded strands at the 1, 2, and 4 hour time points. Additionally introducing phosphorothioate linkages between position 21 and 22 of the antisense strand GE9as of the dsRNA GE7s/GE9as efficiently inhibited the exonucleolytic degradation of this strand.

The stabilizing contribution of 2'-O-methyl could be shown to be sequence dependent. By a stepwise removal of 2'-O-methyl uridines the crucial sequence context could be identified as sequences of 5'-ua-3'. In GE7s/GE10as, position 8 in the anti-sense strand contains a regular uridine residue. After 30 minutes in the serum incubation assay a degraded species could be detected which resulted from an endonucleolytic degradation process between positions 7 and 8 of the antisense strand. In the GE7s/GE1as dsRNA, this position is substituted by a 2'-O-methyl uridine and, consequently, the formation of the aforementioned degradation product could not be observed. Furthermore, two positions in GE7s/GE11as, namely positions 6 and 20, demonstrated that uridines in a 5'-AU-3' sequence context need not necessarily be exchanged by 2'-O-methyl uridines in order to enhance resistance towards degradation by nucleases. Duplexes of unmodified GE1s with the modified antisense strands GE7as, GE8as; GE9as; GE10as and GE11as, respectively, were rapidly degraded demonstrating the requirement that both strands need to be modified for an enhanced stability (see FIGS. 10-14). The rapid degradation of GE7s/GE1as revealed that the same requirements are valid for the protection of the antisense strand from degradation.

8.2 Results of Separation and Identification of dsRNA Fragments by LC/MS

Analysis of the serum degradation fragments of duplex LC1s/LC1as after incubation with mouse serum using LC/MS yielded the fragments listed in Table 5 and Table 6.

TABLE 5

Fragments identified by LC/MS after mouse serum incubation of LC1s/LC1as derived from the antisense strand 5'-ucgaaguacucagcguaagTT-3' (SEQ ID NO: 11); predicted mass [M − H] = 6692.1 Da

| Position | Sequence | 2'/3' terminal phosphate | pred. Mass | obs. Mass | SEQ ID NO: |
|---|---|---|---|---|---|
| U1-T20 | ucgaaguacucagcguaagT | No | 6387.9 | 6386.0 | 112 |
| U1-G19 | ucgaaguacucagcguaag | No | 6083.8 | 6080.7 | 113 |
| U1-U16 | ucgaaguacucagcgu | No | 5160.1 | 5160.6 | 114 |
| U1-U16 | ucgaaguacucagcgu-tp | cyclic | 5142.1 | 5142.1 | 115 |
| U1-U7 | ucgaagu-tp | cyclic | 2265.4 | 2265.5 | 116 |
| A17-T21 | aagTT | No | 1549.0 | 1549.1 | 117 |

TABLE 6

Fragments identified by LC/MS after mouse serum incubation of LC1s/LC1as derived from the sense strand 5'-cuuacgcugaguacuucgaTT-3' (SEQ ID NO: 10); predicted mass [M − H] = 6606.0 Da

| Position | Sequence | 2'/3' terminal phosphate | pred. Mass | obs. Mass | SEQ ID NO |
|---|---|---|---|---|---|
| C1-T20 | cuuacgcugaguacuucgaT | no | 6301.8 | 6301.1 | 118 |
| C1-A19 | cuuacgcugaguacuucga | no | 6083.8 | 6080.7 | 119 |
| A4-T21 | acgcugaguacuucgaTT | no | 5688.5 | 5688.8 | 120 |
| A4-T20 | acgcugaguacuucgaT | no | 5384.4 | 5385.9 | 121 |
| A4-U12 | acgcugagu-tp | cyclic | 2915.8 | 2916.1 | 122 |

Thus, the main sites of endonucleolytic cleavage identified by LC/MS in LC1s/LC1as were the dinucleotides 5'-ua-3' in positions 7-8 and 16-17 of the antisense strand, and positions 4-5 and 12-13 in the sense strand, counting from the 5'-end of the respective strand. In addition, stepwise exonucleolytic cleavage of the 3'-TT-overhangs was detected in both strands.

Analysis of the serum degradation fragments of duplex LC1s/LC1as using LC/MS yielded the fragments listed in Table 7 and Table 8.

TABLE 7

Fragments identified by LC/MS after mouse serum incubation of LC2s/LC2as derived from the antisense strand $^u$uggugagguuugauccgcTT (SEQ ID NO: 13); calculated Mass: [M − H] = 6679.0 Da

| Position | Sequence | 2'/3' terminal phosphate | pred. Mass | obs. Mass | SEQ ID NO: |
|---|---|---|---|---|---|
| u2-T21 | $^u$uggugagguuugauccgcTT | no | 6376.8 | 6373.8 | 123 |
| u1-T20 | $^u$uggugagguuugauccgcT | no | 6374.8 | 6373.8 | 124 |
| u1-c19 | $^u$uggugagguuugauccgc | no | 6070.6 | 6070.5 | 125 |
| u2-T20 | $^u$uggugagguuugauccgcTT | no | 6068.7 | 6070.5 | 126 |
| g3-T21 | $^g$gugagguuugauccgcTT | no | 6066.7 | 6067 | 127 |
| g3-T20 | $^g$gugagguuugauccgcT | no | 5762.5 | 5763 | 128 |
| u5-T20 | $^u$gagguuugauccgcT | no | 5072.1 | 5071 | 129 |
| g6-T21 | $^g$agguuugauccgcTT | no | 5070.1 | 5071 | 130 |
| u1-u11 | $^u$uggugagguu-tp | 2'-/3'-phosphate | 3603.1 | 3605 | 131 |
| u1-u11 | $^u$uggugagguu-tp | cyclic | 3585.1 | 3586.8 | 132 |
| u1-u10 | $^u$uggugaggu-tp | 2'-/3'-phosphate | 3297 | 3298.5 | 133 |
| u1-u10 | $^u$uggugaggu-tp | cyclic | 3279 | 3280 | 134 |
| u12-T21 | $^u$gauccgcTT | no | 3093 | 3094 | 135 |
| g3-u11 | $^g$gugagguu-tp | 2'-/3'-phosphate | 2990.8 | 2993 | 136 |
| g3-u11 | $^g$gugagguu-tp | cyclic | 2972.8 | 2974.3 | 137 |
| u12-T20 | $^u$gauccgcT | no | 2788.7 | 2788 | 138 |
| g13-T21 | $^g$auccgcTT | no | 2786.8 | 2788 | 139 |
| g6-u12 | $^g$agguuu-tp | cyclic | 2282.3 | 2282 | 140 |
| u5-u11 | $^u$gagguu-tp | cyclic | 2282.3 | 2282 | 141 |

TABLE 8

Fragments identified by LC/MS after mouse serum incubation of LC2s/LC2as derived from the sense strand $^g$cggaucaaaccucaccaaTT (SEQ ID NO: 12); calculated Mass: [M − H] = 6635.1 Da

| Position | Sequence | 2'/3' terminal phosphate | cal. Mass | exp. Mass | SEQ ID NO: |
|---|---|---|---|---|---|
| g1-T20 | $^g$cggaucaaaccucaccaaT | no | 6329.9 | 6330.5 | 142 |
| g1-c17 | $^g$cggaucaaaccucacc | cyclic | 5429.3 | 5429.4 | 143 |
| g1-c16 | $^g$cggaucaaaccucac | cyclic | 5124.1 | 5124.8 | 144 |
| g1-c14 | $^g$cggaucaaaccuc | cyclic | 4489.8 | 4490 | 145 |

TABLE 8-continued

Fragments identified by LC/MS after mouse serum incubation of LC2s/LC2as derived from the sense strand gcggaucaaaccucaccaaTT (SEQ ID NO: 12); calculated Mass: [M - H] = 6635.1 Da

| Position | Sequence | 2'/3' terminal phosphate | cal. Mass | exp. Mass | SEQ ID NO: |
|---|---|---|---|---|---|
| c7-T20 | caaaccucaccaaT | no | 4353.8 | 4354 | 146 |
| a8-T21 | aaaccucaccaaTT | no | 4352.8 | 4354 | 147 |
| c7-a19 | caaaccucaccaa | no | 4049.5 | 4050 | 148 |
| a8-T20 | aaaccucaccaaT | no | 4048.5 | 4050 | 149 |
| a8-c17 | aaaccucacc | cyclic | 3147.9 | 3149 | 150 |
| c7-c16 | caaaccucac | cyclic | 3147.9 | 3149 | 151 |
| a8-c16 | aaaccucac | cyclic | 2842.8 | 2843.8 | 152 |
| g1-c7 | gcggauc | cyclic | 2280.4 | 2282 | 153 |
| a8-c14 | aaaccuc | cyclic | 2208.4 | 2209.3 | 154 |
| g1-u6 | gcggau | cyclic | 1975.2 | 1977 | 155 |

Table 7 shows that LC2s/LC2as was subject to some exonucleolytic degradation. The fragments corresponding to u2-T21/u1-T20 and u2-T20/u1-c19 cannot be unequivocally assigned due to their small mass difference of 2 Da, but the observed mass is closer to the u1-T20 and u1-c19. Hence, it seems likely that exonucleases present in mouse serum are able to degrade the terminal TT single strand overhang. Exonucleolytic activity in mouse serum was generally greater than in human serum.

LC2s/LC2as was chosen for analysis partly because its sense strand does not comprise the 5'-ua-3' motif, and therefore could potentially yield information on other sequence motifs prone to endonucleolytic attack. Indeed, the fragments g3-T21, g3-T20, g3-u11, g6-T21, g6-u12, and g13-T21 point towards 5'-ug-3' as a point of efficient degradative action by endonucleases. Similarly, the fragments u1-u10, u1-u11, both involving a terminal phosphate, and u12-u21 indicate 5'-uu-3' as a third motif of endonucleolysis. In a different experiment (data not shown), 5'-ca-3', 5'-cc-3', 5'-cu-3' and 5'-uc-3' were further shown occasionally to be targets of endonucleolytic degradation.

Accordingly, a number of siRNA duplexes were synthesized, wherein the pyrimidine nucleotides present in a sequence context of 5'-ua-3', 5'-ug-3' and 5'-uu-3' were protected towards endonucleolytic degradation by 2'-O-methyl modifications. In addition, for incubation with mouse serum, the 3'-terminus of the sense strand was protected against exonucleolytic degradation by conjugation to a cholesteryl moiety via a pyrrolidinyl phosphorothiodiester. AL-DP 5542 is identical in sequence to AL-DP 5543 but for these potentially stabilizing 2'-modifications in AL-DP 5542. AL-DP 5544 is identical in sequence to AL-DP 5545 but for the same potentially stabilizing 2'-modifications in AL-DP 5544.

Degradation half lives were determined for each of the RNA strands of AL-DP 5542, AL-DP 5543, AL-DP 5544, and AL-DP 5545 as described under section 6 above. Results are given Table 9.

TABLE 9

Half life in hours for the degradation of individual strands of AL-DP 5542, AL-DP 5543, AL-DP 5544, and AL-DP 5545 measured by HPLC after incubation of the RNA duplex with mouse serum

| Half life in mouse serum (hours) | AL-DP 5542 | AL-DP 5543 | AL-DP 5544 | AL-DP 5545 |
|---|---|---|---|---|
| sense strand | 36 | 1.6 | 21 | 3.6 |
| antisense strand | 8 | 0.5 | 19 | 8 |

Table 9 shows, that the 2'-modification of nucleotides in sequence contexts making them prone to degradation led to a stabilization of the individual strands by a factor between about 2 and about 20.

By replacement of all 5'-u and 5'-c in sequence motifs 5'-ua-3', 5'-ug-3', 5'-ca-3', 5'-uu-3', 5'-uc-3', 5'-cc-3', and 5'-cu-3' siRNA duplexes with very high stability towards endonucleolytic degradation could be generated. By stepwise replacement of first all 5'-U and 5'-C in sequence motifs 5'-ua-3', then, for example, all 5'-u in sequence motifs 5'-ug-3', then, for example, all 5'-c in sequence motifs 5'-ca-3', then, for example, all 5'-u in sequence motifs 5'-uu-3', then, for example, all 5'-u in sequence motifs 5'-uc-3', then, for example, all 5'-u in sequence motifs 5'-cc-3', and lastly for example, all 5'-c in sequence motifs 5'-cu-3', intermediately assessing stability towards nucleolytic degradation in serum, it was possible to tailor-make dsRNA duplexes with a certain desired stability in serum. Where it was necessary to keep the number of modifications to a minimum in order to preserve the activity of a certain siRNA for inhibition of target gene expression while attaining a certain minimum stability, this stepwise approach was successfully applied by replacing only the most vulnerable sites with modified nucleotides until the best compromise between stability and activity was obtained.

8.3 Stability and Activity of siRNAs Bearing 2'-Modifications in 5'-Uridines and 5'-Cytidines in Sequence Motifs 5'-ua-3', 5'-ug-3', 5'-ca-3', and 5'-uu-3'

Good stability with reasonable or no loss of gene expression inhibiting activity compared to the all-ribonucleotide sequence was usually obtained when modifying 5'-uridines and 5'-cytidines in sequence motifs 5'-ua-3', 5'-ug-3', 5'-ca-3', and 5'-uu-3'.

FIG. 23 to FIG. 36 show comparisons of the stability of siRNAs AL-DP-5097, AL-DP-5398, AL-DP-5458, AL-DP-5098, AL-DP-5399, AL-DP-5459, AL-DP-5024, AL-DP-5388, AL-DP-5448, AL-DP-5013, AL-DP-5387, AL-DP-5447, AL-DP-5084, AL-DP-5394, AL-DP-5454, AL-DP-5094, AL-DP-5397, AL-DP-5457, AL-DP-5093, AL-DP-5396, AL-DP-5456, AL-DP-5089, AL-DP-5395, AL-DP-5455, AL-DP-5030, AL-DP-5389, AL-DP-5449, AL-DP-5035, AL-DP-5390, AL-DP-5450, AL-DP-5046, AL-DP-5391, AL-DP-5451, AL-DP-5048, AL-DP-5392, AL-DP-5452, AL-DP-5002, AL-DP-5386, AL-DP-5446, AL-DP-5049, AL-DP-5393, and AL-DP-5453, after incubation with human serum and analysis by electrophoresis and "stains all" detection. Table 10 lists the corresponding activities of these siRNAs towards the reduction of ApoB mRNA concentrations present in cultured HepG2 cells as compared to cells incubated with unrelated siRNA AL-DP-HCV.

FIG. 23 to FIG. 36 show that the unmodified siRNAs AL-DP-5097, AL-DP-5098, AL-DP-5024, AL-DP-5013, AL-DP-5084, AL-DP-5094, AL-DP-5093, AL-DP-5089, AL-DP-5030, AL-DP-5035, AL-DP-5046, AL-DP-5048, AL-DP-5002, and AL-DP-5049 are degraded very quickly, such that after 1 hour of serum incubation, virtually no full length strands are detectable. By contrast, the corresponding modified siRNAs show a marked increase in stability under the conditions of serum incubation, full length sense and antisense strands remaining almost undegraded for at least 6 hours of incubation.

TABLE 10

Activities of siRNAs bearing various modifications towards the reduction of ApoB mRNA concentrations present in cultured HepG2 cells as compared to cells incubated with unrelated siRNA AL-DP-HCV

| Duplex Descriptor | Start codon of sequence in ApoB mRNA complementary to antisense strand | ApoB mRNA remaining in cells incubated with siRNA in % of control[a] | Modification pattern[b] |
|---|---|---|---|
| AL-DP-5024 | 465 | 13 | Unmodified |
| AL-DP-5388 | " | 17 | 2'-O-methyl |
| AL-DP-5448 | " | 20 | 2'-deoxy-2'-fluoro |
| AL-DP-5013 | 466 | 17 | Unmodified |
| AL-DP-5387 | " | 40 | 2'-O-methyl |
| AL-DP-5447 | " | 24 | 2'-deoxy-2'-fluoro |
| AL-DP-5084 | 623 | 36 | Unmodified |
| AL-DP-5394 | " | 36 | 2'-O-methyl |
| AL-DP-5454 | " | 68 | 2'-deoxy-2'-fluoro |
| AL-DP-5094 | 1287 | 23 | Unmodified |
| AL-DP-5397 | " | 42 | 2'-O-methyl |
| AL-DP-5457 | " | n.d. | 2'-deoxy-2'-fluoro |
| AL-DP-5097 | 1296 | 15 | Unmodified |
| AL-DP-5398 | " | 21 | 2'-O-methyl |
| AL-DP-5458 | " | 19 | 2'-deoxy-2'-fluoro |
| AL-DP-5093 | 1339 | 26 | Unmodified |
| AL-DP-5396 | " | 93 | 2'-O-methyl |
| AL-DP-5456 | " | 35 | 2'-deoxy-2'-fluoro |
| AL-DP-5098 | 2133 | 21 | Unmodified |
| AL-DP-5399 | " | 20 | 2'-O-methyl |
| AL-DP-5459 | " | 26 | 2'-deoxy-2'-fluoro |
| AL-DP-5089 | 2807 | 32 | Unmodified |
| AL-DP-5395 | " | 25 | 2'-O-methyl |
| AL-DP-5455 | " | 34 | 2'-deoxy-2'-fluoro |
| AL-DP-5030 | 2866 | 12 | Unmodified |
| AL-DP-5389 | " | 41 | 2'-O-methyl |
| AL-DP-5449 | " | 18 | 2'-deoxy-2'-fluoro |
| AL-DP-5035 | 2869 | 17 | Unmodified |
| AL-DP-5390 | " | 21 | 2'-O-methyl |
| AL-DP-5450 | " | 22 | 2'-deoxy-2'-fluoro |
| AL-DP-5046 | 10180 | 19 | Unmodified |
| AL-DP-5391 | " | 45 | 2'-O-methyl |
| AL-DP-5451 | " | 42 | 2'-deoxy-2'-fluoro |
| AL-DP-5048 | 10187 | 19 | Unmodified |
| AL-DP-5392 | " | 45 | 2'-O-methyl |
| AL-DP-5452 | " | 26 | 2'-deoxy-2'-fluoro |
| AL-DP-5002 | 13539 | 19 | Unmodified |
| AL-DP-5386 | " | 54 | 2'-O-methyl |
| AL-DP-5446 | " | 21 | 2'-deoxy-2'-fluoro |
| AL-DP-5049 | 13550 | 24 | Unmodified |
| AL-DP-5393 | " | 69 | 2'-O-methyl |
| AL-DP-5453 | " | 41 | 2'-deoxy-2'-fluoro |

[a]n.d. not determined
[b]2'-O-methyl = 2'-O-methyl-modifications of the 5'-uridine or 5'-cytidine in all occurrences of the sequence motifs 5'-ua-3', 5'-ug-3', 5'-ca-3', and 5'-uu-3', as well as in positions 22 and 23 of the antisense strand, phosphorothioate linkages between positions 20 an 21 of the sense strand, and between positions 22 and 23 of the antisense strand; 2'-deoxy-2'-fluoro: 2'-deoxy-2'-fluoro-modifications of the 5'-uridine or 5'-cytidine in all occurrences of the sequence motifs 5'-ua-3', 5'-ug-3', 5'-ca-3', and 5'-uu-3', 2'-O-methyl-modifications in positions 22 and 23 of the antisense strand unless already 2'-deoxy-2'-fluoro-modified, phosphorothioate linkages between positions 20 an 21 of the sense strand, and between positions 22 and 23 of the antisense strand At the same time, Table 10 shows that the gene silencing activity of the so modified siRNAs is only slightly to moderately reduced, where the 2'-O-methyl modification may have a slightly greater impact than the 2'-deoxy-2'-fluoro-modification.

We claim:

1. A double-stranded ribonucleic acid (dsRNA) having increased stability in a biological sample, wherein the dsRNA comprises:
   (I) a nucleotide overhang having the nucleotide sequence 5'-GCNN-3', wherein N is A, G, C, U, dT, dU or absent; and
   (II) at least one of
      (a) 2'-modified uridines in all occurrences of the sequence motif 5'-uridine-adenine-3' (5'-ua-3'), or
      (b) 2'-modified uridines in all occurrences of the sequence motif 5'-uridine-guanine-3' (5'-ug-3'), or
      (c) 2'-modified 5'-most uridines in all occurrences of the sequence motif 5'-uridine-uridine-3' (5' -uu-3'), or
      (d) 2'-modified uridines in all occurrences of the sequence motif 5'-uridine-cytidine-3' (5' -uc-3'), or
      (e) 2'-modified cytidines in all occurrences of the sequence motif 5'-cytidine-adenine-3' (5'-ca-3'), or
      (f) 2'-modified cytidines in all occurrences of the sequence motif 5'-cytidine-uridine-3' (5'-cu-3'), or
      (g) 2'-modified 5'-most cytidines in all occurrences of the sequence motif 5'-cytidine-cytidine-3' (5'-cc-3').

2. The dsRNA of claim 1, wherein the first paired nucleotide on the 5'-end of the 5'-GCNN-3' overhang is cytidine (C).

3. The dsRNA of claim 1, wherein the unpaired nucleotides comprise at least one phosphorothioate dinucleotide linkage.

4. The dsRNA of claim 1, wherein nucleotide overhang is at the 3'-end of the antisense RNA strand of the dsRNA.

5. The dsRNA of claim 1, wherein the antisense RNA strand of the dsRNA comprises a nucleotide sequence 18-30 nucleotides in length which is complementary to the sense strand.

6. The dsRNA of claim 1, wherein the antisense and sense RNA strands of the dsRNA are connected by a chemical linker.

7. A method of preparing a pharmaceutical composition, comprising formulating the dsRNA of claim 1, in a pharmaceutically acceptable carrier.

8. A pharmaceutical composition for inhibiting the expression of a target gene in a mammal, comprising:
   (A) at least one dsRNA of claim 1; and
   (B) a pharmaceutical acceptable carrier.

9. The pharmaceutical composition of claim 8, wherein the pharmaceutically acceptable carrier is an aqueous solution.

10. The pharmaceutical composition of claim 8, wherein the pharmaceutically acceptable carrier is physiological saline.

11. The dsRNA of claim 1, wherein the dsRNA comprises at least two different features of the features (a) through (g).

12. The dsRNA of claim 1, wherein the dsRNA comprises at least three different features of the features (a) through (g).

13. The dsRNA of claim 1, wherein the dsRNA comprises at least four different features of the features (a) through (g).

14. The dsRNA of claim 13, wherein the four different features dsRNA comprises at least four different features of the features (a), (b), (c) and (e).

15. The dsRNA of claim 1, wherein the dsRNA comprises at least five different features of the features (a) through (g).

16. The dsRNA of claim 1, wherein the dsRNA comprises at least two occurrences of at least one of the sequence motifs of (a) through (g).

17. The dsRNA of claim 1, wherein the dsRNA comprises at least three occurrences of at least one of the sequence motifs of (a) through (g).

18. The dsRNA of claim 1, further comprising at least one dinucleotide selected from group of 5'-uu-3', 5'-ua-3', 5'-ug-3', 5'-uc-3', 5'-cu-3', 5'-ca-3', 5'-cg-3', 5'-cc-3', wherein no nucleotide is a 2'-O-modified nucleotide.

19. The dsRNA of claim 1, wherein the 2'-modified nucleotide is a 2'-deoxy nucleotide, a 2'-O-methyl nucleotide, a 2'-deoxyfluoro nucleotide, a 2'-O- methoxyethyl (2'-MOE)) nucleotide, a 2'-O-methylacetamido (2'-NMA), a 2'-O- dimethyl-amino-ethoxy-ethyl nucleotide, a 2'-O-dimethylaminopropyl (2'-O-AP) nucleotide, 2'-ara-F nucleotide, or a locked nucleic acid nucleotide, extended nucleic acid nucleotide, a hexose nucleic acid, or cyclohexose nucleic acid.

* * * * *

SEQUENCE LISTING

<160> NUMBER OF SEQ ID NOS: 185

<210> SEQ ID NO 1
<211> LENGTH: 16
<212> TYPE: RNA
<213> ORGANISM: Artificial Sequence
<220> FEATURE:
<223> OTHER INFORMATION: Synthetically generated oligonucleotide

<400> SEQUENCE: 1

-continued ucgaaguacu cagcgu                                           16

<210> SEQ ID NO 2
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 2
gaucacccuc cuuaaauauu u                                     21

<210> SEQ ID NO 3
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 3
uucuagaggg aggaauuuau aaa                                   23

<210> SEQ ID NO 4
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 9, 12, 13, 17, 19, 20, 21
<223> OTHER INFORMATION: n = 2'-O-methyluridine-5'-monophosphate

<400> SEQUENCE: 4 gancaccenc cnnaaananu n                                     21

<210> SEQ ID NO 5
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 7, 16, 17, 18, 20
<223> OTHER INFORMATION: n = 2'-O-methyluridine-5'-monophosphate

<400> SEQUENCE: 5
cgcnagnggg aggaannnan aaa                                   23

<210> SEQ ID NO 6
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2
<223> OTHER INFORMATION: n = 2'-O-methylguanosine-5'-monophosphate
<220> FEATURE:
<221> NAME/KEY: misc_feature
<222> LOCATION: 3
<223> OTHER INFORMATION: n = 2'-O-methylcytidine-5'-monophosphate
<220> FEATURE:
<221> NAME/KEY: misc_feature
<222> LOCATION: 4, 7, 16, 17, 18, 20
<223> OTHER INFORMATION: n = 2'-O-methyluridine-5'-monophosphate

<400> SEQUENCE: 6
cnnnagnggg aggaannnan aaa                                         23

```
<210> SEQ ID NO 7
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2
<223> OTHER INFORMATION: n = 2'-O-methyl-adenosine-5'-phosphorothioate
<220> FEATURE:
<221> NAME/KEY: misc_feature
<222> LOCATION: 3
<223> OTHER INFORMATION: n = 2'-O-methyl-cytidine-5'-phosphorothioate
<220> FEATURE:
<221> NAME/KEY: misc_feature
<222> LOCATION: 4, 7, 16, 17, 18, 20
<223> OTHER INFORMATION: n = 2'-O-methyluridine-5'-monophosphate

<400> SEQUENCE: 7
```
cnnnagnggg aggaannnan aaa                                         23

```
<210> SEQ ID NO 8
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2
<223> OTHER INFORMATION: n = 2'-O-methyl guanosine-5'-monophosphate
<220> FEATURE:
<221> NAME/KEY: misc_feature
<222> LOCATION: 3
<223> OTHER INFORMATION: n = 2'-O-methylcytidine-5'-monophosphate
<220> FEATURE:
<221> NAME/KEY: misc_feature
<222> LOCATION: 4, 18, 20
<223> OTHER INFORMATION: n = 2'-O-methyluridine-5'-monophosphate

<400> SEQUENCE: 8
```
cnnnaguggg aggaauunan aaa                                         23

```
<210> SEQ ID NO 9
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2
<223> OTHER INFORMATION: n = 2'-O-methyluridine-5'-monophosphate
<220> FEATURE:
<221> NAME/KEY: misc_feature
<222> LOCATION: 3
<223> OTHER INFORMATION: n = 2'-O-methylcytidine-5'-monophosphate
<220> FEATURE:
<221> NAME/KEY: misc_feature
<222> LOCATION: 16, 20
<223> OTHER INFORMATION: n = 2'-O-methyluridine-5'-monophosphate

<400> SEQUENCE: 9
```
cnnuaguggg aggaanuuan aaa                                         23

```
<210> SEQ ID NO 10
<211> LENGTH: 21
<212> TYPE: DNA
<213> ORGANISM: Artificial Sequence
```

```
<220> FEATURE:
<223> OTHER INFORMATION: Synthetically generated oligonucleotide

<400> SEQUENCE: 10
cuuacgcuga guacuucgat t                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 11
ucgaaguacu cagcguaagt t                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 12
gcggaucaaa ccucaccaat t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 13
ucgaaguacu cagcguaagt t                                              21

<210> SEQ ID NO 14
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 14
cuuuacaagc cuugguucag u                                              21

<210> SEQ ID NO 15
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 15
acugaaccaa ggcuuguaaa gug                                            23

<210> SEQ ID NO 16
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 3, 4, 12, 13, 16
<223> OTHER INFORMATION: n = 2'-O-methyluridine-5'-monophosphate
<220> FEATURE:
<221> NAME/KEY: misc_feature
```

```
<222> LOCATION: 6, 18
<223> OTHER INFORMATION: n = 2'-O-methylcytidine-5'-monophosphate

<400> SEQUENCE: 16
cnnnanaagc cnnggnunag u                                               21

<210> SEQ ID NO 17
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 15, 17
<223> OTHER INFORMATION: n = 2'-O-methyluridine-5'-monophosphate
<220> FEATURE:
<221> NAME/KEY: misc_feature
<222> LOCATION: 8
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 17
acngaacnaa ggcungnaaa gng                                             23

<210> SEQ ID NO 18
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 3, 4, 12, 13, 16
<223> OTHER INFORMATION: n = 2'-fluoro-2'-deoxy-uridine-5'-monophosphate
<220> FEATURE:
<221> NAME/KEY: misc_feature
<222> LOCATION: 6, 18
<223> OTHER INFORMATION: n = 2'-fluoro-2'-deoxy-cytidine-5'-
      monophosphate

<400> SEQUENCE: 18
cnnnanaagc cnnggnunag u                                               21

<210> SEQ ID NO 19
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 15, 17
<223> OTHER INFORMATION: n = 2'-fluoro-2'-deoxy-uridine-5'-monophosphate
<220> FEATURE:
<221> NAME/KEY: misc_feature
<222> LOCATION: 8
<223> OTHER INFORMATION: n = 2'-fluoro-2'-deoxy-cytidine-5'-
      monophosphate
<220> FEATURE:
<221> NAME/KEY: misc_feature
<222> LOCATION: 21
<223> OTHER INFORMATION: n = 2'-O-methylguanosine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 19
acngaacnaa ggcungnaaa nng                                             23
```

```
<210> SEQ ID NO 20
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 3, 4, 12, 13,  16
<223> OTHER INFORMATION: n = 2'-O-methyluridine-5'-monophosphate
<220> FEATURE:
<221> NAME/KEY: misc_feature
<222> LOCATION: 6, 18
<223> OTHER INFORMATION: n = 2'-O-methylcytidine-5'-monophosphate

<400> SEQUENCE: 20
cnnnanaagc cnnggnunag u                                              21

<210> SEQ ID NO 21
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 15, 17
<223> OTHER INFORMATION: n = 2'-O-methyluridine-5'-monophosphate
<220> FEATURE:
<221> NAME/KEY: misc_feature
<222> LOCATION: 8
<223> OTHER INFORMATION: n = 2'-O-methylcytidine-5'-monophosphate
<220> FEATURE:
<221> NAME/KEY: misc_feature
<222> LOCATION: 21
<223> OTHER INFORMATION: n = 2'-O-methylguanosine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 21
acngaacnaa ggcungnaaa nng                                            23

<210> SEQ ID NO 22
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 22
cuuuacaagc cuugguucag u                                              21

<210> SEQ ID NO 23
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = 2'-O-methylguanosine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 23
acugaaccaa ggcuuguaaa nng                                            23
```

```
<210> SEQ ID NO 24
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 24
ggaaucuuau auuugaucca a                                               21

<210> SEQ ID NO 25
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 25
uuggaucaaa uauaagauuc ccu                                             23

<210> SEQ ID NO 26
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 7, 8, 10, 12, 13, 14
<223> OTHER INFORMATION: n = 2'-O-methyluridine-5'-monophosphate
<220> FEATURE:
<221> NAME/KEY: misc_feature
<222> LOCATION: 19
<223> OTHER INFORMATION: n = 2'-O-methylcytidine-5'-monophosphate

<400> SEQUENCE: 26
ggaaucnnan annngaucna a                                               21

<210> SEQ ID NO 27
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 2, 11, 13, 18
<223> OTHER INFORMATION: n = 2'-O-methyluridine-5'-monophosphate
<220> FEATURE:
<221> NAME/KEY: misc_feature
<222> LOCATION: 7, 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 27
nnggaunaaa nanaaganuc nnu                                             23

<210> SEQ ID NO 28
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 7, 8, 10, 12, 13, 14
<223> OTHER INFORMATION: n = 2'-fluoro-2'-deoxy-uridine-5'-monophosphate
```

```
<220> FEATURE:
<221> NAME/KEY: misc_feature
<222> LOCATION: 19
<223> OTHER INFORMATION: n = 2'-fluoro-2'-deoxy-cytidine-5'-
      monophosphate

<400> SEQUENCE: 28
ggaaucnnan annngaucna a                                                21

<210> SEQ ID NO 29
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 2, 11, 13, 18
<223> OTHER INFORMATION: n = 2'-fluoro-2'-deoxy-uridine-5'-monophosphate
<220> FEATURE:
<221> NAME/KEY: misc_feature
<222> LOCATION: 7
<223> OTHER INFORMATION: n = 2'-fluoro-2'-deoxy-cytidine-5'-
      monophosphate
<220> FEATURE:
<221> NAME/KEY: misc_feature
<222> LOCATION: 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-cytidine-5'-phosphorothioate

<400> SEQUENCE: 29
nnggaunaaa nanaaganuc nnu                                              23

<210> SEQ ID NO 30
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 7, 8, 10, 12, 13, 14
<223> OTHER INFORMATION: n = 2'-O-methyluridine-5'-monophosphate
<220> FEATURE:
<221> NAME/KEY: misc_feature
<222> LOCATION: 19
<223> OTHER INFORMATION: n = 2'-O-methylcytidine-5'-monophosphate

<400> SEQUENCE: 30
ggaaucnnan annngaucna a                                                21

<210> SEQ ID NO 31
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = 2'-O-methyl-uridine (5'-hydroxyl)
<220> FEATURE:
<221> NAME/KEY: misc_feature
<222> LOCATION: 2, 11, 13, 18
<223> OTHER INFORMATION: n = 2'-O-methyluridine-5'-monophosphate
<220> FEATURE:
<221> NAME/KEY: misc_feature
<222> LOCATION: 7, 21
<223> OTHER INFORMATION: n = 2'-O-methylcytidine-5'-monophosphate
<220> FEATURE:
<221> NAME/KEY: misc_feature
```

```
<222> LOCATION: 22
<223> OTHER INFORMATION: n = 2'-O-methyl-cytidine-5'-phosphorothioate

<400> SEQUENCE: 31
nnggaunaaa nanaaganuc nnu                                              23

<210> SEQ ID NO 32
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 32
ggaaucuuau auugaucca a                                                 21

<210> SEQ ID NO 33
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-cytidine-5'-phosphorothioate

<400> SEQUENCE: 33
uuggaucaaa uauaagauuc nnu                                              23

<210> SEQ ID NO 34
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 34
agguguaugg cuucaacccu g                                                21

<210> SEQ ID NO 35
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 35
caggguugaa gccauacacc ucu                                              23

<210> SEQ ID NO 36
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 6, 8, 12,
<223> OTHER INFORMATION: n = 2'-O-methyluridine-5'-monophosphate
<220> FEATURE:
<221> NAME/KEY: misc_feature
<222> LOCATION: 14
<223> OTHER INFORMATION: n = 2'-O-methylcytidine-5'-monophosphate

<400> SEQUENCE: 36
```
aggngnangg cnunaacccu g                                    21

<210> SEQ ID NO 37
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 13, 17
<223> OTHER INFORMATION: n = 2'-O-methylcytidine-5'-monophosphate
<220> FEATURE:
<221> NAME/KEY: misc_feature
<222> LOCATION: 6, 7, 15, 21
<223> OTHER INFORMATION: n = 2'-O-methyluridine-5'-monophosphate
<220> FEATURE:
<221> NAME/KEY: misc_feature
<222> LOCATION: 22
<223> OTHER INFORMATION: n = 2'-O-methyl-cytidine-5'-phosphorothioate

<400> SEQUENCE: 37
nagggnngaa gcnananacc nnu                                  23

<210> SEQ ID NO 38
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 6, 8, 12
<223> OTHER INFORMATION: n = 2'-fluoro-2'-deoxy-uridine-5'-monophosphate
<220> FEATURE:
<221> NAME/KEY: misc_feature
<222> LOCATION: 14
<223> OTHER INFORMATION: n = 2'-fluoro-2'-deoxy-cytidine-5'-
      monophosphate

<400> SEQUENCE: 38
aggngnangg cnunaacccu g                                    21

<210> SEQ ID NO 39
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 13, 17
<223> OTHER INFORMATION: n = 2'-fluoro-2'-deoxy-cytidine-5'-
      monophosphate
<220> FEATURE:
<221> NAME/KEY: misc_feature
<222> LOCATION: 6, 7, 15
<223> OTHER INFORMATION: n = 2'-fluoro-2'-deoxy-uridine-5'-monophosphate
<220> FEATURE:
<221> NAME/KEY: misc_feature
<222> LOCATION: 21
<223> OTHER INFORMATION: n = 2'-O-methyluridine-5'-monophosphate
<220> FEATURE:
<221> NAME/KEY: misc_feature
<222> LOCATION: 22
<223> OTHER INFORMATION: n = 2'-O-methyl-cytidine-5'-phosphorothioate

<400> SEQUENCE: 39
nagggnngaa gcnananacc nnu                                  23

<210> SEQ ID NO 40
<211> LENGTH: 21

```
<212> TYPE: RNA
<213> ORGANISM: Artificial Sequence
<220> FEATURE:
<223> OTHER INFORMATION: Synthetically generated oligonucleotide

<400> SEQUENCE: 40
gguguauggc uucaacccug a                                           21

<210> SEQ ID NO 41
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 41
ucaggguuga agccauacac cuc                                         23

<210> SEQ ID NO 42
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 5, 7, 11, 19
<223> OTHER INFORMATION: n = 2'-O-methyluridine-5'-monophosphate
<220> FEATURE:
<221> NAME/KEY: misc_feature
<222> LOCATION: 13
<223> OTHER INFORMATION: n = 2'-O-methylcytidine-5'-monophosphate

<400> SEQUENCE: 42
ggngnanggc nunaacccng a                                           21

<210> SEQ ID NO 43
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 14, 18, 21
<223> OTHER INFORMATION: n = 2'-O-methylcytidine-5'-monophosphate
<220> FEATURE:
<221> NAME/KEY: misc_feature
<222> LOCATION: 7, 8, 16
<223> OTHER INFORMATION: n = 2'-O-methyluridine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 43
unagggnnga agcnananac nnc                                         23

<210> SEQ ID NO 44
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 5, 7, 11, 19
<223> OTHER INFORMATION: n = 2'-fluoro-2'-deoxy-uridine-5'-monophosphate
<220> FEATURE:
<221> NAME/KEY: misc_difference
<222> LOCATION: 13
<223> OTHER INFORMATION: n = 2'-fluoro-2'-deoxy-cytidine-5'-
```

-continued monophosphate

<400> SEQUENCE: 44
ggngnanggc nunaacccng a                                             21

<210> SEQ ID NO 45
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 14, 18
<223> OTHER INFORMATION: n = 2'-fluoro-2'-deoxy-cytidine-5'-
      monophosphate
<220> FEATURE:
<221> NAME/KEY: misc_feature
<222> LOCATION: 7, 8, 16
<223> OTHER INFORMATION: n = 2'-fluoro-2'-deoxy-uridine-5'-monophosphate
<220> FEATURE:
<221> NAME/KEY: misc_feature
<222> LOCATION: 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 45
unagggnnga agcnananac nnc                                           23

<210> SEQ ID NO 46
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 46
cugaacauca agaggggcau c                                             21

<210> SEQ ID NO 47
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 47
gaugccccuc uugauguuca gga                                           23

<210> SEQ ID NO 48
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2
<223> OTHER INFORMATION: n = 2'-O-methyluridine-5'-monophosphate
<220> FEATURE:
<221> NAME/KEY: misc_ feature
<222> LOCATION: 6, 18
<223> OTHER INFORMATION: n = 2'-O-methylcytidine-5'-monophosphate

<400> SEQUENCE: 48
cngaanauca agagggnau c                                              21

```
<210> SEQ ID NO 49
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_ feature
<222> LOCATION: 3, 11, 12, 15, 17
<223> OTHER INFORMATION: n = 2'-O-methyluridine-5'-monophosphate
<220> FEATURE:
<221> NAME/KEY: misc_feature
<222> LOCATION: 19
<223> OTHER INFORMATION: n = 2'-O-methylcytidine-5'-monophosphate

<400> SEQUENCE: 49
gangccccuc nngangnuna gga                                            23

<210> SEQ ID NO 50
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2
<223> OTHER INFORMATION: n = 2'-fluoro-2'-deoxy-uridine-5'-monophosphate
<220> FEATURE:
<221> NAME/KEY: misc_feature
<222> LOCATION: 6, 18
<223> OTHER INFORMATION: n = 2'-fluoro-2'-deoxy-cytidine-5'-
      monophosphate

<400> SEQUENCE: 50
cngaanauca agagggnau c                                               21

<210> SEQ ID NO 51
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 11, 12, 15, 17
<223> OTHER INFORMATION: n = 2'-fluoro-2'-deoxy-uridine-5'-monophosphate
<220> FEATURE:
<221> NAME/KEY: misc_feature
<222> LOCATION: 19
<223> OTHER INFORMATION: n = 2'-fluoro-2'-deoxy-cytidine-5'-
      monophosphate
<220> FEATURE:
<221> NAME/KEY: misc_feature
<222> LOCATION: 21
<223> OTHER INFORMATION: n = 2'-O-methylguanosine-5'-monophosphate
<220> FEATURE:
<221> NAME/KEY: misc_feature
<222> LOCATION: 22
<223> OTHER INFORMATION: n = 2'-O-methyl-guanosine -5'-phosphorothioate

<400> SEQUENCE: 51
gangccccuc nngangnuna nna                                            23

<210> SEQ ID NO 52
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 52
gccccaucac uuuacaagcc u                                              21
```

<210> SEQ ID NO 53
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 53
aggcuuguaa agugaugggg cug                                    23

<210> SEQ ID NO 54
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 5, 8, 15
<223> OTHER INFORMATION: n = 2'-O-methylcytidine-5'-monophosphate
<220> FEATURE:
<221> NAME/KEY: misc_feature
<222> LOCATION: 11, 12, 13
<223> OTHER INFORMATION: n = 2'-O-methyluridine-5'-monophosphate

<400> SEQUENCE: 54
gcccnaunac nnnanaagcc u                                      21

<210> SEQ ID NO 55
<211> LENGTH: 22
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 5, 6, 8, 13, 16
<223> OTHER INFORMATION: n = 2'-O-methyluridine-5'-monophosphate
<220> FEATURE:
<221> NAME/KEY: misc_feature
<222> LOCATION: 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 55
aggcnngnaa agnganggggg nn                                    22

<210> SEQ ID NO 56
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 5, 8, 15
<223> OTHER INFORMATION: n = 2'-fluoro-2'-deoxy-cytidine-5'-
      monophosphate
<220> FEATURE:
<221> NAME/KEY: misc_feature
<222> LOCATION: 11, 12, 13
<223> OTHER INFORMATION: n = 2'-fluoro-2'-deoxy-uridine-5'-monophosphate

<400> SEQUENCE: 56
gcccnaunac nnnanaagcc u                                      21

<210> SEQ ID NO 57

```
<211> LENGTH: 22
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 5, 6, 8, 13, 16
<223> OTHER INFORMATION: n = 2'-fluoro-2'-deoxy-uridine-5'-monophosphate
<220> FEATURE:
<221> NAME/KEY: misc_feature
<222> LOCATION: 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 57
aggcnngnaa agngangggg nn                                                22

<210> SEQ ID NO 58
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 58
ucacauccuc caguggcuga a                                                 21

<210> SEQ ID NO 59
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 59
uucagccacu ggaggaugug agu                                               23

<210> SEQ ID NO 60
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 4, 11
<223> OTHER INFORMATION: n = 2'-O-methylcytidine-5'-monophosphate
<220> FEATURE:
<221> NAME/KEY: misc_feature
<222> LOCATION: 14, 18
<223> OTHER INFORMATION: n = 2'-O-methyluridine-5'-monophosphate

<400> SEQUENCE: 60
unanauccuc nagnggcnga a                                                 21

<210> SEQ ID NO 61
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 10, 17, 19
<223> OTHER INFORMATION: n = 2'-O-methyluridine-5'-monophosphate
<220> FEATURE:
<221> NAME/KEY: misc_feature
<222> LOCATION: 3, 7
```

```
<223> OTHER INFORMATION: n = 2'-O-methylcytidine-5'-monophosphate

<400> SEQUENCE: 61
nunagcnacn ggaggangng agu                                              23

<210> SEQ ID NO 62
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 4, 11
<223> OTHER INFORMATION: n = 2'-fluoro-2'-deoxy-cytidine-5'-
      monophosphate
<220> FEATURE:
<221> NAME/KEY: misc_feature
<222> LOCATION: 14, 18
<223> OTHER INFORMATION: n = 2'-fluoro-2'-deoxy-uridine-5'-monophosphate

<400> SEQUENCE: 62
unanauccuc nagnggcnga a                                                21

<210> SEQ ID NO 63
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 10, 17, 19
<223> OTHER INFORMATION: n = 2'-fluoro-2'-deoxy-uridine-5'-monophosphate
<220> FEATURE:
<221> NAME/KEY: misc_feature
<222> LOCATION: 3, 7
<223> OTHER INFORMATION: n = 2'-fluoro-2'-deoxy-cytidine-5'-
      monophosphate
<220> FEATURE:
<221> NAME/KEY: misc_difference
<222> LOCATION: 21
<223> OTHER INFORMATION: n = 2'-O-methyl-adenosine-5'-phosphorothioate
<220> FEATURE:
<221> NAME/KEY: misc_feature
<222> LOCATION: 22
<223> OTHER INFORMATION: n = 2'-O-methyl-guanosine -5'-phosphorothioate

<400> SEQUENCE: 63
nunagcnacn ggaggangng nnu                                              23

<210> SEQ ID NO 64
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 64
gaguuuguga caaauauggg c                                                21

<210> SEQ ID NO 65
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 65
gcccauauuu gucacaaacu cca                                              23
```

```
<210> SEQ ID NO 66
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 5, 6, 8, 15, 17
<223> OTHER INFORMATION: n = 2'-O-methyluridine-5'-monophosphate
<220> FEATURE:
<221> NAME/KEY: misc_feature
<222> LOCATION: 11
<223> OTHER INFORMATION: n = 2'-O-methylcytidine-5'-monophosphate

<400> SEQUENCE: 66
gagnnngnga naananggg c                                              21

<210> SEQ ID NO 67
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 6, 8, 9, 10
<223> OTHER INFORMATION: n = 2'-O-methyluridine-5'-monophosphate
<220> FEATURE:
<221> NAME/KEY: misc_feature
<222> LOCATION: 13, 15, 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-cytidine-5'-phosphorothioate

<400> SEQUENCE: 67
gcccanannn gunanaaacu nna                                           23

<210> SEQ ID NO 68
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 5, 6, 8, 15, 17
<223> OTHER INFORMATION: n = 2'-fluoro-2'-deoxy-uridine-5'-monophosphate
<220> FEATURE:
<221> NAME/KEY: misc_feature
<222> LOCATION: 11
<223> OTHER INFORMATION: n = 2'-fluoro-2'-deoxy-cytidine-5'-
      monophosphate

<400> SEQUENCE: 68
gagnnngnga naananggg c                                              21

<210> SEQ ID NO 69
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 6, 8, 9, 10
<223> OTHER INFORMATION: n = 2'-fluoro-2'-deoxy-uridine-5'-monophosphate
<220> FEATURE:
<221> NAME/KEY: misc_feature
<222> LOCATION: 13, 15
<223> OTHER INFORMATION: n = 2'-fluoro-2'-deoxy-cytidine-5'-
```

```
       monophosphate
<220> FEATURE:
<221> NAME/KEY: misc_feature
<222> LOCATION: 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-cytidine-5'-phosphorothioate

<400> SEQUENCE: 69
gcccanannn gunanaaacu nna                                            23

<210> SEQ ID NO 70
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 70
gaacaccaac uucuuccacg a                                              21

<210> SEQ ID NO 71
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 71
ucguggaaga aguuguguu cau                                             23

<210> SEQ ID NO 72
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 7, 17
<223> OTHER INFORMATION: n = 2'-O-methylcytidine-5'-monophosphate
<220> FEATURE:
<221> NAME/KEY: misc_feature
<222> LOCATION: 11, 14
<223> OTHER INFORMATION: n = 2'-O-methylcytidine-5'-monophosphate

<400> SEQUENCE: 72
gaanacnaac nucnucnacg a                                              21

<210> SEQ ID NO 73
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 13, 14, 17, 19
<223> OTHER INFORMATION: n = 2'-O-methylcytidine-5'-monophosphate
<220> FEATURE:
<221> NAME/KEY: misc_feature
<222> LOCATION: 21
<223> OTHER INFORMATION: n = 2'-O-methylcytidine-5'-monophosphate

<400> SEQUENCE: 73
ucgnggaaga agnnggngnu nau                                            23

<210> SEQ ID NO 74
```

```
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 7, 17
<223> OTHER INFORMATION: n = 2'-fluoro-2'-deoxy-cytidine-5'-
      monophosphate
<220> FEATURE:
<221> NAME/KEY: misc_feature
<222> LOCATION: 11, 14
<223> OTHER INFORMATION: n = 2'-fluoro-2'-deoxy-uridine-5'-monophosphate

<400> SEQUENCE: 74
gaanacnaac nucnucnacg a                                           21

<210> SEQ ID NO 75
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 13, 14, 17, 19
<223> OTHER INFORMATION: n = 2'-fluoro-2'-deoxy-uridine-5'-monophosphate
<220> FEATURE:
<221> NAME/KEY: misc_feature
<222> LOCATION: 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-adenosine-5'-phosphorothioate

<400> SEQUENCE: 75
ucgnggaaga agnnggngnu nnu                                         23

<210> SEQ ID NO 76
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 76
caccaacuuc uuccacgagu c                                           21

<210> SEQ ID NO 77
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 77
gacucgugga agaaguuggu guu                                         23

<210> SEQ ID NO 78
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = 2'-O-methyl-cytidine (5'-hydroxyl)
<220> FEATURE:
<221> NAME/KEY: misc_feature
```

<222> LOCATION: 4, 14
<223> OTHER INFORMATION: n = 2'-O-methylcytidine-5'-monophosphate
<220> FEATURE:
<221> NAME/KEY: misc_feature
<222> LOCATION: 8, 11
<223> OTHER INFORMATION: n = 2'-O-methylcytidine-5'-monophosphate

<400> SEQUENCE: 78
nacnaacnuc nucnacgagu c                                         21

<210> SEQ ID NO 79
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 7, 16, 17, 20
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 79
gacucgngga agaagnnggn gnu                                       23

<210> SEQ ID NO 80
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = 2'-fluoro-2'-deoxy-cytidine-(5'-hydroxyl)
<220> FEATURE:
<221> NAME/KEY: misc_feature
<222> LOCATION: 4, 14
<223> OTHER INFORMATION: n = 2'-fluoro-2'-deoxy-cytidine-5'-
    monophosphate
<220> FEATURE:
<221> NAME/KEY: misc_feature
<222> LOCATION: 8, 11
<223> OTHER INFORMATION: n = 2'-fluoro-2'-deoxy-uridine-5'-monophosphate

<400> SEQUENCE: 80
nacnaacnuc nucnacgagu c                                         21

<210> SEQ ID NO 81
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 7, 16, 17
<223> OTHER INFORMATION: n = 2'-fluoro-2'-deoxy-uridine-5'-monophosphate
<220> FEATURE:
<221> NAME/KEY: misc_feature
<222> LOCATION: 20
<223> OTHER INFORMATION: n = 2'-O-methyl-uridine-5'-phosphorothioate
<220> FEATURE:
<221> NAME/KEY: misc_feature
<222> LOCATION: 21
<223> OTHER INFORMATION: n = 2'-O-methylguanosine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

```
<400> SEQUENCE: 81
gacucgngga agaagnnggn nnu                                           23

<210> SEQ ID NO 82
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 82
aucaaguguc aucacacuga a                                             21

<210> SEQ ID NO 83
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 83
uucaguguga ugacacuuga uuu                                           23

<210> SEQ ID NO 84
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 10, 13, 15
<223> OTHER INFORMATION: n = 2'-O-methylcytidine-5'-monophosphate
<220> FEATURE:
<221> NAME/KEY: misc_feature
<222> LOCATION: 7, 18
<223> OTHER INFORMATION: n = 2'-O-methyluridine-5'-monophosphate

<400> SEQUENCE: 84
aunaagngun aunanacnga a                                             21

<210> SEQ ID NO 85
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 6, 8, 11, 17, 18, 21
<223> OTHER INFORMATION: n = 2'-O-methyluridine-5'-monophosphate
<220> FEATURE:
<221> NAME/KEY: misc_feature
<222> LOCATION: 3, 14
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 85
nunagngnga nganacnnga nnu                                           23

<210> SEQ ID NO 86
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
```

```
<221> NAME/KEY: misc_feature
<222> LOCATION: 3, 10, 13, 15
<223> OTHER INFORMATION: n = 2'-fluoro-2'-deoxy-cytidine-5'-
      monophosphate
<220> FEATURE:
<221> NAME/KEY: misc_feature
<222> LOCATION: 7, 18
<223> OTHER INFORMATION: n = 2'-fluoro-2'-deoxy-uridine-5'-monophosphate

<400> SEQUENCE: 86
aunaagngun aunanacnga a                                              21

<210> SEQ ID NO 87
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1, 6, 8, 11, 17, 18
<223> OTHER INFORMATION: n = 2'-fluoro-2'-deoxy-uridine-5'-monophosphate
<220> FEATURE:
<221> NAME/KEY: misc_feature
<222> LOCATION: 3, 14
<223> OTHER INFORMATION: n = 2'-fluoro-2'-deoxy-cytidine-5'-
      monophosphate
<220> FEATURE:
<221> NAME/KEY: misc_feature
<222> LOCATION: 21
<223> OTHER INFORMATION: n = 2'-O-methyluridine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 87
nunagngnga nganacnnga nnu                                            23

<210> SEQ ID NO 88
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 88
gucaucacac ugaauaccaa u                                              21

<210> SEQ ID NO 89
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 89
auugguauuc agugugauga cac                                            23

<210> SEQ ID NO 90
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 6, 8, 18
<223> OTHER INFORMATION: n = 2'-O-methylcytidine-5'-monophosphate
<220> FEATURE:
<221> NAME/KEY: misc_feature
<222> LOCATION: 11, 15
```

<223> OTHER INFORMATION: n = 2'-O-methyluridine-5'-monophosphate

<400> SEQUENCE: 90
gunaunanac ngaanacnaa n                                              21

<210> SEQ ID NO 91
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 3, 6, 8, 13, 15, 18
<223> OTHER INFORMATION: n = 2'-O-methyluridine-5'-monophosphate
<220> FEATURE:
<221> NAME/KEY: misc_feature
<222> LOCATION: 10, 21
<223> OTHER INFORMATION: n = 2'-O-methylcytidine-5'-monophosphate

<400> SEQUENCE: 91 anngganun agngnganga nac                                             23

<210> SEQ ID NO 92
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 6, 8, 18
<223> OTHER INFORMATION: n = 2'-fluoro-2'-deoxy-cytidine-5'-
      monophosphate
<220> FEATURE:
<221> NAME/KEY: misc_feature
<222> LOCATION: 11, 15
<223> OTHER INFORMATION: n = 2'-fluoro-2'-deoxy-uridine-5'-monophosphate

<400> SEQUENCE: 92
gunaunanac ngaanacnaa u                                              21

<210> SEQ ID NO 93
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 3, 6, 8, 13, 15, 18
<223> OTHER INFORMATION: n = 2'-fluoro-2'-deoxy-uridine-5'-monophosphate
<220> FEATURE:
<221> NAME/KEY: misc_feature
<222> LOCATION: 10
<223> OTHER INFORMATION: n = 2'-fluoro-2'-deoxy-cytidine-5'-
      monophosphate
<220> FEATURE:
<221> NAME/KEY: misc_feature
<222> LOCATION: 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-adenosine-5'-phosphorothioate

<400> SEQUENCE: 93 anngganun agngnganga nnc                                             23

<210> SEQ ID NO 94
<211> LENGTH: 21
<212> TYPE: RNA

```
<213> ORGANISM: Artificial Sequence
<220> FEATURE:
<223> OTHER INFORMATION: Synthetically generated oligonucleotide

<400> SEQUENCE: 94
gauugauuga ccguccauu c                                          21

<210> SEQ ID NO 95
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 95
gaauggacag gucaaucaau cuu                                       23

<210> SEQ ID NO 96
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 4, 7, 8, 13, 19
<223> OTHER INFORMATION: n = 2'-O-methyluridine-5'-monophosphate
<220> FEATURE:
<221> NAME/KEY: misc_feature
<222> LOCATION: 17
<223> OTHER INFORMATION: n = 2'-O-methylcytidine-5'-monophosphate

<400> SEQUENCE: 96
ganngannga ccngucnanu c                                         21

<210> SEQ ID NO 97
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4
<223> OTHER INFORMATION: n = 2'-O-methyluridine-5'-monophosphate
<220> FEATURE:
<221> NAME/KEY: misc_feature
<222> LOCATION: 8, 13, 17, 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 97
gaangganag gunaaunaau nnu                                       23

<210> SEQ ID NO 98
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 4, 7, 8, 13
<223> OTHER INFORMATION: n = 2'-fluoro-2'-deoxy-uridine-5'-monophosphate
<220> FEATURE:
<221> NAME/KEY: misc_feature
<222> LOCATION: 17
<223> OTHER INFORMATION: n = 2'-fluoro-2'-deoxy-cytidine-5'-
    monophosphate
```

```
<220> FEATURE:
<221> NAME/KEY: misc_feature
<222> LOCATION: 19
<223> OTHER INFORMATION: n = 2'-O-methyluridine-5'-monophosphate

<400> SEQUENCE: 98
ganngannga ccngucnanu c                                              21

<210> SEQ ID NO 99
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4
<223> OTHER INFORMATION: n = 2'-fluoro-2'-deoxy-uridine-5'-monophosphate
<220> FEATURE:
<221> NAME/KEY: misc_feature
<222> LOCATION: 8, 13, 17
<223> OTHER INFORMATION: n = 2'-fluoro-2'-deoxy-cytidine-5'-
      monophosphate
<220> FEATURE:
<221> NAME/KEY: misc_feature
<222> LOCATION: 21
<223> OTHER INFORMATION: n = 2'-O-methylcytidine-5'-monophosphate
<220> FEATURE:
<221> NAME/KEY: misc_feature
<222> LOCATION: 22
<223> OTHER INFORMATION: n = 2'-O-methyl-uridine-5'-phosphorothioate

<400> SEQUENCE: 99
gaangganag gunaaunaau nnu                                            23

<210> SEQ ID NO 100
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 100
cuguccauuc aaaacuacca c                                              21

<210> SEQ ID NO 101
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 101
gugguaguuu ugaauggaca ggu                                            23

<210> SEQ ID NO 102
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_difference
<222> LOCATION: 2, 8, 16
<223> OTHER INFORMATION: n = 2'-O-methyluridine-5'-monophosphate
<220> FEATURE:
<221> NAME/KEY: misc_feature
<222> LOCATION: 6, 10, 19
<223> OTHER INFORMATION: n = 2'-O-methylcytidine-5'-monophosphate

<400> SEQUENCE: 102
```
cngucnanun aaaacnacna c                                         21

<210> SEQ ID NO 103
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 5, 8, 9, 10, 11, 15
<223> OTHER INFORMATION: n = 2'-O-methyluridine-5'-monophosphate
<220> FEATURE:
<221> NAME/KEY: misc_feature
<222> LOCATION: 19
<223> OTHER INFORMATION: n = 2'-O-methylcytidine-5'-monophosphate

<400> SEQUENCE: 103
gnggnagnnn ngaanggana ggu                                       23

<210> SEQ ID NO 104
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 8, 16
<223> OTHER INFORMATION: n = 2'-fluoro-2'-deoxy-uridine-5'-monophosphate
<220> FEATURE:
<221> NAME/KEY: misc_feature
<222> LOCATION: 6, 10, 19
<223> OTHER INFORMATION: n = 2'-fluoro-2'-deoxy-cytidine-5'-
      monophosphate

<400> SEQUENCE: 104
cngucnanun aaaacnacna c                                         21

<210> SEQ ID NO 105
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 5, 8, 9, 10, 11, 15
<223> OTHER INFORMATION: n = 2'-fluoro-2'-deoxy-uridine-5'-monophosphate
<220> FEATURE:
<221> NAME/KEY: misc_feature
<222> LOCATION: 19
<223> OTHER INFORMATION: n = 2'-fluoro-2'-deoxy-cytidine-5'-
      monophosphate
<220> FEATURE:
<221> NAME/KEY: misc_feature
<222> LOCATION: 21
<223> OTHER INFORMATION: n = 2'-O-methylguanosine-5'-monophosphate
<220> FEATURE:
<221> NAME/KEY: misc_feature
<222> LOCATION: 22
<223> OTHER INFORMATION: n = 2'-O-methyl-guanosine -5'-phosphorothioate

<400> SEQUENCE: 105
gnggnagnnn ngaanggana nnu                                       23

<210> SEQ ID NO 106
<211> LENGTH: 21
<212> TYPE: RNA
<213> ORGANISM: Artificial Sequence
<220> FEATURE:
<223> OTHER INFORMATION: Synthetically generated oligonucleotide

```
<400> SEQUENCE: 106
gucaucacac ugaauaccaa u                                      21

<210> SEQ ID NO 107
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 107
auugguauuc agugugauga cac                                    23

<210> SEQ ID NO 108
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 3, 6, 8, 18
<223> OTHER INFORMATION: n = 2'-O-methyl-cytidine-5'-phosphorothioate
<220> FEATURE:
<221> NAME/KEY: misc_feature
<222> LOCATION: 11, 15
<223> OTHER INFORMATION: n = 2'-O-methyluridine-5'-monophosphate

<400> SEQUENCE: 108
gunaunanac ngaanacnaa u                                      21

<210> SEQ ID NO 109
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2, 3, 6, 8, 13, 15, 18
<223> OTHER INFORMATION: n = 2'-O-methyluridine-5'-monophosphate
<220> FEATURE:
<221> NAME/KEY: misc_feature
<222> LOCATION: 10, 21
<223> OTHER INFORMATION: n = 2'-O-methylcytidine-5'-monophosphate

<400> SEQUENCE: 109
annggnanun agngnganga nac                                    23

<210> SEQ ID NO 110
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 110
acggcuagcu gugaaagguc c                                      21

<210> SEQ ID NO 111
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 111
ggaccuuuca cagcuagccg uga                                    23
```

-continued

```
<210> SEQ ID NO 112
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 112
ucgaaguacu cagcguaagt                                                  20

<210> SEQ ID NO 113
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 113
ucgaaguacu cagcguaag                                                   19

<210> SEQ ID NO 114
<211> LENGTH: 16
<212> TYPE: RNA
<213> ORGANISM: Artificial Sequence
<220> FEATURE:
<223> OTHER INFORMATION: Synthetically generated oligonucleotide

<400> SEQUENCE: 114
ucgaaguacu cagcgu                                                      16

<210> SEQ ID NO 115
<211> LENGTH: 16
<212> TYPE: RNA
<213> ORGANISM: Artificial Sequence
<220> FEATURE:
<223> OTHER INFORMATION: Synthetically generated oligonucleotide

<400> SEQUENCE: 115
ucgaaguacu cagcgu                                                      16

<210> SEQ ID NO 116
<211> LENGTH: 7
<212> TYPE: RNA
<213> ORGANISM: Artificial Sequence
<220> FEATURE:
<223> OTHER INFORMATION: Synthetically generated oligonucleotide

<400> SEQUENCE: 116 ucgaagu                                                                 7

<210> SEQ ID NO 117
<211> LENGTH: 5
<212> TYPE: DNA
<213> ORGANISM: Artificial Sequence
<220> FEATURE:
<223> OTHER INFORMATION: Synthetically generated oligonucleotide

<400> SEQUENCE: 117 aagtt                                                                   5

<210> SEQ ID NO 118
<211> LENGTH: 20
<212> TYPE: DNA
<213> ORGANISM: Artificial Sequence
<220> FEATURE:
<223> OTHER INFORMATION: Synthetically generated oligonucleotide
```

```
<400> SEQUENCE: 118
cuuacgcuga guacuucgat                                               20

<210> SEQ ID NO 119
<211> LENGTH: 19
<212> TYPE: RNA
<213> ORGANISM: Artificial Sequence
<220> FEATURE:
<223> OTHER INFORMATION: Synthetically generated oligonucleotide

<400> SEQUENCE: 119
cuuacgcuga guacuucga                                                19

<210> SEQ ID NO 120
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 120
acgcugagua cuucgatt                                                 18

<210> SEQ ID NO 121
<211> LENGTH: 17
<212> TYPE: DNA
<213> ORGANISM: Artificial Sequence
<220> FEATURE:
<223> OTHER INFORMATION: Synthetically generated oligonucleotide

<400> SEQUENCE: 121
acgcugagua cuucgat                                                  17

<210> SEQ ID NO 122
<211> LENGTH: 9
<212> TYPE: RNA
<213> ORGANISM: Artificial Sequence
<220> FEATURE:
<223> OTHER INFORMATION: Synthetically generated oligonucleotide

<400> SEQUENCE: 122 acgcugagu                                                            9

<210> SEQ ID NO 123
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 123
uuggugaggu uugauccgct t                                             21

<210> SEQ ID NO 124
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 124
uuggugaggu uugauccgct                                               20

<210> SEQ ID NO 125
<211> LENGTH: 19
<212> TYPE: RNA
```

```
<213> ORGANISM: Artificial Sequence
<220> FEATURE:
<223> OTHER INFORMATION: Synthetically generated oligonucleotide

<400> SEQUENCE: 125
uuggugaggu uugauccgc                                               19

<210> SEQ ID NO 126
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 126
uuggugaggu uugauccgct t                                            21

<210> SEQ ID NO 127
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 127
ggugagguuu gauccgctt                                               19

<210> SEQ ID NO 128
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 128
ggugagguuu gauccgct                                                18

<210> SEQ ID NO 129
<211> LENGTH: 16
<212> TYPE: DNA
<213> ORGANISM: Artificial Sequence
<220> FEATURE:
<223> OTHER INFORMATION: Synthetically generated oligonucleotide

<400> SEQUENCE: 129
ugagguuuga uccgct                                                  16

<210> SEQ ID NO 130
<211> LENGTH: 16
<212> TYPE: DNA
<213> ORGANISM: Artificial Sequence
<220> FEATURE:
<223> OTHER INFORMATION: Synthetically generated oligonucleotide

<400> SEQUENCE: 130
gagguuugau ccgctt                                                  16

<210> SEQ ID NO 131
<211> LENGTH: 11
<212> TYPE: RNA
<213> ORGANISM: Artificial Sequence
<220> FEATURE:
<223> OTHER INFORMATION: Synthetically generated oligonucleotide

<400> SEQUENCE: 131
uuggugaggu u                                                       11
```

```
<210> SEQ ID NO 132
<211> LENGTH: 11
<212> TYPE: RNA
<213> ORGANISM: Artificial Sequence
<220> FEATURE:
<223> OTHER INFORMATION: Synthetically generated oligonucleotide

<400> SEQUENCE: 132
uuggugaggu u                                                              11

<210> SEQ ID NO 133
<211> LENGTH: 10
<212> TYPE: RNA
<213> ORGANISM: Artificial Sequence
<220> FEATURE:
<223> OTHER INFORMATION: Synthetically generated oligonucleotide

<400> SEQUENCE: 133
uuggugaggu                                                                10

<210> SEQ ID NO 134
<211> LENGTH: 10
<212> TYPE: RNA
<213> ORGANISM: Artificial Sequence
<220> FEATURE:
<223> OTHER INFORMATION: Synthetically generated oligonucleotide

<400> SEQUENCE: 134
uuggugaggu                                                                10

<210> SEQ ID NO 135
<211> LENGTH: 10
<212> TYPE: DNA
<213> ORGANISM: Artificial Sequence
<220> FEATURE:
<223> OTHER INFORMATION: Synthetically generated oligonucleotide

<400> SEQUENCE: 135
ugauccgctt                                                                10

<210> SEQ ID NO 136
<211> LENGTH: 9
<212> TYPE: RNA
<213> ORGANISM: Artificial Sequence
<220> FEATURE:
<223> OTHER INFORMATION: Synthetically generated oligonucleotide

<400> SEQUENCE: 136 ggugagguu                                                                  9

<210> SEQ ID NO 137
<211> LENGTH: 9
<212> TYPE: RNA
<213> ORGANISM: Artificial Sequence
<220> FEATURE:
<223> OTHER INFORMATION: Synthetically generated oligonucleotide

<400> SEQUENCE: 137 ggugagguu                                                                  9

<210> SEQ ID NO 138
<211> LENGTH: 9
<212> TYPE: DNA
<213> ORGANISM: Artificial Sequence
<220> FEATURE:
<223> OTHER INFORMATION: Synthetically generated oligonucleotide
```

-continued

```
<400> SEQUENCE: 138 ugauccgct                                                                9

<210> SEQ ID NO 139
<211> LENGTH: 9
<212> TYPE: DNA
<213> ORGANISM: Artificial Sequence
<220> FEATURE:
<223> OTHER INFORMATION: Synthetically generated oligonucleotide

<400> SEQUENCE: 139 gauccgctt                                                                9

<210> SEQ ID NO 140
<211> LENGTH: 7
<212> TYPE: RNA
<213> ORGANISM: Artificial Sequence
<220> FEATURE:
<223> OTHER INFORMATION: Synthetically generated oligonucleotide

<400> SEQUENCE: 140 gagguuu                                                                  7

<210> SEQ ID NO 141
<211> LENGTH: 7
<212> TYPE: RNA
<213> ORGANISM: Artificial Sequence
<220> FEATURE:
<223> OTHER INFORMATION: Synthetically generated oligonucleotide

<400> SEQUENCE: 141 ugagguu                                                                  7

<210> SEQ ID NO 142
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 142
gcggaucaaa ccucaccaat                                                   20

<210> SEQ ID NO 143
<211> LENGTH: 17
<212> TYPE: RNA
<213> ORGANISM: Artificial Sequence
<220> FEATURE:
<223> OTHER INFORMATION: Synthetically generated oligonucleotide

<400> SEQUENCE: 143
gcggaucaaa ccucacc                                                      17

<210> SEQ ID NO 144
<211> LENGTH: 16
<212> TYPE: RNA
<213> ORGANISM: Artificial Sequence
<220> FEATURE:
<223> OTHER INFORMATION: Synthetically generated oligonucleotide

<400> SEQUENCE: 144
gcggaucaaa ccucac                                                       16

<210> SEQ ID NO 145
<211> LENGTH: 14
<212> TYPE: RNA
```

```
<213> ORGANISM: Artificial Sequence
<220> FEATURE:
<223> OTHER INFORMATION: Synthetically generated oligonucleotide

<400> SEQUENCE: 145
gcggaucaaa ccuc                                                       14

<210> SEQ ID NO 146
<211> LENGTH: 14
<212> TYPE: DNA
<213> ORGANISM: Artificial Sequence
<220> FEATURE:
<223> OTHER INFORMATION: Synthetically generated oligonucleotide

<400> SEQUENCE: 146
caaaccucac caat                                                       14

<210> SEQ ID NO 147
<211> LENGTH: 14
<212> TYPE: DNA
<213> ORGANISM: Artificial Sequence
<220> FEATURE:
<223> OTHER INFORMATION: Synthetically generated oligonucleotide

<400> SEQUENCE: 147
aaaccucacc aatt                                                       14

<210> SEQ ID NO 148
<211> LENGTH: 13
<212> TYPE: RNA
<213> ORGANISM: Artificial Sequence
<220> FEATURE:
<223> OTHER INFORMATION: Synthetically generated oligonucleotide

<400> SEQUENCE: 148
caaaccucac caa                                                        13

<210> SEQ ID NO 149
<211> LENGTH: 13
<212> TYPE: DNA
<213> ORGANISM: Artificial Sequence
<220> FEATURE:
<223> OTHER INFORMATION: Synthetically generated oligonucleotide

<400> SEQUENCE: 149
aaaccucacc aat                                                        13

<210> SEQ ID NO 150
<211> LENGTH: 10
<212> TYPE: RNA
<213> ORGANISM: Artificial Sequence
<220> FEATURE:
<223> OTHER INFORMATION: Synthetically generated oligonucleotide

<400> SEQUENCE: 150
aaaccucacc                                                            10

<210> SEQ ID NO 151
<211> LENGTH: 10
<212> TYPE: RNA
<213> ORGANISM: Artificial Sequence
<220> FEATURE:
<223> OTHER INFORMATION: Synthetically generated oligonucleotide

<400> SEQUENCE: 151
caaaccucac                                                            10
```

```
<210> SEQ ID NO 152
<211> LENGTH: 9
<212> TYPE: RNA
<213> ORGANISM: Artificial Sequence
<220> FEATURE:
<223> OTHER INFORMATION: Synthetically generated oligonucleotide

<400> SEQUENCE: 152 aaaccucac                                                                  9

<210> SEQ ID NO 153
<211> LENGTH: 7
<212> TYPE: RNA
<213> ORGANISM: Artificial Sequence
<220> FEATURE:
<223> OTHER INFORMATION: Synthetically generated oligonucleotide

<400> SEQUENCE: 153 gcggauc                                                                    7

<210> SEQ ID NO 154
<211> LENGTH: 7
<212> TYPE: RNA
<213> ORGANISM: Artificial Sequence
<220> FEATURE:
<223> OTHER INFORMATION: Synthetically generated oligonucleotide

<400> SEQUENCE: 154 aaaccuc                                                                    7

<210> SEQ ID NO 155
<211> LENGTH: 6
<212> TYPE: RNA
<213> ORGANISM: Artificial Sequence
<220> FEATURE:
<223> OTHER INFORMATION: Synthetically generated oligonucleotide

<400> SEQUENCE: 155 gcggau                                                                     6

<210> SEQ ID NO 156
<211> LENGTH: 49
<212> TYPE: DNA
<213> ORGANISM: Artificial Sequence
<220> FEATURE:
<223> OTHER INFORMATION: Synthetically generated oligonucleotide

<400> SEQUENCE: 156
gattggattt tcagaatact gtatagcttt tttctcttgg aaagaaagt                      49

<210> SEQ ID NO 157
<211> LENGTH: 41
<212> TYPE: DNA
<213> ORGANISM: Artificial Sequence
<220> FEATURE:
<223> OTHER INFORMATION: Synthetically generated oligonucleotide

<400> SEQUENCE: 157
cctgcttcgt ttgctgaggt tttttctctt ggaaagaaag t                              41

<210> SEQ ID NO 158
<211> LENGTH: 42
<212> TYPE: DNA
<213> ORGANISM: Artificial Sequence
<220> FEATURE:
<223> OTHER INFORMATION: Synthetically generated oligonucleotide
```

<400> SEQUENCE: 158
gcagtgatgg aagctgcgat atttttctct tggaaagaaa gt    42

<210> SEQ ID NO 159
<211> LENGTH: 47
<212> TYPE: DNA
<213> ORGANISM: Artificial Sequence
<220> FEATURE:
<223> OTHER INFORMATION: Synthetically generated oligonucleotide

<400> SEQUENCE: 159
gaacttctaa tttggactct cctttgtttt tctcttggaa agaaagt    47

<210> SEQ ID NO 160
<211> LENGTH: 40
<212> TYPE: DNA
<213> ORGANISM: Artificial Sequence
<220> FEATURE:
<223> OTHER INFORMATION: Synthetically generated oligonucleotide

<400> SEQUENCE: 160
actccttcag agccagcggt ttttctcttg gaaagaaagt    40

<210> SEQ ID NO 161
<211> LENGTH: 41
<212> TYPE: DNA
<213> ORGANISM: Artificial Sequence
<220> FEATURE:
<223> OTHER INFORMATION: Synthetically generated oligonucleotide

<400> SEQUENCE: 161
actcccatgc tccgttctca tttttctctt ggaaagaaag t    41

<210> SEQ ID NO 162
<211> LENGTH: 46
<212> TYPE: DNA
<213> ORGANISM: Artificial Sequence
<220> FEATURE:
<223> OTHER INFORMATION: Synthetically generated oligonucleotide

<400> SEQUENCE: 162
agggtaagct gattgtttat cttgattttt ctcttggaaa gaaagt    46

<210> SEQ ID NO 163
<211> LENGTH: 46
<212> TYPE: DNA
<213> ORGANISM: Artificial Sequence
<220> FEATURE:
<223> OTHER INFORMATION: Synthetically generated oligonucleotide

<400> SEQUENCE: 163
ggttccattc cctatgtcag catttttagg cataggaccc gtgtct    46

<210> SEQ ID NO 164
<211> LENGTH: 50
<212> TYPE: DNA
<213> ORGANISM: Artificial Sequence
<220> FEATURE:
<223> OTHER INFORMATION: Synthetically generated oligonucleotide

<400> SEQUENCE: 164
attaatctta gggtttgaga gttgtgtttt taggcatagg acccgtgtct    50

<210> SEQ ID NO 165
<211> LENGTH: 49
<212> TYPE: DNA

```
<213> ORGANISM: Artificial Sequence
<220> FEATURE:
<223> OTHER INFORMATION: Synthetically generated oligonucleotide

<400> SEQUENCE: 165
cactgtgttt gattttccct caatattttt aggcatagga cccgtgtct                    49

<210> SEQ ID NO 166
<211> LENGTH: 51
<212> TYPE: DNA
<213> ORGANISM: Artificial Sequence
<220> FEATURE:
<223> OTHER INFORMATION: Synthetically generated oligonucleotide

<400> SEQUENCE: 166 tgtattttt tctgtgtgta aacttgcttt ttaggcatag gacccgtgtc t                  51

<210> SEQ ID NO 167
<211> LENGTH: 49
<212> TYPE: DNA
<213> ORGANISM: Artificial Sequence
<220> FEATURE:
<223> OTHER INFORMATION: Synthetically generated oligonucleotide

<400> SEQUENCE: 167
caatcactcc attactaagc tccagttttt aggcatagga cccgtgtct                    49

<210> SEQ ID NO 168
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 168
tgccaaaagt aggtacttca attg                                               24

<210> SEQ ID NO 169
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 169
tttgcatcta atgtgaaaag agga                                               24

<210> SEQ ID NO 170
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 170
catttgcttg aaaatcaaaa ttga                                               24

<210> SEQ ID NO 171
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 171
ggtacttgct ggagaacttc actg                                               24
```

<210> SEQ ID NO 172
<211> LENGTH: 23
<212> TYPE: DNA
<213> ORGANISM: Artificial Sequence
<220> FEATURE:
<223> OTHER INFORMATION: Synthetically generated oligonucleotide

<400> SEQUENCE: 172
gcatttccaa aaacagcat ttc                                              23

<210> SEQ ID NO 173
<211> LENGTH: 41
<212> TYPE: DNA
<213> ORGANISM: Artificial Sequence
<220> FEATURE:
<223> OTHER INFORMATION: Synthetically generated oligonucleotide

<400> SEQUENCE: 173
gaatttgcca tgggtggaat tttttctctt ggaaagaaag t                         41

<210> SEQ ID NO 174
<211> LENGTH: 41
<212> TYPE: DNA
<213> ORGANISM: Artificial Sequence
<220> FEATURE:
<223> OTHER INFORMATION: Synthetically generated oligonucleotide

<400> SEQUENCE: 174
ggagggatct cgctcctgga tttttctctt ggaaagaaag t                         41

<210> SEQ ID NO 175
<211> LENGTH: 40
<212> TYPE: DNA
<213> ORGANISM: Artificial Sequence
<220> FEATURE:
<223> OTHER INFORMATION: Synthetically generated oligonucleotide

<400> SEQUENCE: 175
ccccagcctt ctccatggtt ttttctcttg gaaagaaagt                           40

<210> SEQ ID NO 176
<211> LENGTH: 40
<212> TYPE: DNA
<213> ORGANISM: Artificial Sequence
<220> FEATURE:
<223> OTHER INFORMATION: Synthetically generated oligonucleotide

<400> SEQUENCE: 176 gctccccct gcaaatgagt ttttctcttg gaaagaaagt                            40

<210> SEQ ID NO 177
<211> LENGTH: 42
<212> TYPE: DNA
<213> ORGANISM: Artificial Sequence
<220> FEATURE:
<223> OTHER INFORMATION: Synthetically generated oligonucleotide

<400> SEQUENCE: 177
agccttgacg gtgccatgtt tttaggcata ggacccgtgt ct                        42

<210> SEQ ID NO 178
<211> LENGTH: 45
<212> TYPE: DNA
<213> ORGANISM: Artificial Sequence
<220> FEATURE:
<223> OTHER INFORMATION: Synthetically generated oligonucleotide

<400> SEQUENCE: 178
gatgacaagc ttcccgttct cttttttaggc ataggacccg tgtct                45

<210> SEQ ID NO 179
<211> LENGTH: 46
<212> TYPE: DNA
<213> ORGANISM: Artificial Sequence
<220> FEATURE:
<223> OTHER INFORMATION: Synthetically generated oligonucleotide

<400> SEQUENCE: 179
agatggtgat gggatttcca ttttttttagg cataggaccc gtgtct             46

<210> SEQ ID NO 180
<211> LENGTH: 44
<212> TYPE: DNA
<213> ORGANISM: Artificial Sequence
<220> FEATURE:
<223> OTHER INFORMATION: Synthetically generated oligonucleotide

<400> SEQUENCE: 180
gcatcgcccc acttgatttt tttttaggca taggacccgt gtct                44

<210> SEQ ID NO 181
<211> LENGTH: 43
<212> TYPE: DNA
<213> ORGANISM: Artificial Sequence
<220> FEATURE:
<223> OTHER INFORMATION: Synthetically generated oligonucleotide

<400> SEQUENCE: 181
cacgacgtac tcagcgccat ttttaggcat aggacccgtg tct                 43

<210> SEQ ID NO 182
<211> LENGTH: 46
<212> TYPE: DNA
<213> ORGANISM: Artificial Sequence
<220> FEATURE:
<223> OTHER INFORMATION: Synthetically generated oligonucleotide

<400> SEQUENCE: 182
ggcagagatg atgacccttt tgtttttagg cataggaccc gtgtct              46

<210> SEQ ID NO 183
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 183
ggtgaagacg ccagtggact c                                          21

<210> SEQ ID NO 184
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = deoxythymidine

<400> SEQUENCE: 184
cuuacgcuga guacuucgan n                                          21

```
<210> SEQ ID NO 185
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = deoxythymidine

<400> SEQUENCE: 185
ucgaaguacu cagcguaagn n                                              21
```